(12) United States Patent
Bianchi et al.

(10) Patent No.: US 8,470,038 B2
(45) Date of Patent: *Jun. 25, 2013

(54) ADJUSTABLE AND FIXED ASSEMBLED BONE-TENDON-BONE GRAFT

(75) Inventors: John R. Bianchi, Gainesville, FL (US); Zhukauskas A. Arunas, Gainesville, FL (US); Todd E. Goede, Alachua, FL (US); Lauren M. Brown, Gainesville, FL (US); Guy B. Grover, Gainesville, FL (US); Wesley I. Lewis, Archer, FL (US); Joe Kutsavage, High Springs, FL (US)

(73) Assignee: RTI Biologics, Inc., Alachua, FL (US)

( * ) Notice: Subject to any disclaimer, the term of this patent is extended or adjusted under 35 U.S.C. 154(b) by 1940 days.

This patent is subject to a terminal disclaimer.

(21) Appl. No.: 11/313,280

(22) Filed: Dec. 19, 2005

(65) Prior Publication Data
US 2006/0229722 A1    Oct. 12, 2006

Related U.S. Application Data

(63) Continuation-in-part of application No. 11/073,281, filed on Mar. 4, 2005, now Pat. No. 7,776,089.

(51) Int. Cl.
*A61F 2/08* (2006.01)
(52) U.S. Cl.
USPC .................................. 623/13.14; 623/13.17
(58) Field of Classification Search
USPC ............................................ 623/13.11–13.2
See application file for complete search history.

(56) References Cited

U.S. PATENT DOCUMENTS

| D3,574 S | 7/1869 | Benedict |
| D26,174 S | 10/1896 | Bren |
| 3,705,586 A | 12/1972 | Sarracino |

(Continued)

FOREIGN PATENT DOCUMENTS

| DE | 8914308 | 3/1990 |
| DE | 29922088 | 4/2000 |

(Continued)

OTHER PUBLICATIONS

Advertisement for LinX HT™ Hamstring Tendon Polymer Fastener by Innovasive Devices, Inc.

(Continued)

*Primary Examiner* — Andrew Iwamaye
(74) *Attorney, Agent, or Firm* — McAndrews, Held & Malloy, Ltd.

(57) ABSTRACT

The present invention relates to a bone-tendon-bone graft and components. Embodiments of the present invention comprise an intermediate bone block that is used to adjustably secure soft tissue (e.g., tendon) in a patient. Embodiments of intermediate bone blocks of the present invention are used singly or in combination with one or more bone blocks to form a bone block assembly for securing soft tissue. The present invention further relates to an assembled bone-tendon-bone graft for implantation in humans comprising the intermediate bone block and a length of soft tissue. A bone-tendon-bone graft comprises a length of soft tissue extending from a first assembled bone block to a second bone block and then doubles back to said first assembled bone block. Depending upon the embodiment, the second bone block fixedly or slideably attaches to the length of soft tissue and facilitates it doubling back to the first assembled bone block.

32 Claims, 44 Drawing Sheets

U.S. PATENT DOCUMENTS

| | | | |
|---|---|---|---|
| D236,683 S | 9/1975 | Tegner et al. | |
| 4,034,444 A * | 7/1977 | Moertel | 24/394 |
| 4,349,921 A | 9/1982 | Kuntz | |
| 4,611,592 A * | 9/1986 | Talboy | 606/207 |
| 4,723,548 A | 2/1988 | Lalonde | |
| 4,744,793 A | 5/1988 | Parr et al. | |
| 4,772,286 A | 9/1988 | Goble et al. | |
| 4,781,183 A | 11/1988 | Casey et al. | |
| 4,828,562 A | 5/1989 | Kenna | |
| 4,911,710 A | 3/1990 | Milthorpe et al. | |
| 4,927,421 A | 5/1990 | Goble et al. | |
| 5,062,843 A | 11/1991 | Mahoney, III | |
| 5,067,962 A | 11/1991 | Campbell et al. | |
| 5,092,887 A | 3/1992 | Gendler | |
| 5,133,168 A | 7/1992 | Neilly et al. | |
| 5,139,520 A | 8/1992 | Rosenberg | |
| 5,147,400 A | 9/1992 | Kaplan et al. | |
| 5,171,326 A | 12/1992 | Ducheyne et al. | |
| RE34,293 E | 6/1993 | Goble et al. | |
| D336,683 S | 6/1993 | Inoue et al. | |
| 5,282,802 A | 2/1994 | Mahoney, III | |
| 5,320,115 A * | 6/1994 | Kenna | |
| 5,366,457 A | 11/1994 | McGuire et al. | |
| 5,370,662 A | 12/1994 | Stone et al. | |
| 5,383,878 A | 1/1995 | Roger et al. | |
| 5,391,169 A | 2/1995 | McGuire | |
| RE34,871 E | 3/1995 | McGuire et al. | |
| 5,397,356 A | 3/1995 | Goble et al. | |
| 5,397,357 A | 3/1995 | Schmieding et al. | |
| 5,425,733 A | 6/1995 | Schmieding | |
| 5,425,767 A | 6/1995 | Steininger et al. | |
| 5,443,509 A | 8/1995 | Boucher et al. | |
| 5,454,811 A | 10/1995 | Huebner | |
| 5,496,326 A | 3/1996 | Johnson | |
| 5,531,747 A | 7/1996 | Ray | |
| 5,556,428 A | 9/1996 | Shah | |
| 5,562,669 A | 10/1996 | McGuire | |
| 5,681,314 A | 10/1997 | Derouin et al. | |
| 5,713,897 A | 2/1998 | Goble et al. | |
| 5,733,289 A | 3/1998 | Seedhorn et al. | |
| 5,766,252 A | 6/1998 | Henry et al. | |
| 5,772,664 A | 6/1998 | DeSatnick et al. | |
| 5,800,544 A | 9/1998 | Demopulos et al. | |
| 5,846,484 A | 12/1998 | Scarborough | |
| 5,888,224 A | 3/1999 | Beckers et al. | |
| 5,895,425 A | 4/1999 | Grafton et al. | |
| 5,897,570 A | 4/1999 | Palleva et al. | |
| 5,902,015 A * | 5/1999 | Allcock | 297/463.1 |
| 5,951,560 A | 9/1999 | Simon et al. | |
| 5,961,520 A | 10/1999 | Beck et al. | |
| 5,968,046 A | 10/1999 | Castleman | |
| 6,001,100 A | 12/1999 | Sherman et al. | |
| 6,019,792 A | 2/2000 | Cauthen | |
| 6,025,538 A * | 2/2000 | Yaccarino, III | 128/898 |
| D426,148 S | 6/2000 | Markarian | |
| 6,080,158 A | 6/2000 | Lin | |
| 6,080,192 A | 6/2000 | Demopulos et al. | |
| 6,090,998 A | 7/2000 | Grooms et al. | |
| 6,106,556 A | 8/2000 | Demopulos et al. | |
| 6,110,210 A | 8/2000 | Norton et al. | |
| 6,123,731 A | 9/2000 | Boyce et al. | |
| 6,129,762 A | 10/2000 | Li | |
| 6,179,874 B1 | 1/2001 | Cauthen | |
| 6,190,412 B1 | 2/2001 | Lee et al. | |
| 6,200,347 B1 * | 3/2001 | Anderson et al. | 623/16.11 |
| 6,270,528 B1 | 8/2001 | McKay | |
| 6,287,309 B1 | 9/2001 | Baccelli et al. | |
| 6,327,753 B1 | 12/2001 | Rushing | |
| 6,368,325 B1 | 4/2002 | McKinley et al. | |
| D463,559 S | 9/2002 | Bryant et al. | |
| 6,454,770 B1 | 9/2002 | Klaue | |
| 6,482,584 B1 | 11/2002 | Mills et al. | |
| 6,497,726 B1 | 12/2002 | Carter et al. | |
| D471,085 S | 3/2003 | Markarian | |
| 6,579,295 B1 | 6/2003 | Supinski et al. | |
| 6,592,622 B1 | 7/2003 | Ferguson | |
| D479,331 S | 9/2003 | Pike et al. | |
| 6,613,278 B1 | 9/2003 | Mills | |
| 6,632,247 B2 * | 10/2003 | Boyer, II et al. | 623/23.6 |
| 6,652,592 B1 | 11/2003 | Grooms et al. | |
| 6,652,818 B1 | 11/2003 | Mills et al. | |
| 6,679,889 B1 | 1/2004 | West, Jr. et al. | |
| 6,730,124 B2 | 5/2004 | Steiner | |
| 6,761,739 B2 | 7/2004 | Shepard | |
| 6,805,713 B1 | 10/2004 | Carter et al. | |
| 6,857,874 B2 | 2/2005 | Kim | |
| 6,890,354 B2 | 5/2005 | Steiner et al. | |
| 6,893,462 B2 | 5/2005 | Buskirk et al. | |
| 7,011,684 B2 | 3/2006 | Eckman | |
| 7,063,725 B2 | 6/2006 | Foley | |
| 7,141,066 B2 | 11/2006 | Steiner et al. | |
| D533,277 S | 12/2006 | Blain | |
| 7,169,183 B2 | 1/2007 | Liu et al. | |
| D536,453 S | 2/2007 | Young et al. | |
| 7,217,293 B2 | 5/2007 | Branch, Jr. | |
| D552,734 S | 10/2007 | Eckman | |
| D553,745 S | 10/2007 | Park | |
| 7,323,011 B2 | 1/2008 | Shepard et al. | |
| 7,351,262 B2 * | 4/2008 | Bindseil et al. | 623/17.16 |
| D583,053 S | 12/2008 | Zhukauskas et al. | |
| D583,054 S | 12/2008 | Zhukauskas et al. | |
| D583,055 S | 12/2008 | Lewis et al. | |
| D583,056 S | 12/2008 | Goede et al. | |
| D583,473 S | 12/2008 | Goede et al. | |
| D604,850 S | 11/2009 | Lewis et al. | |
| D605,768 S | 12/2009 | Zhukauskas et al. | |
| 2001/0031254 A1 * | 10/2001 | Bianchi et al. | 424/93.7 |
| 2002/0029084 A1 * | 3/2002 | Paul et al. | 623/23.63 |
| 2002/0072806 A1 * | 6/2002 | Buskirk et al. | 623/23.51 |
| 2003/0023304 A1 | 1/2003 | Carter et al. | |
| 2003/0130735 A1 | 7/2003 | Rogalski | |
| 2003/0171810 A1 * | 9/2003 | Steiner | 623/13.14 |
| 2003/0171811 A1 | 9/2003 | Steiner et al. | |
| 2003/0229394 A1 | 12/2003 | Ogle et al. | |
| 2004/0030385 A1 | 2/2004 | Steiner | |
| 2004/0102780 A1 | 5/2004 | West, Jr. | |
| 2004/0210308 A1 | 10/2004 | Carter et al. | |
| 2005/0015940 A1 | 1/2005 | Stafford | |
| 2005/0059987 A1 * | 3/2005 | Hermann et al. | 606/157 |
| 2005/0152881 A1 | 7/2005 | Mills et al. | |
| 2005/0159812 A1 * | 7/2005 | Dinger et al. | 623/13.14 |
| 2005/0228378 A1 * | 10/2005 | Kalfas et al. | 606/61 |
| 2005/0229323 A1 | 10/2005 | Mills et al. | |
| 2007/0162124 A1 | 7/2007 | Whittaker | |

FOREIGN PATENT DOCUMENTS

| | | |
|---|---|---|
| EP | 1797845 | 6/2007 |
| FR | 2683715 | 5/1993 |
| WO | 02/064180 | 8/2002 |

OTHER PUBLICATIONS

Non-Final Rejection corresponding to U.S. Appl. No. 11/073,400 mailed Sep. 8, 2008.

Non-Final Rejection corresponding to U.S. Appl. No. 11/073,281 mailed Aug. 5, 2008.

Advertisement for LinX HT.TM. Hamstring Polymer Fastener by Innovasive Devices, Inc, 1997.

D. T. Cheung, N. Perelman, E. C. Ko, M. Nimni, "Mechanism of Crosslinking of Proteins by Glutaraldehyde III. Reaction with Collagen in Tissues", Connective Tissue Research, (1985), vol. 13, pp. 109-115, Gordon and Breach, Science Publishers, Inc. and OPA Ltd.

E. Oberg, F. Jones, H. L. Horton, H. H. Ryffel, "Machinery's Handbook", 24th Edition, pp. 1616-1617; 1628-1633; 1652-1653; 1656-1657; 1992 by Industrial Press, Inc., New York, New York.

European Search Report for European Patent Application No. 06736865.4-1526, mailed Dec. 29, 2009.

Examiner's Answer corresponding to U.S. Appl. No. 11/313,280, dated Oct. 26, 2009.

Final Rejection corresponding to U.S. Appl. No. 11/073,400, dated Apr. 3, 2009.

Final Rejection corresponding to U.S. Appl. No. 11/073,202, dated Sep. 24, 2009.

Final Rejection corresponding to U.S. Appl. No. 11/073,281, dated Sep. 24, 2009.

Final Rejection corresponding to U.S. Appl. No. 11/313,280 dated Mar. 27, 2009.
H. Boszotta, M. D., "Arthroscopic Reconstruction of Anterior Cruciate Ligament Using BTYB Patellar Ligament in the Press-Fit Technique", Surg. Technol. Int. 11:249-253 (2003).
H. H. Paessler, MD., D. S. Mastrokalos, M.D., "Anterior Cruciate Ligament Reconstruction Using Semitendinosus and Gracilis Tendons, Bone Patellar Tendon, or Quadriceps Tendon-Graft with Press-Fit Fixation Without Hardware. A New and Innovative Procedure", Orthop. Clin. North Am.; 34 (1): 49-64 (Jan. 2003).
International Search Report corresponding to International Application No. PCT/US2006/007614, mailed Apr. 22, 2008, 3 pages.
International Search Report corresponding to International Application No. PCT/US2007/09218, mailed Feb. 21, 2008, 5 pages.
Interview Summary corresponding to U.S. Appl. No. 11/073,202, dated Jan. 14, 2010.
Interview Summary corresponding to U.S. Appl. No. 11/073,202, dated Feb. 17, 2010.
Interview Summary corresponding to U.S. Appl. No. 11/073,202, dated Feb. 18, 2010.
Interview Summary corresponding to U.S. Appl. No. 11/073,281, dated Jan. 14, 2010.
Interview Summary corresponding to U.S. Appl. No. 11/073,281, dated Feb. 17, 2010.
Interview Summary corresponding to U.S. Appl. No. 11/073,281, dated Feb. 18, 2010.
Interview Summary Corresponding to U.S. Appl. No. 11/313,280, dated Jul. 24, 2009.
Interview Summary corresponding to U.S. Appl. No. 11/428,213, dated Nov. 23, 2009.
Interview Summary corresponding to U.S. Appl. No. 11/428,213, dated Nov. 27, 2009.
Interview Summary corresponding to U.S. Appl. No. 11/428,213, dated Dec. 16, 2009.
Interview Summary corresponding to U.S. Appl. No. 11/428,213, dated Jan. 11, 2010.
Interview Summary corresponding to U.S. Appl. No. 11/428,213, dated Jan. 14, 2010.
J. Dargel, R. Schmidt-Wiethoff, T. Schneider, Gert-Peter Bruggemann, J. Koebke, "Biomechanical Testing of Quadriceps Tendon-Patellar Bone Grafts: An Alternative Graft Source for Press-Fit Anterior Cruciate Ligament Reconstruction?", Arch Orthop Trauma Surg (2006) 126: 265-270.
J. P. Van Kleunen, D. Elliott, "Effect of a Natural Crosslinking Agent (Genipin) on Tendon Longitudinal and Transverse Tensile Properties", 2003 Summer Bioengineering Conference, Jun. 25-29, Sonesta Beach Resort in Key Biscayne, Florida.
Non-Final Rejection corresponding to U.S. Appl. No. 11/073,202, dated Mar. 13, 2009.
Non-Final Rejection corresponding to U.S. Appl. No. 11/073,202, mailed Aug. 5, 2008.
Non-Final Rejection corresponding to U.S. Appl. No. 11/073,281, dated Mar. 27, 2009.
Non-Final Rejection corresponding to U.S. Appl. No. 11/073,281, mailed Aug. 5, 2008.
Non-Final Rejection corresponding to U.S. Appl. No. 11/073,400, dated Jun. 11, 2009.
Non-Final Rejection corresponding to U.S. Appl. No. 11/073,400, mailed Sep. 8, 2008.
Non-Final Rejection corresponding to U.S. Appl. No. 11/313,280, mailed Sep. 30, 2008.
Non-Final Rejection corresponding to U.S. Appl. No. 11/428,213, dated Oct. 29, 2008.
Non-Final Rejection corresponding to U.S. Appl. No. 11/428,213, dated May 28, 2009.
R. Schmidt-Wiethoff, J. Dargel, M. Gerstner, T. Schneider, J. Koebke, "Bone Plug Length and Loading Angle Determine the Primary Stability of Patellar Tendon-Bone Grafts in Press-Fit ACL Reconstruction", Knee Surg. Sports Traumatol. Arthrosc (2006) 14: 108-111.
S.M. Schlicht and W.A. Morrison, "The Plantaris Tendon As a Tendo-Osseous Graft. Part I. An Anatomical Study", J. Hand Surg. [BR]; 17 (4): 471-5 (Aug. 1992).
W. A. Morrison and S.M. Schlicht, "The Plantaris Tendon As a Tendo-Osseous Graft. Part II. Clinical Studies" J. Hand Surg. [BR]; 17 (4): 467-70 (Aug. 1992).
Written Opinion of the International Searching Authority corresponding to International Application Serial No. PCT/US2006/007614, mailed Apr. 22, 2008, 5 pages.
Written Opinion of the International Searching Authority corresponding to International Application No. PCT/US2007/09218, mailed Feb. 21, 2008, 5 pages.

\* cited by examiner

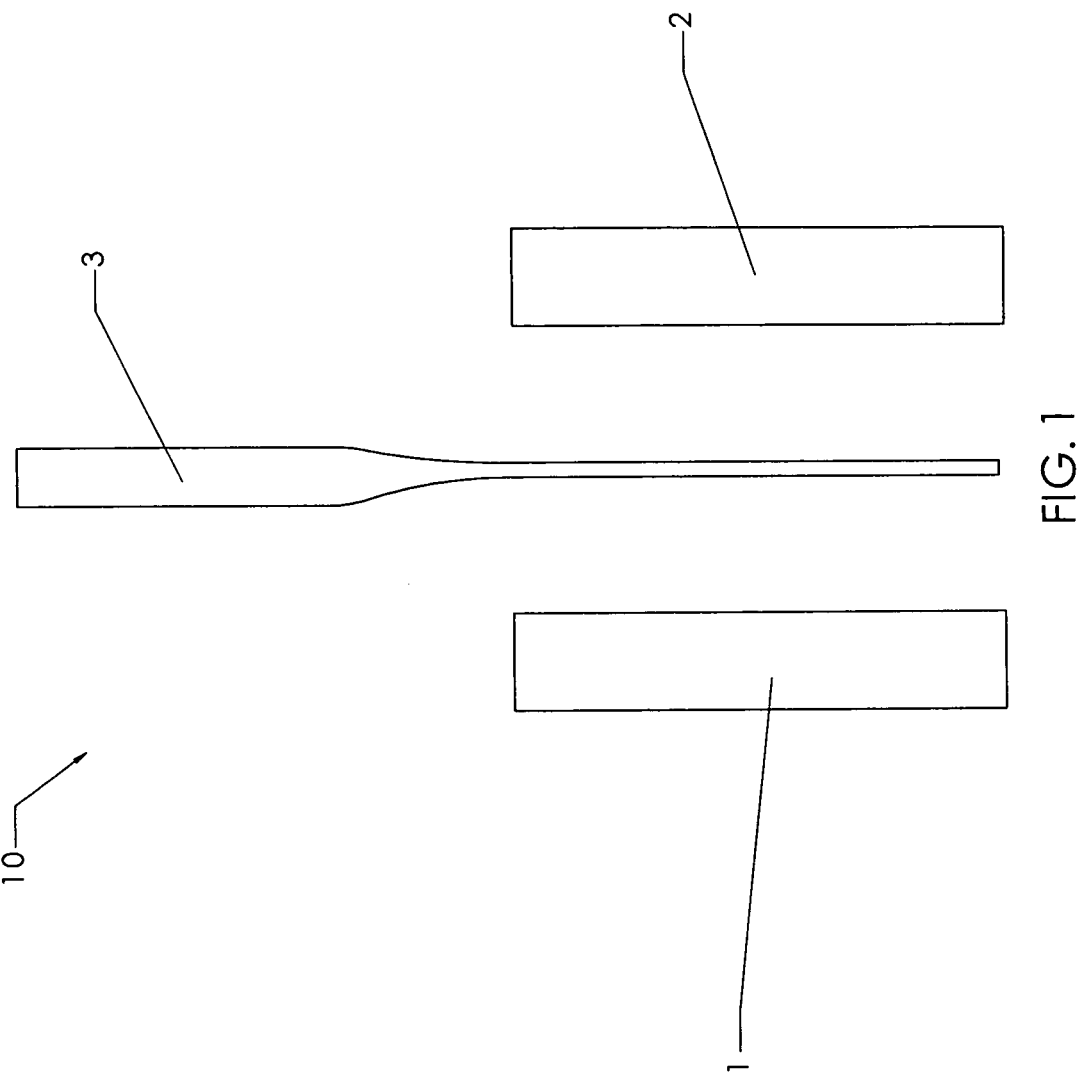

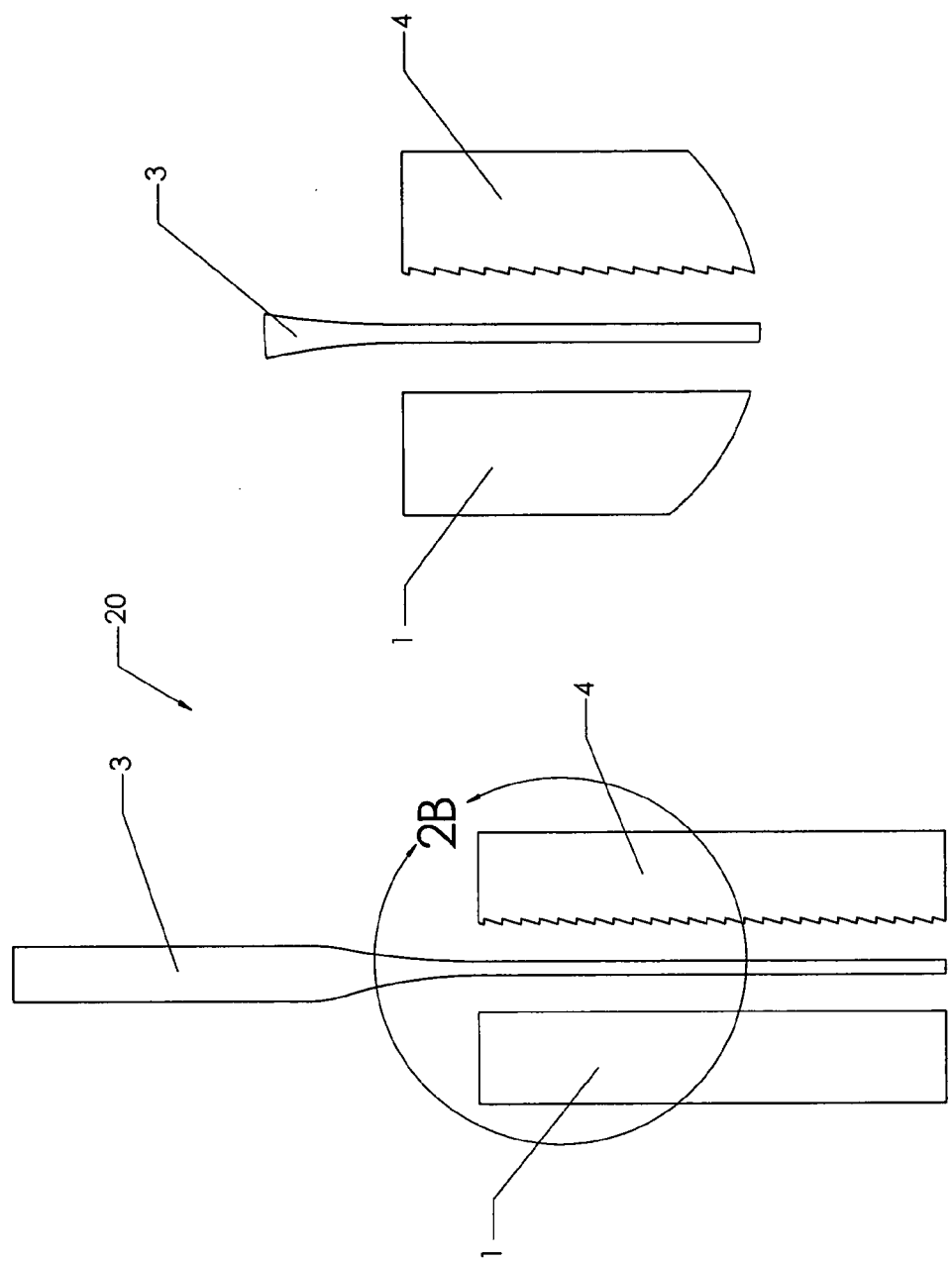

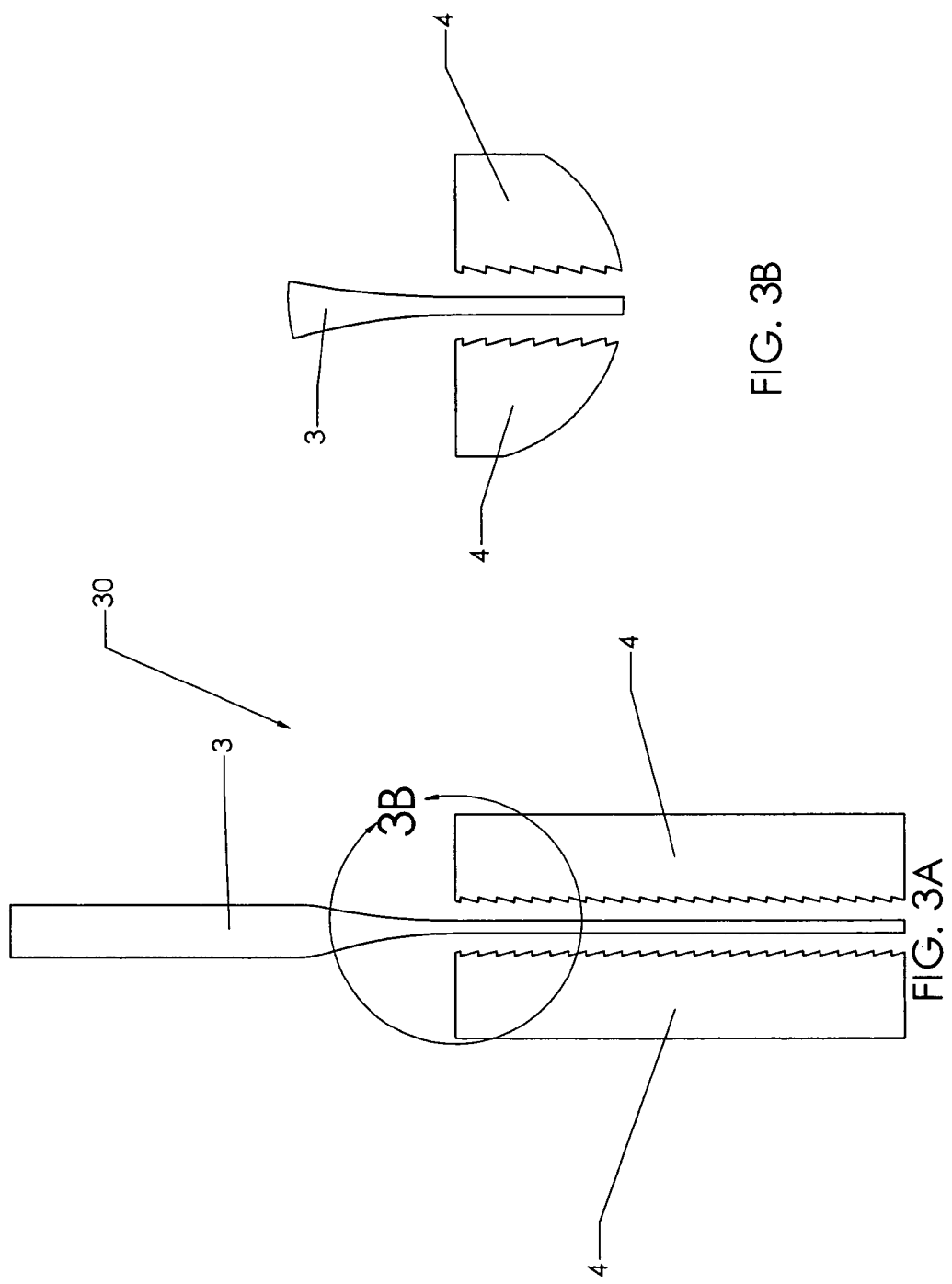

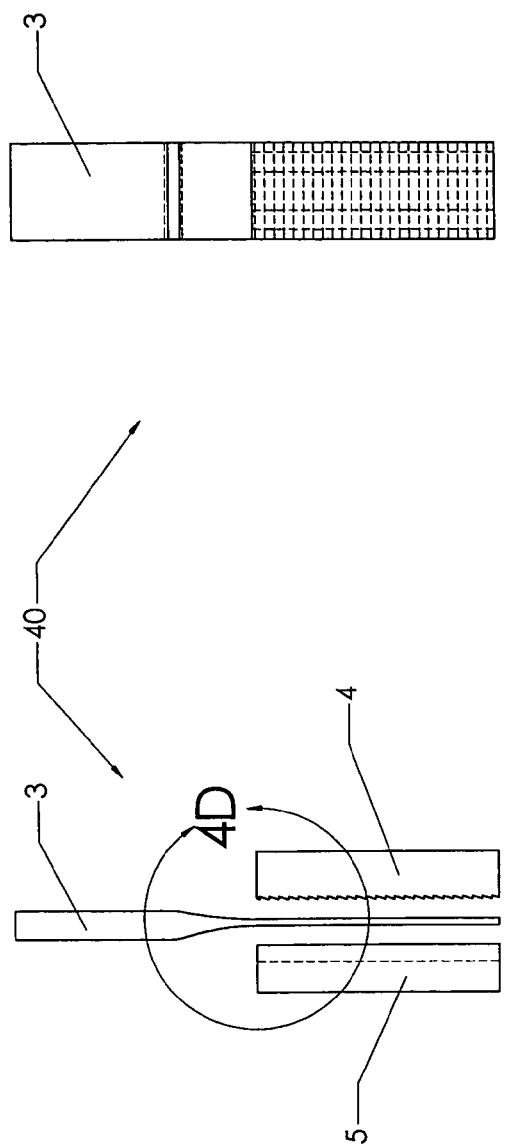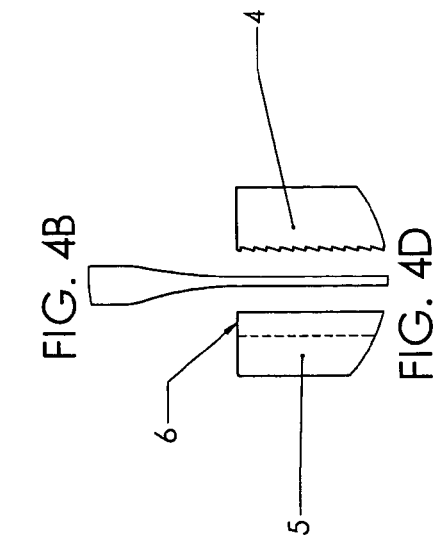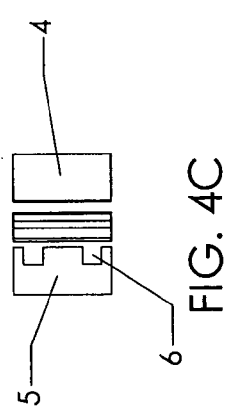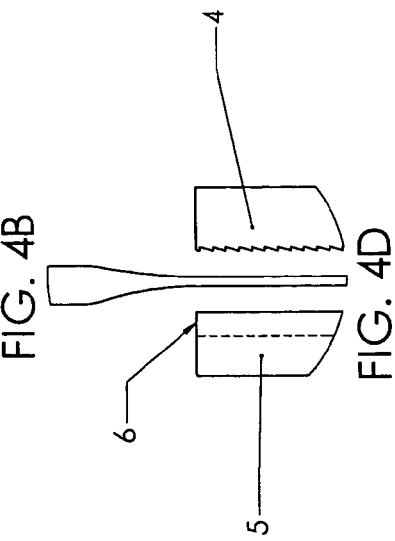
FIG. 4A
FIG. 4B
FIG. 4C
FIG. 4D

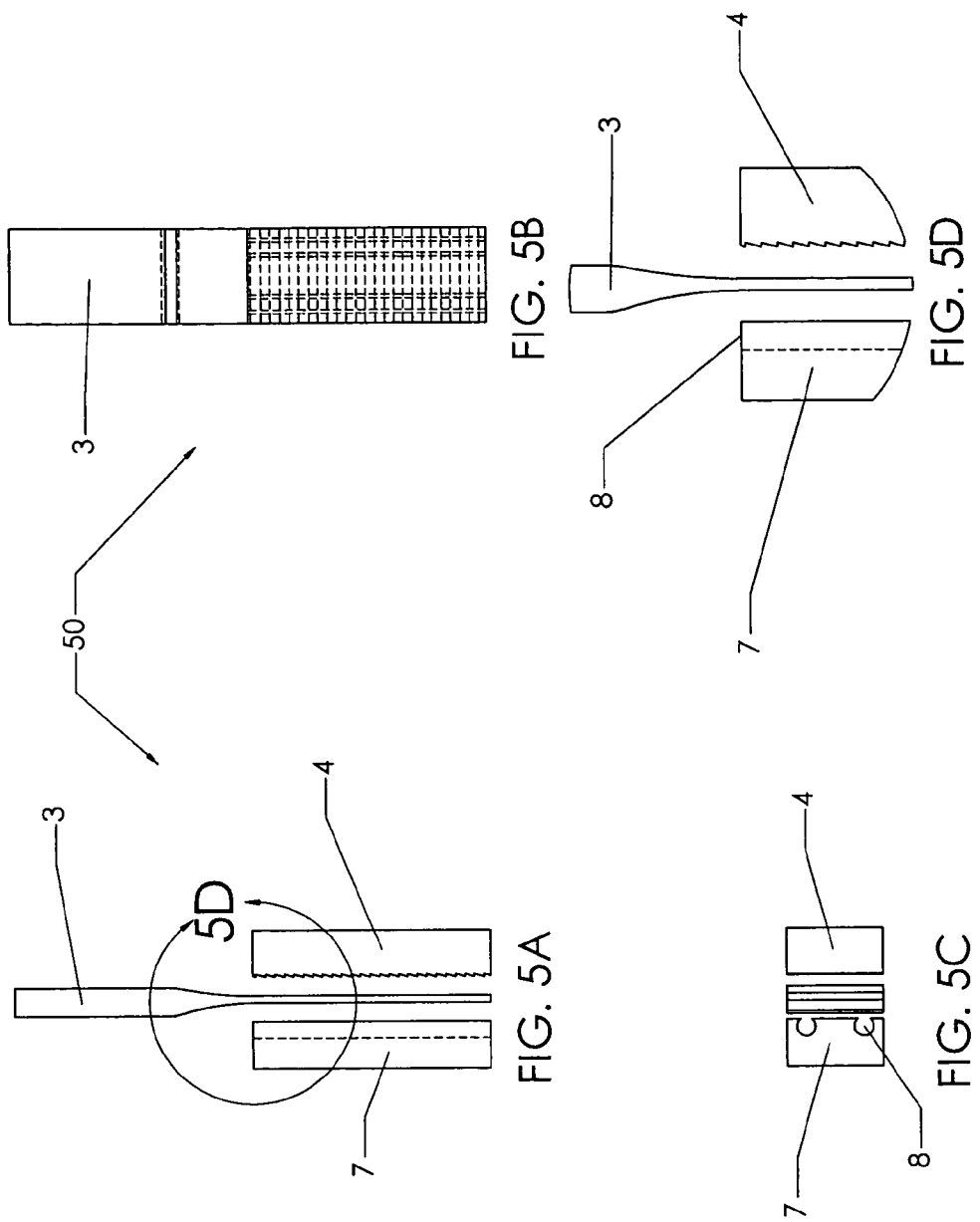

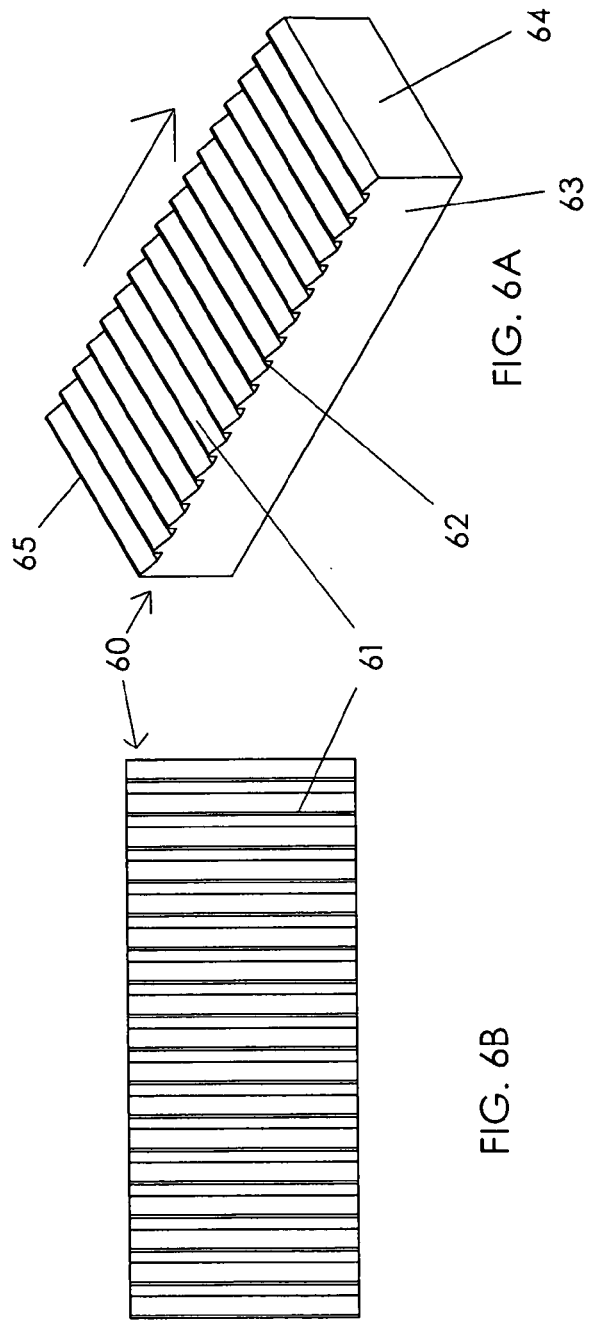
FIG. 6A
FIG. 6B
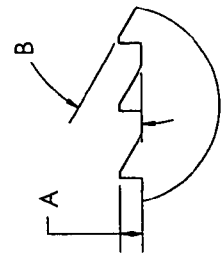
FIG. 6D
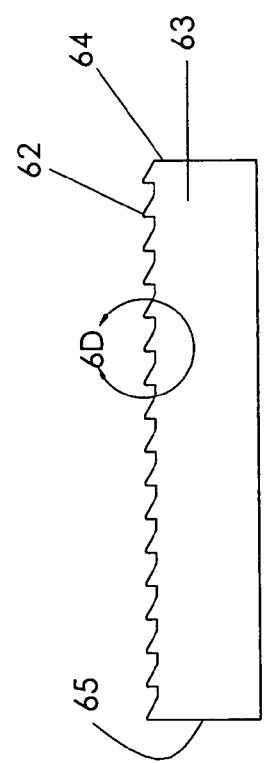
FIG. 6C

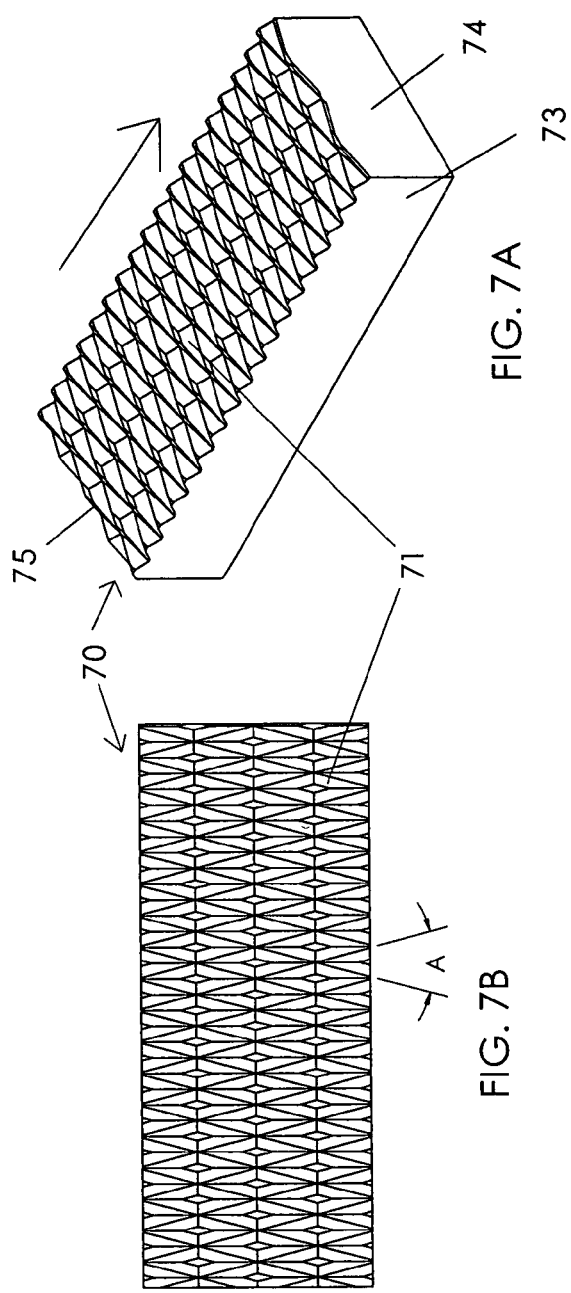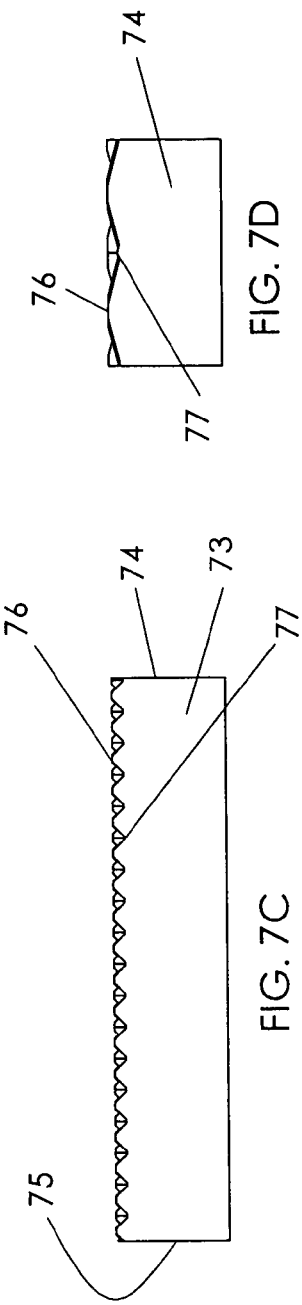
FIG. 7A
FIG. 7B
FIG. 7C
FIG. 7D

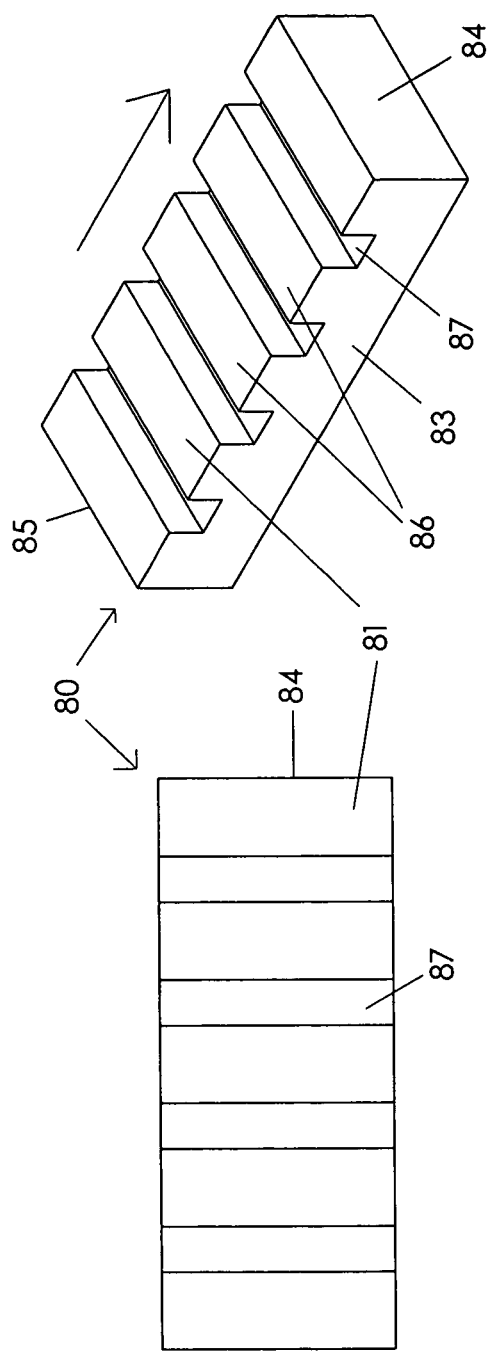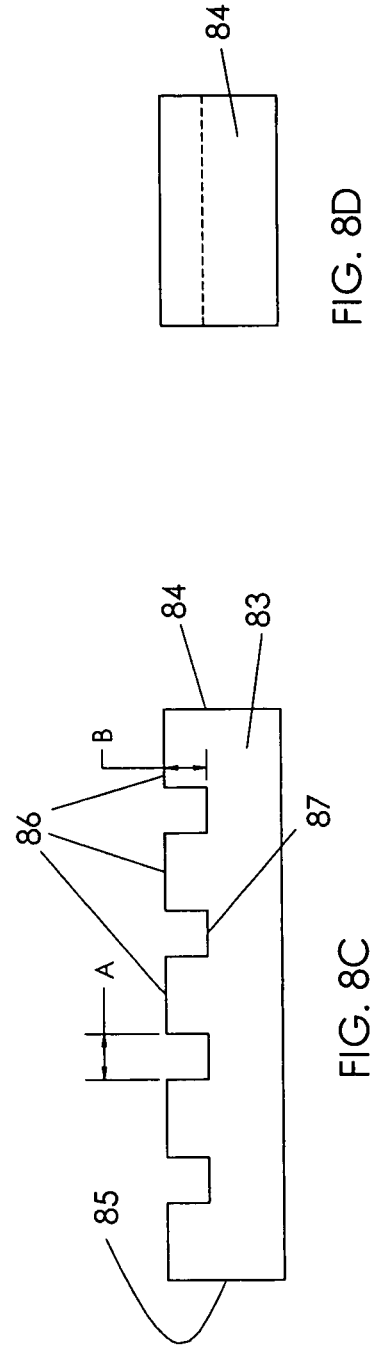

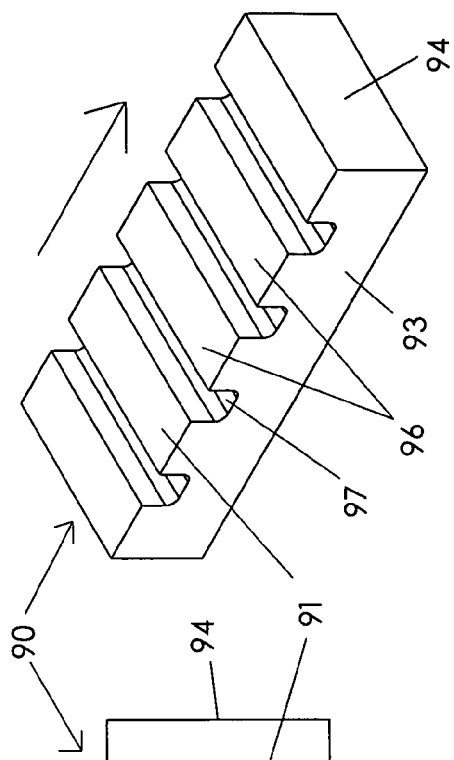
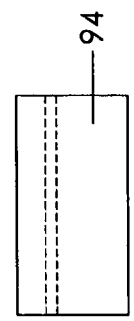
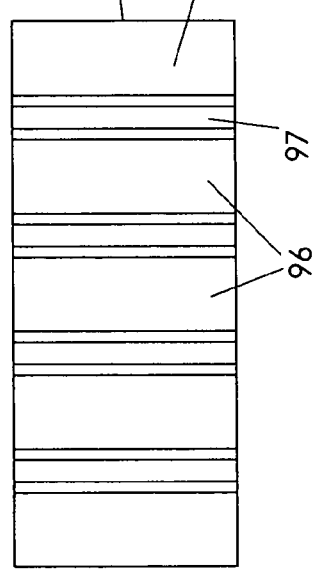
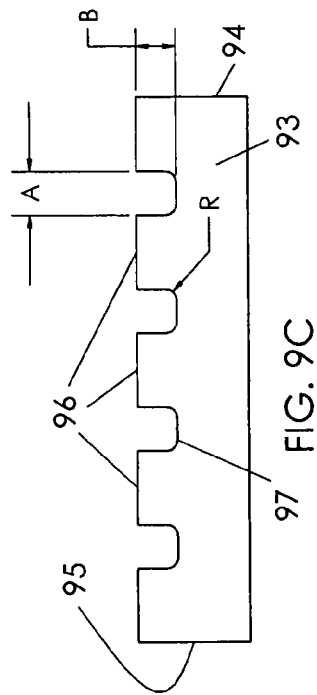

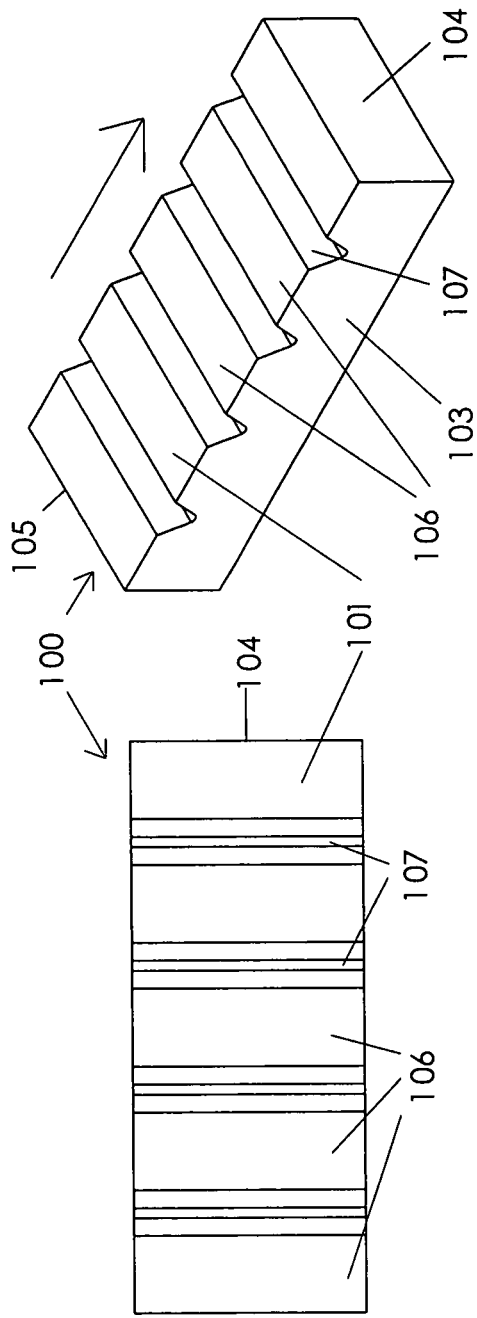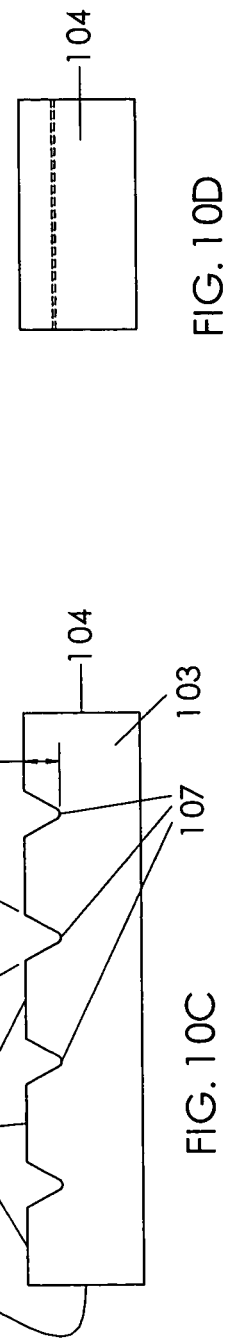

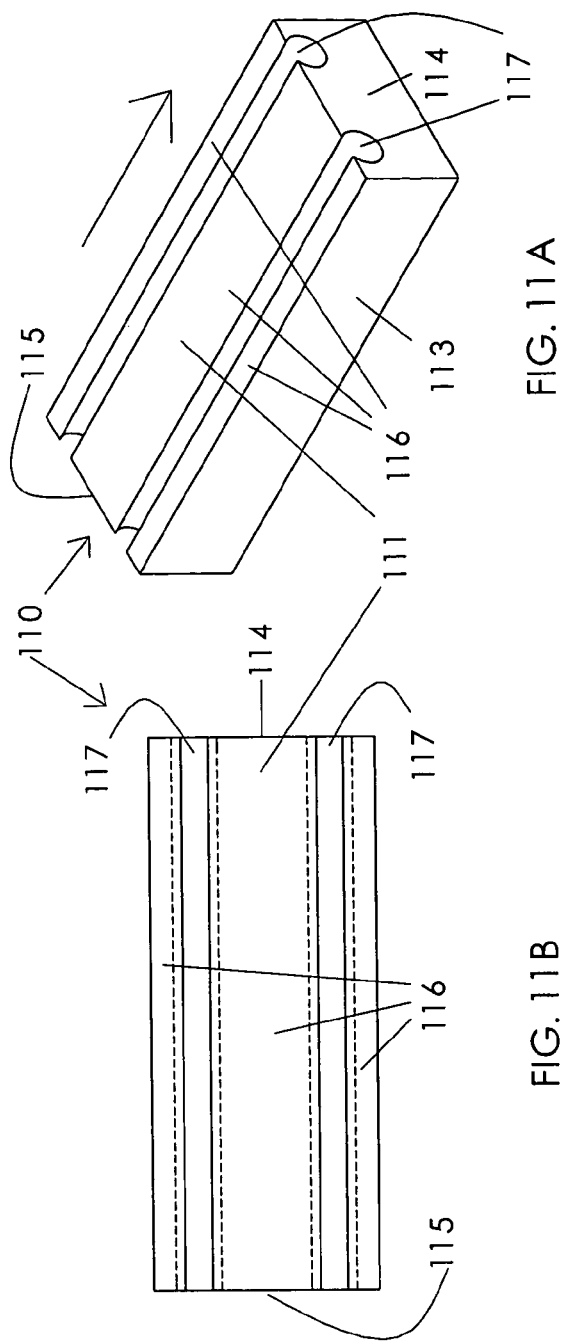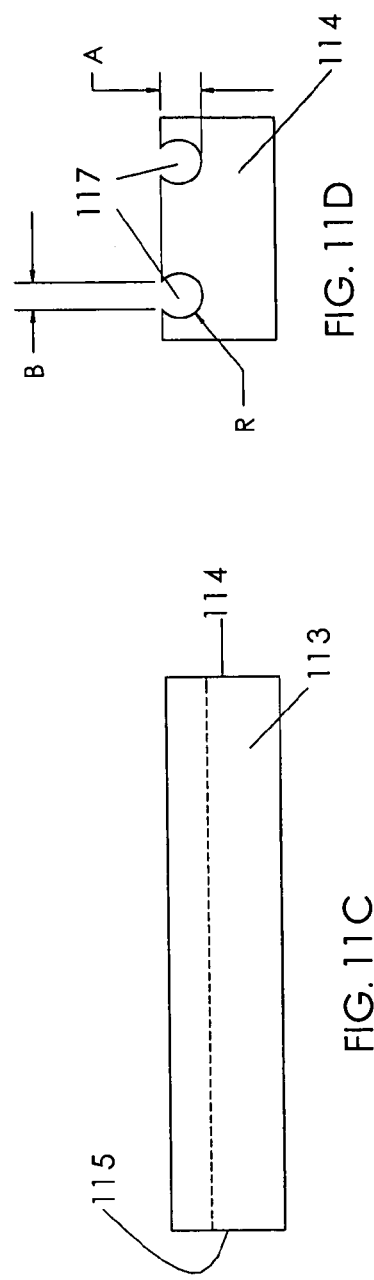
FIG. 11A
FIG. 11B
FIG. 11C
FIG. 11D

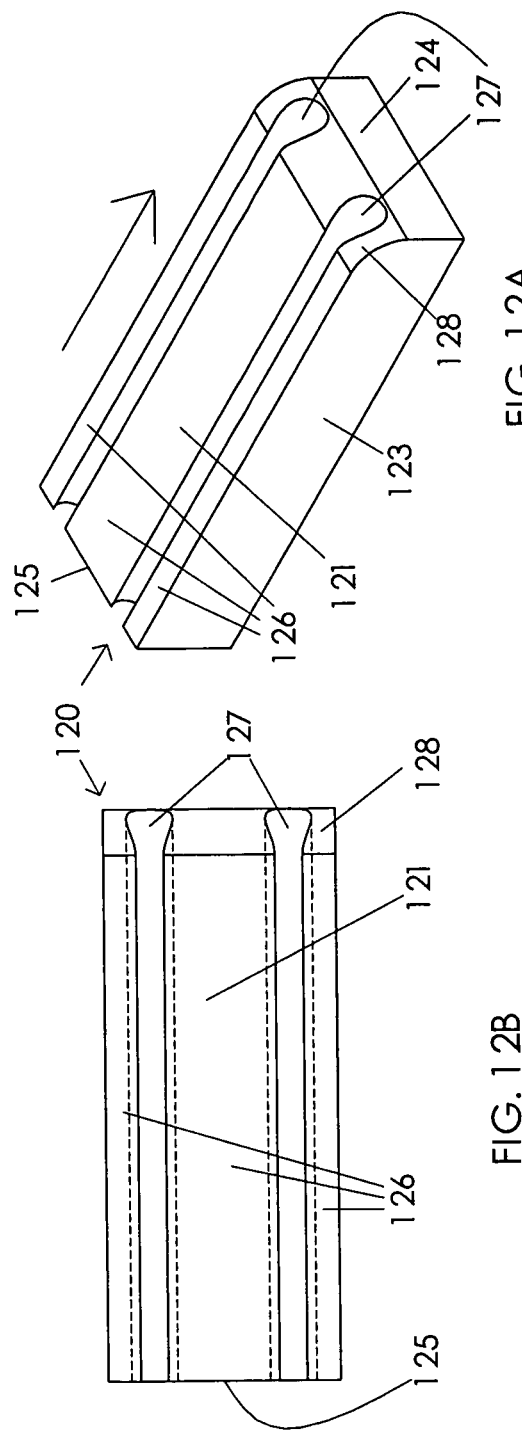
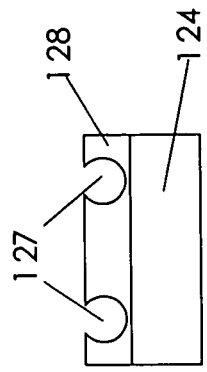
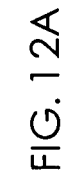
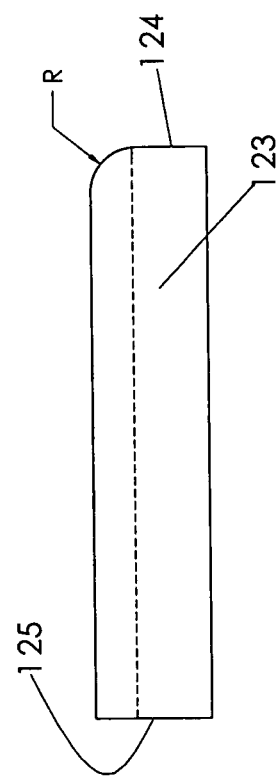
FIG. 12A
FIG. 12B
FIG. 12C
FIG. 12D

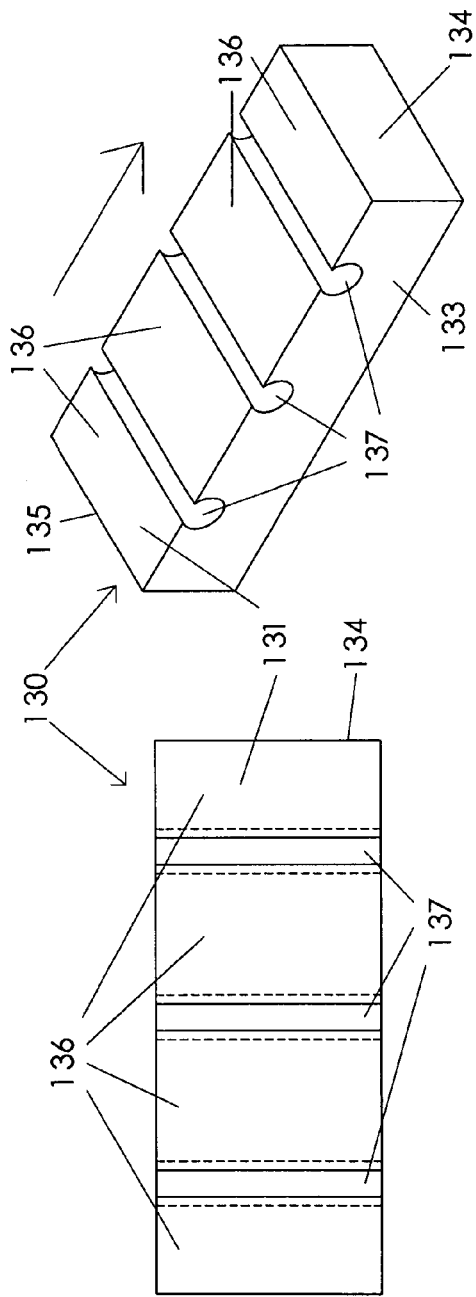
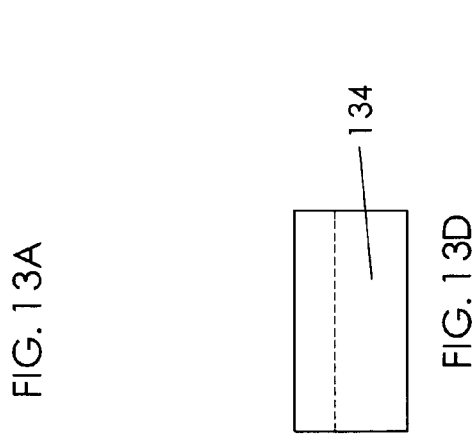
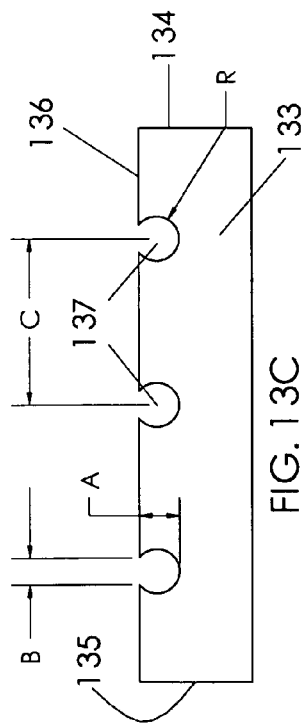
FIG. 13A
FIG. 13D
FIG. 13B
FIG. 13C

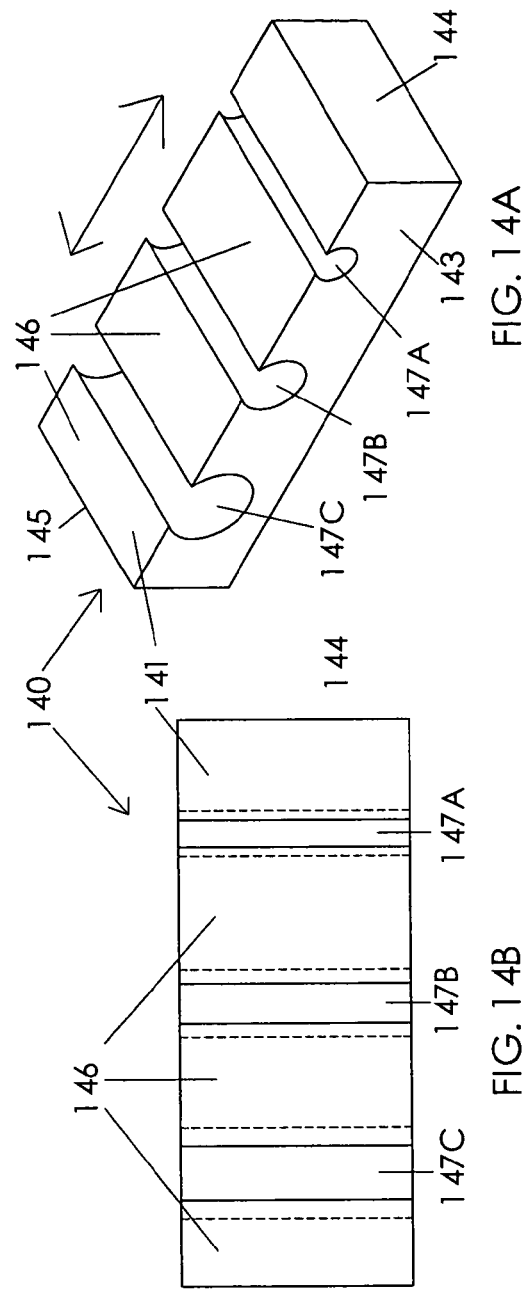
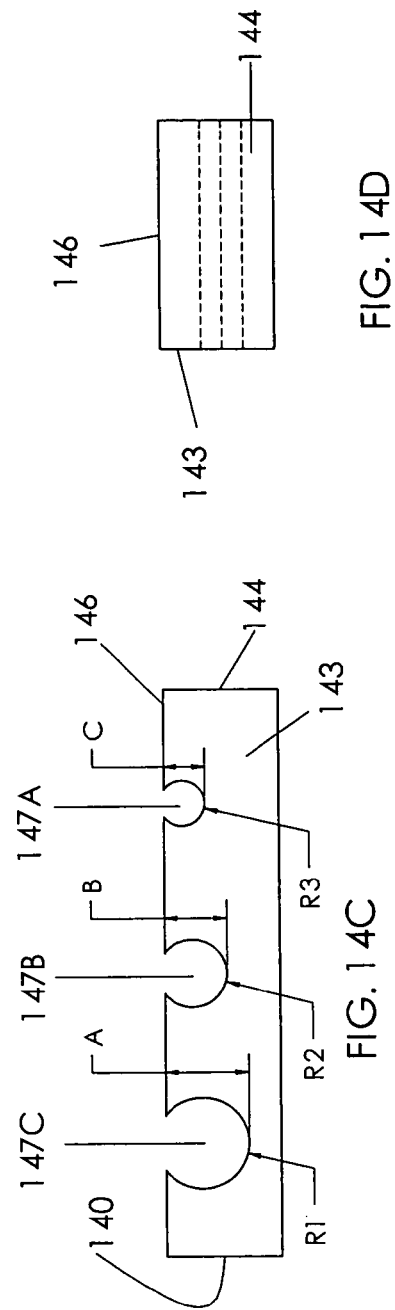
FIG. 14A
FIG. 14B
FIG. 14C
FIG. 14D

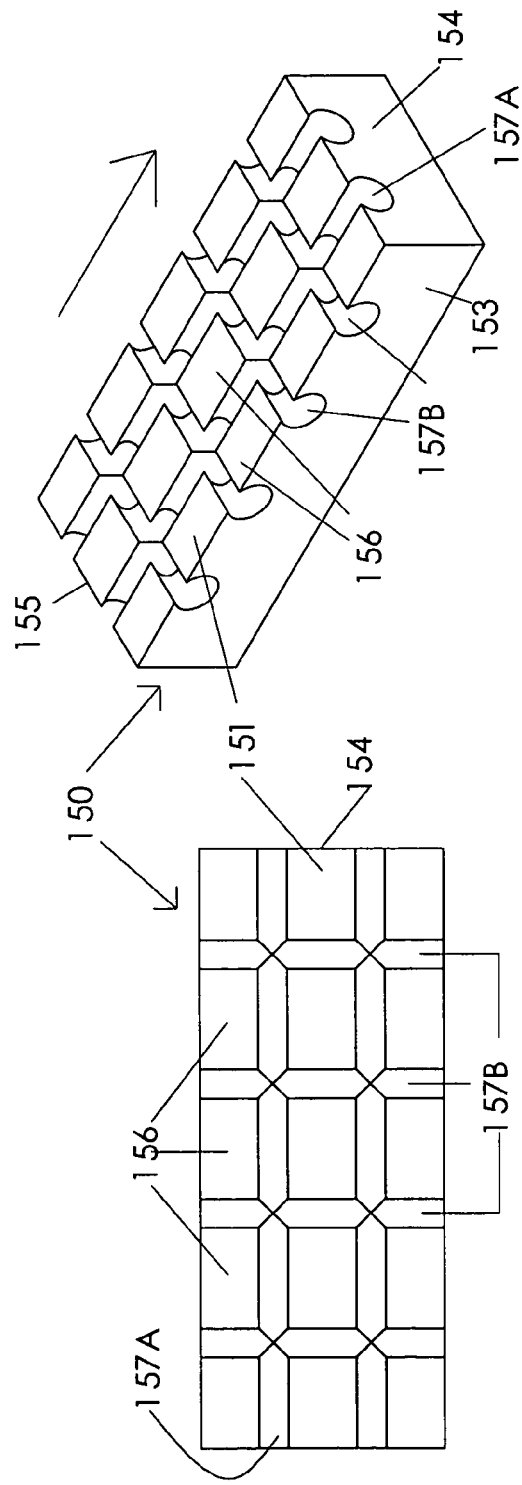
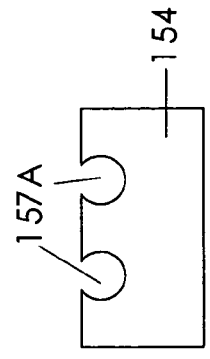
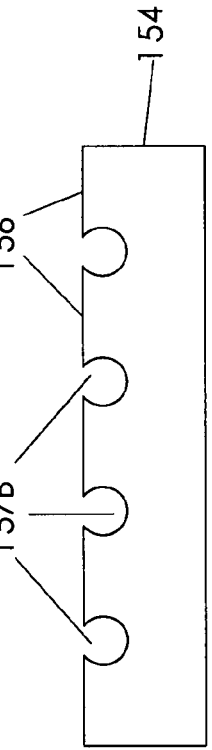
FIG. 15A
FIG. 15B
FIG. 15C
FIG. 15D

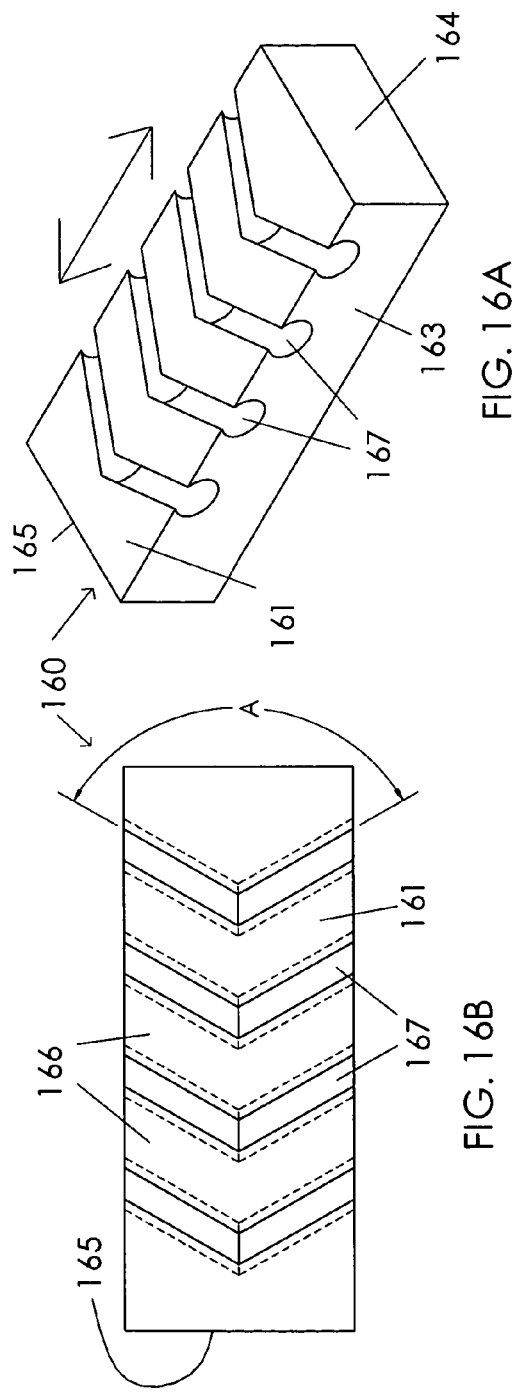
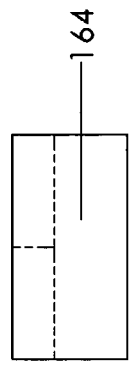
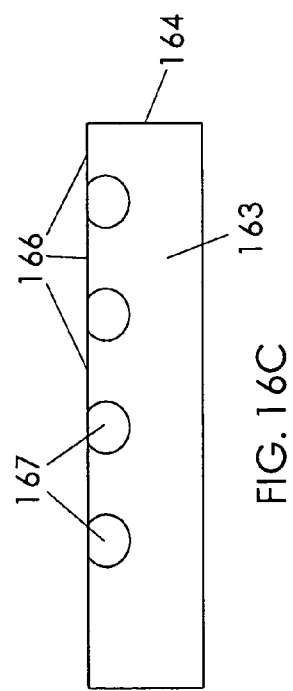
FIG. 16A
FIG. 16B
FIG. 16C
FIG. 16D

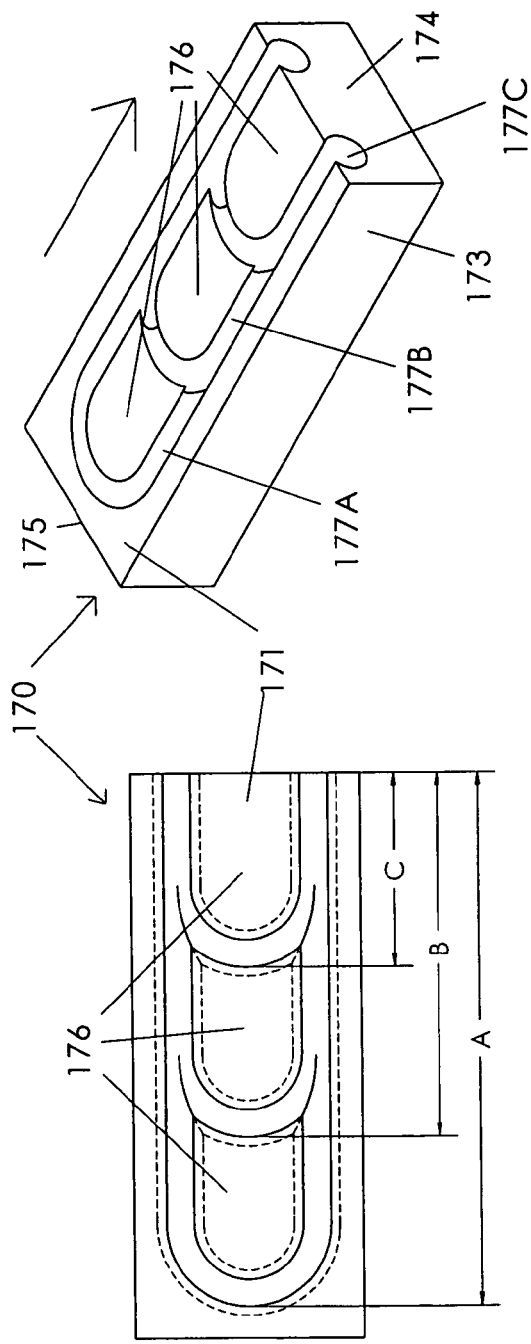
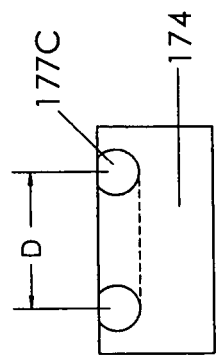
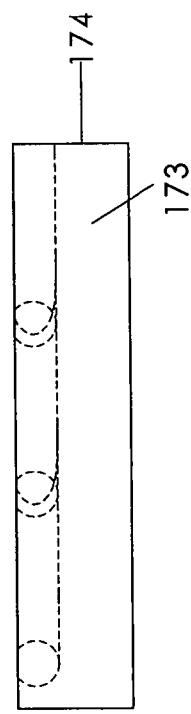
FIG. 17A
FIG. 17B
FIG. 17C
FIG. 17D

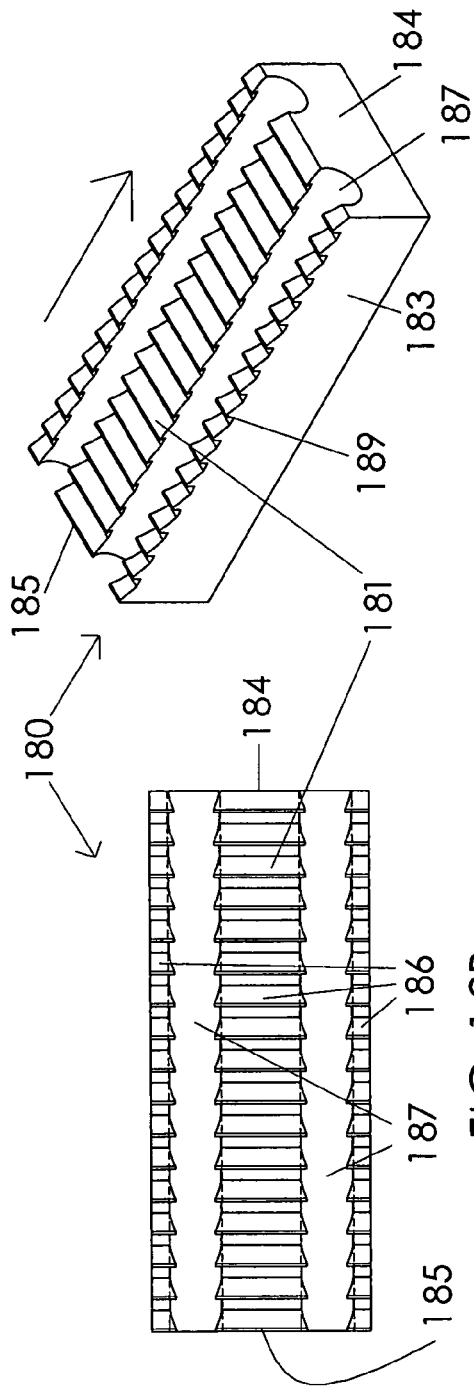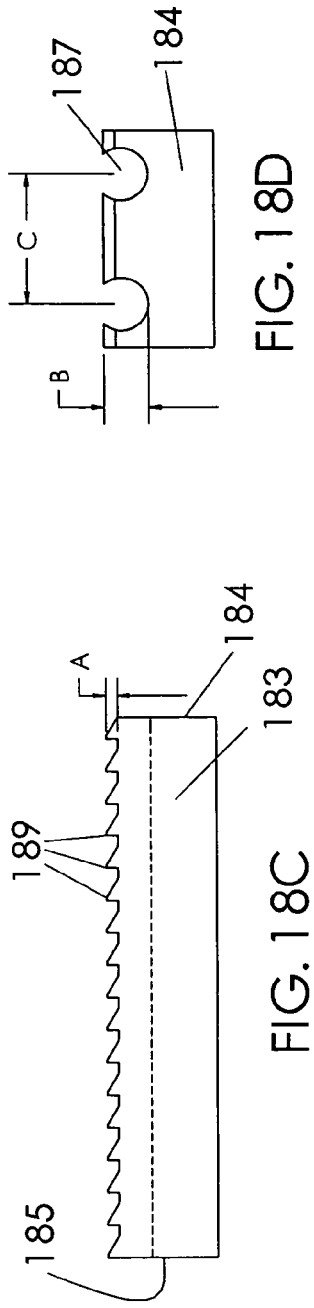

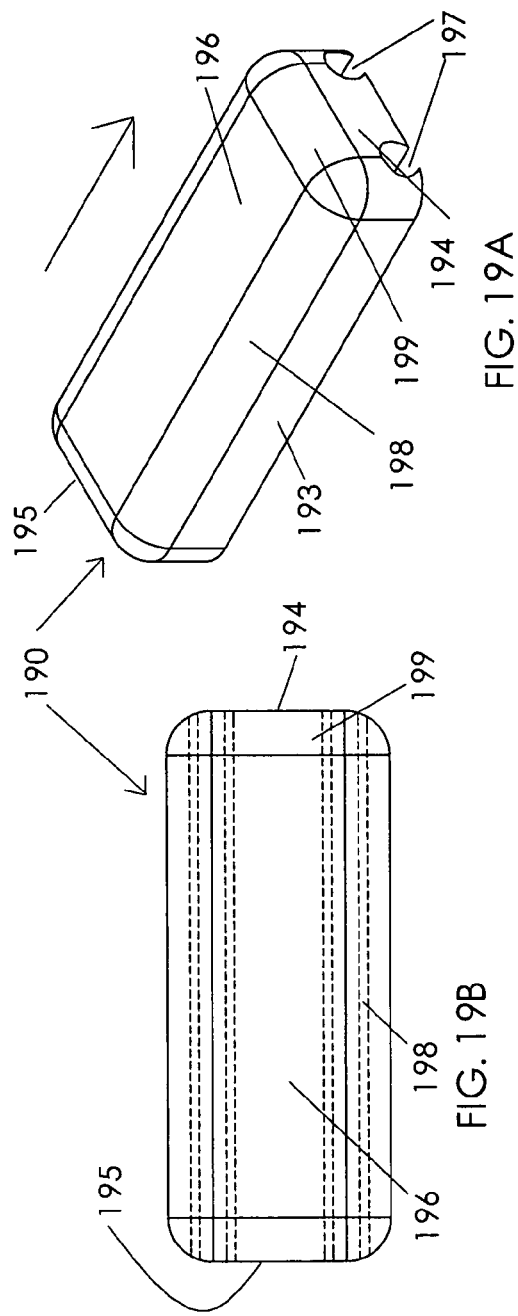
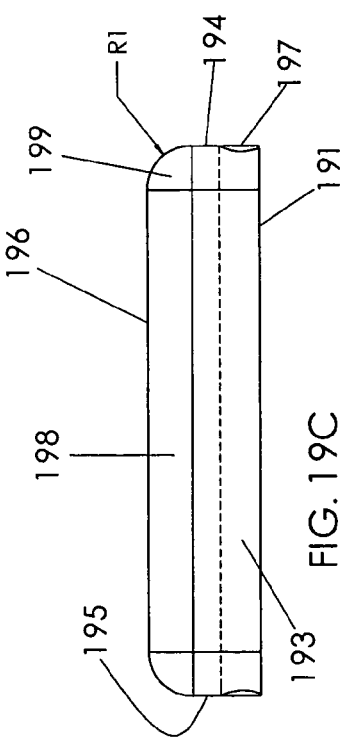
FIG. 19A
FIG. 19B
FIG. 19C
FIG. 19D

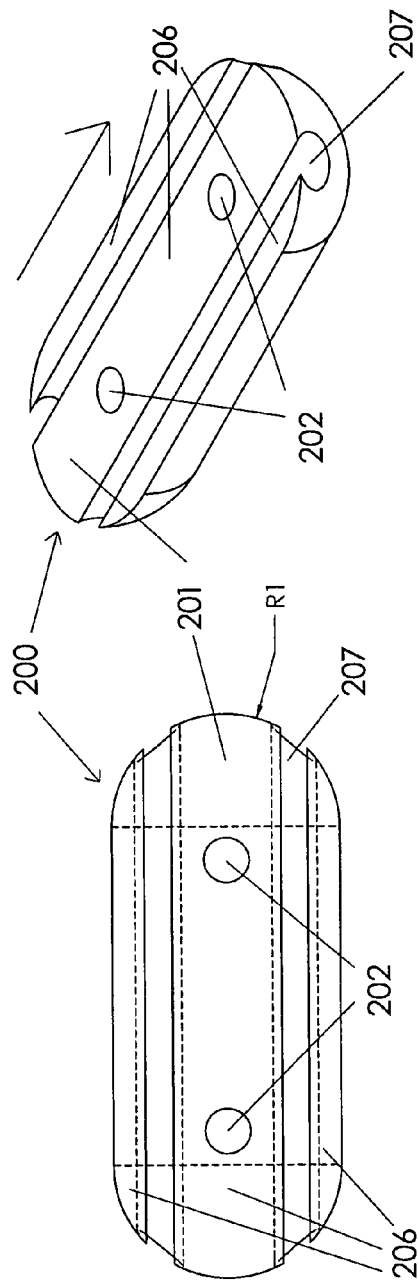
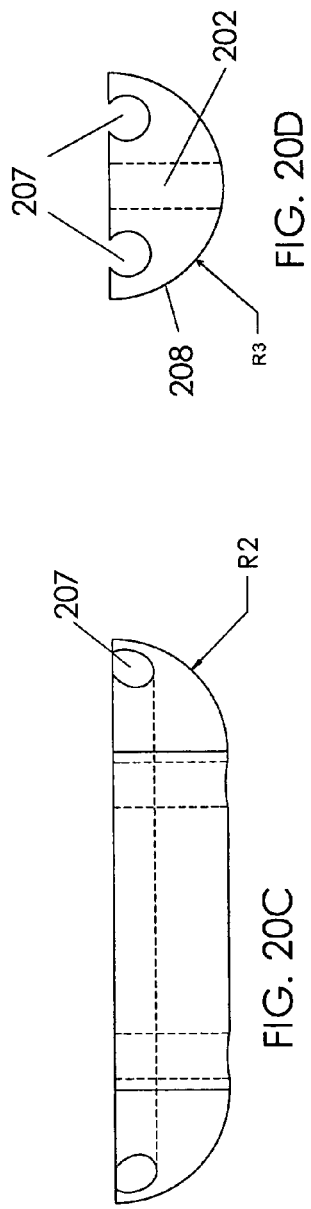
FIG. 20A
FIG. 20B
FIG. 20C
FIG. 20D

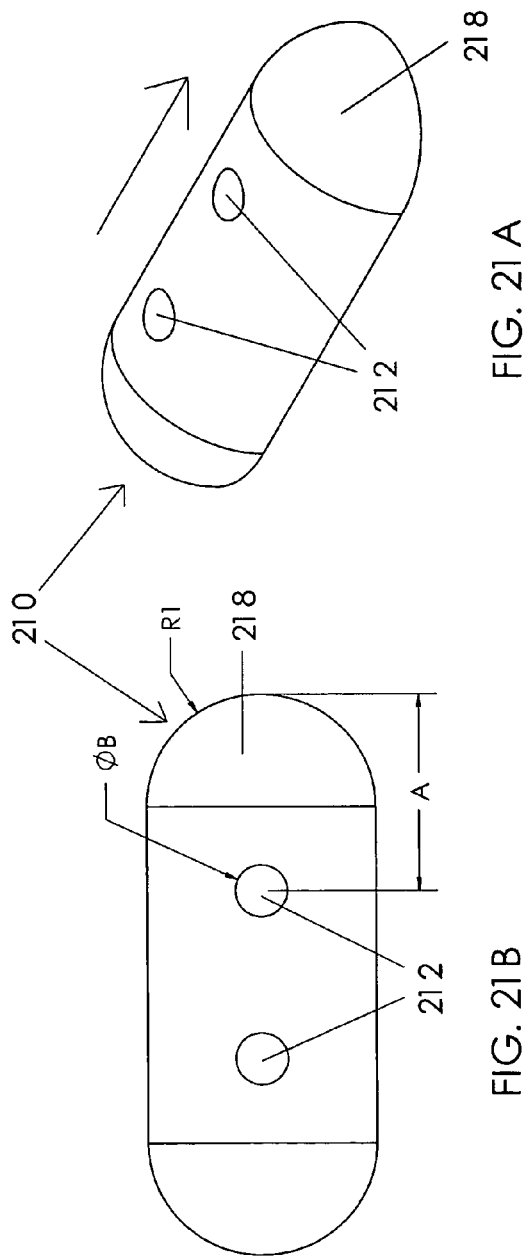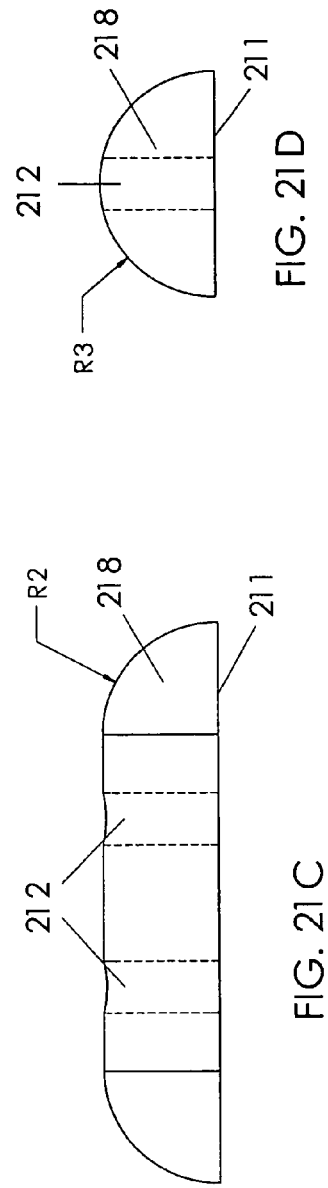

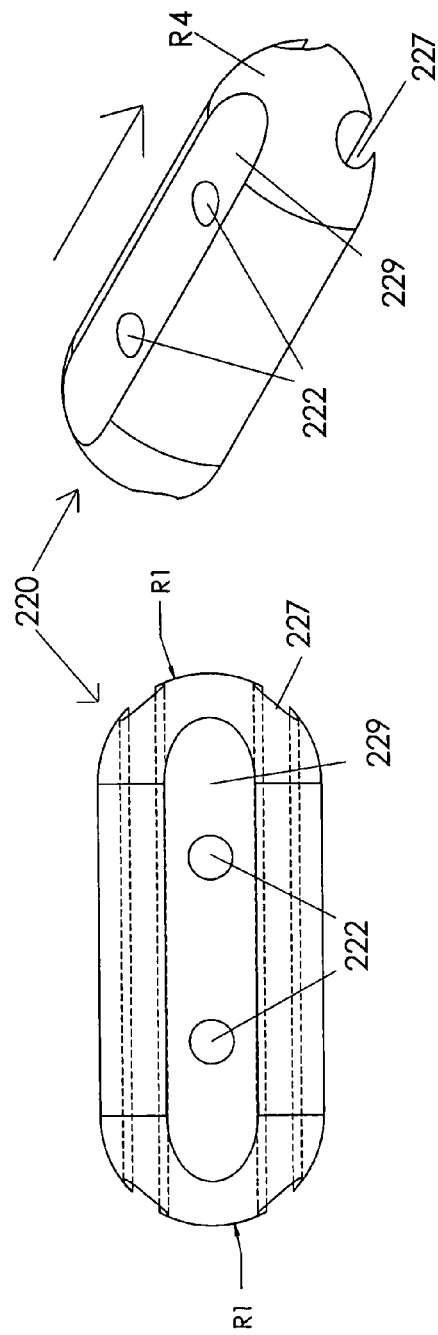
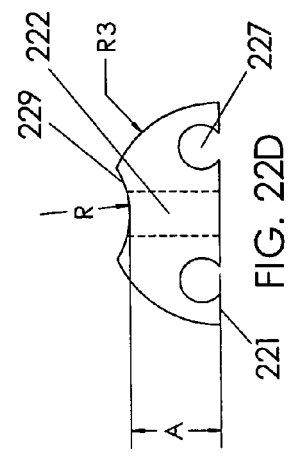
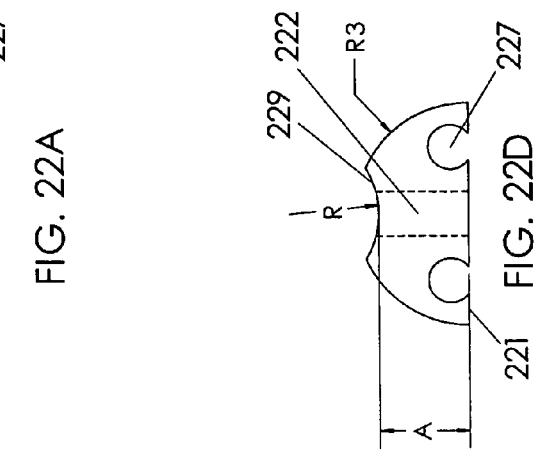
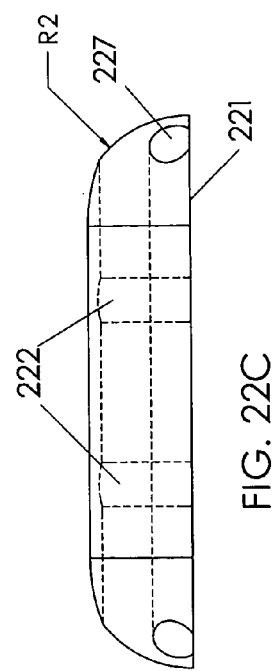
FIG. 22A
FIG. 22B
FIG. 22C
FIG. 22D

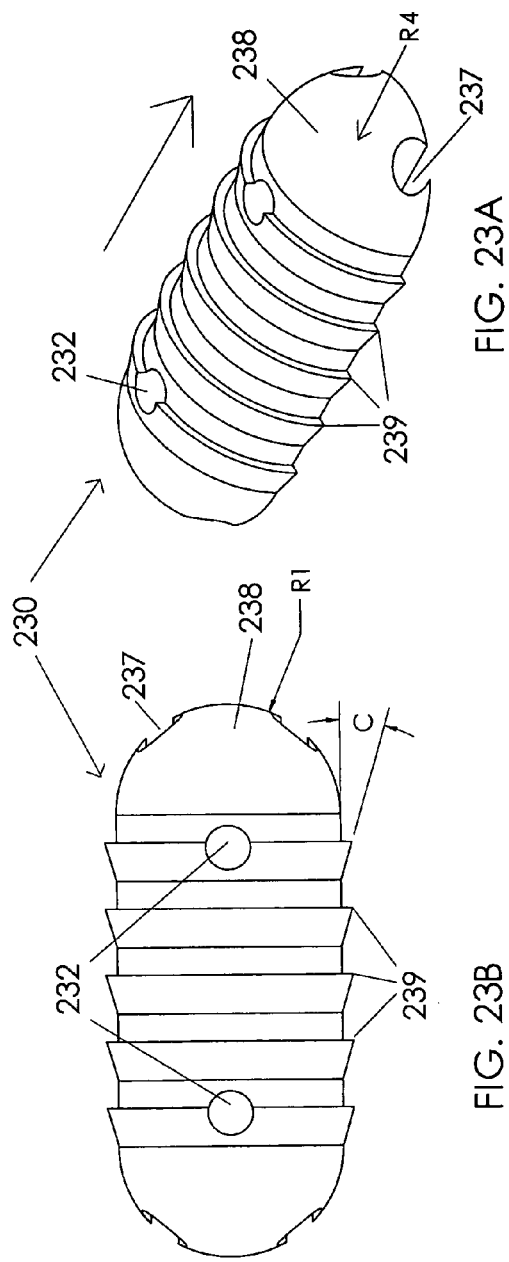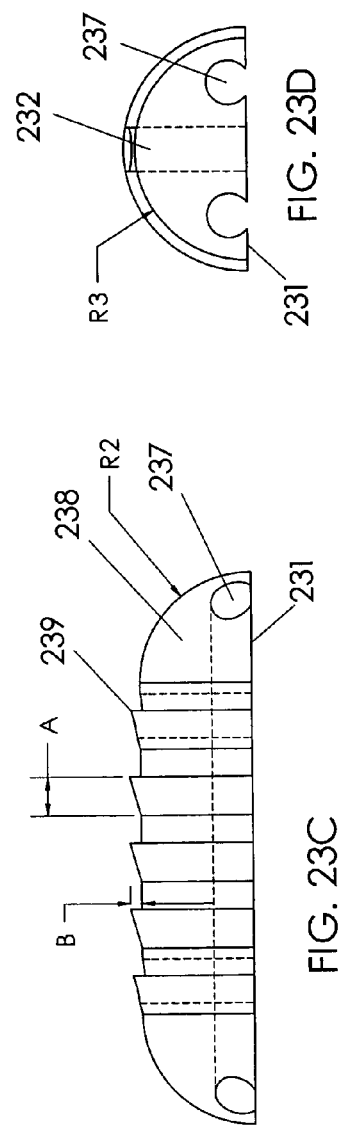
FIG. 23A
FIG. 23B
FIG. 23C
FIG. 23D

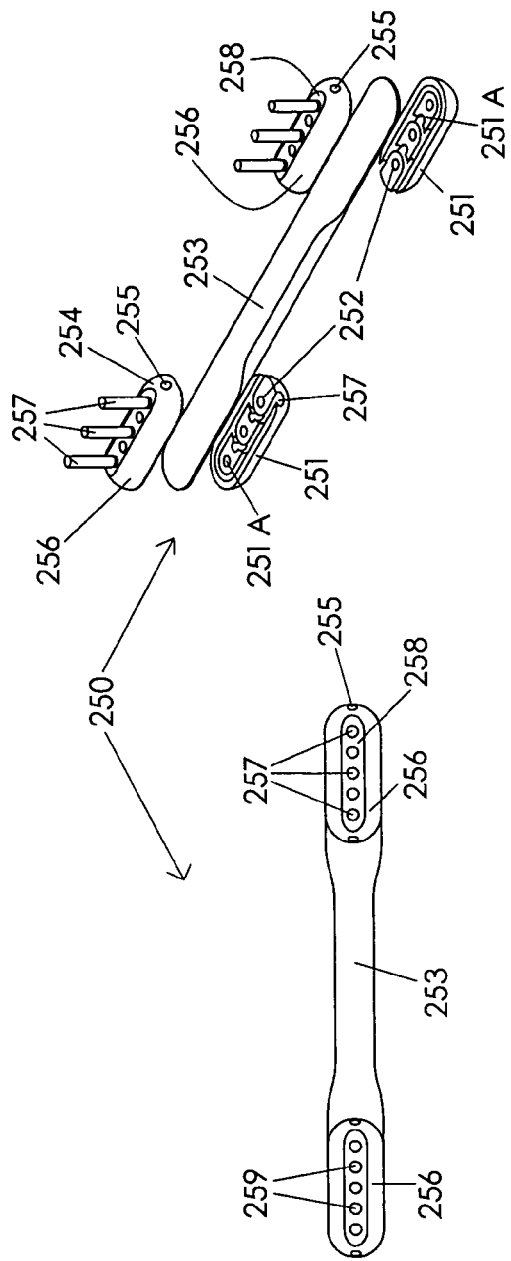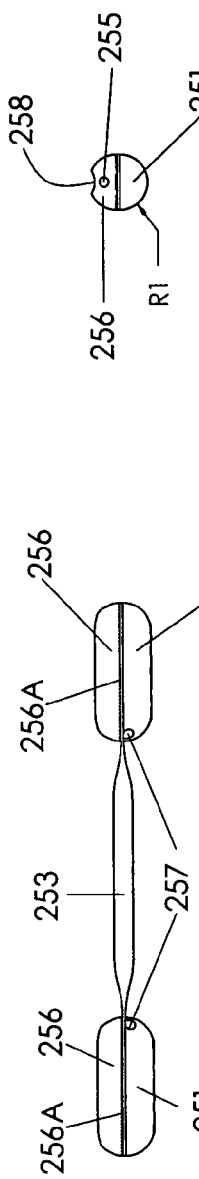
FIG. 25A
FIG. 25B
FIG. 25C
FIG. 25D

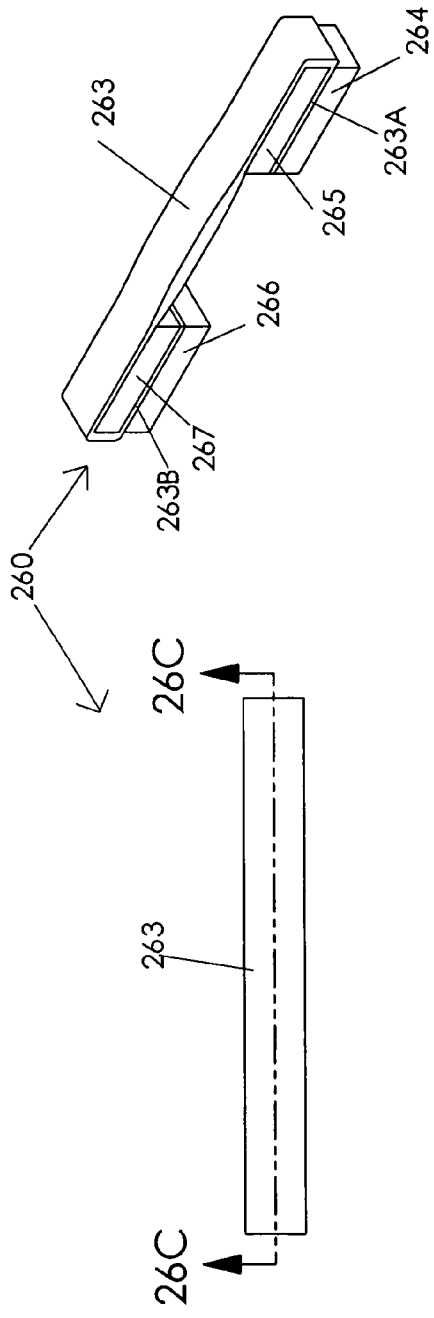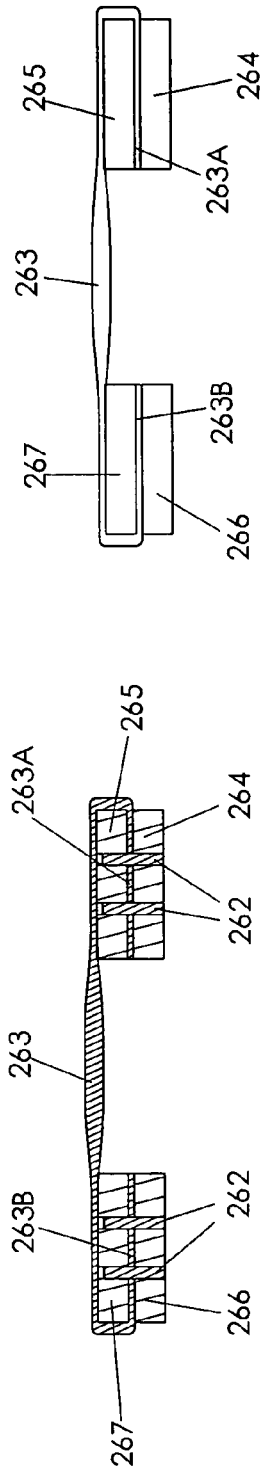
FIG. 26A
FIG. 26B
FIG. 26C
FIG. 26D

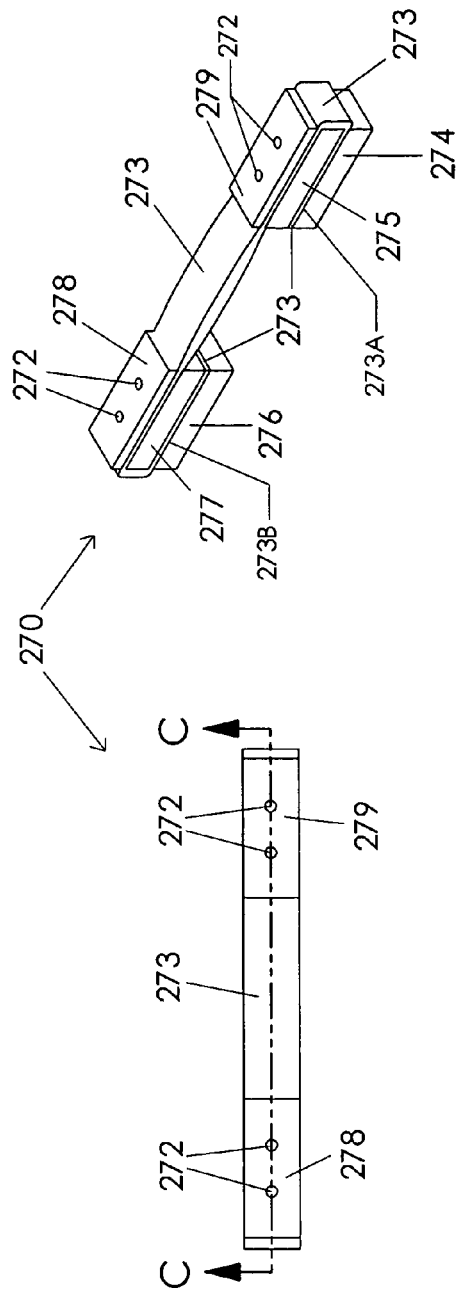
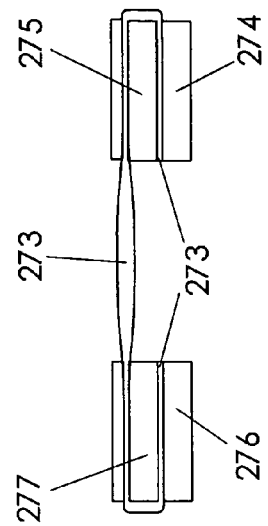
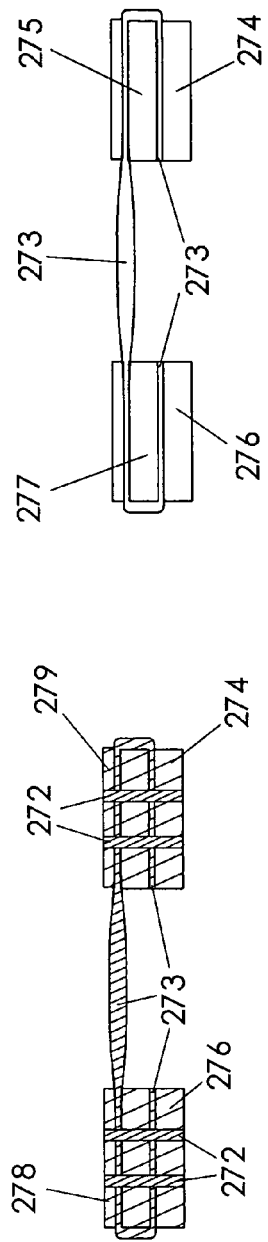
FIG. 27A
FIG. 27B
FIG. 27C
FIG. 27D

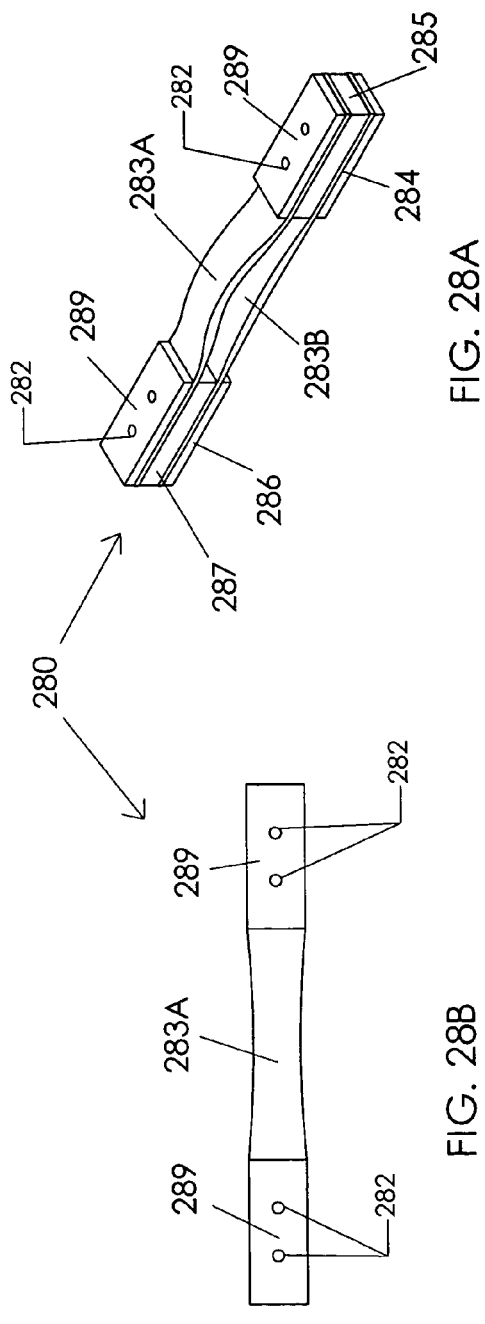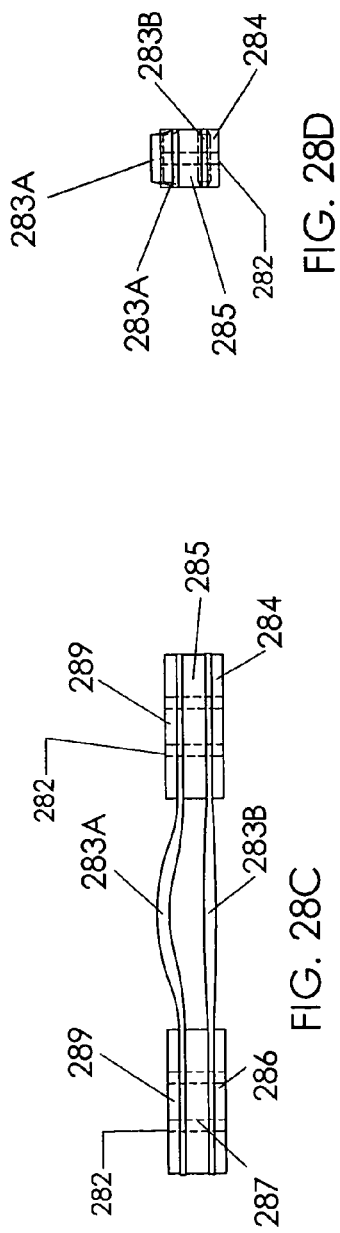

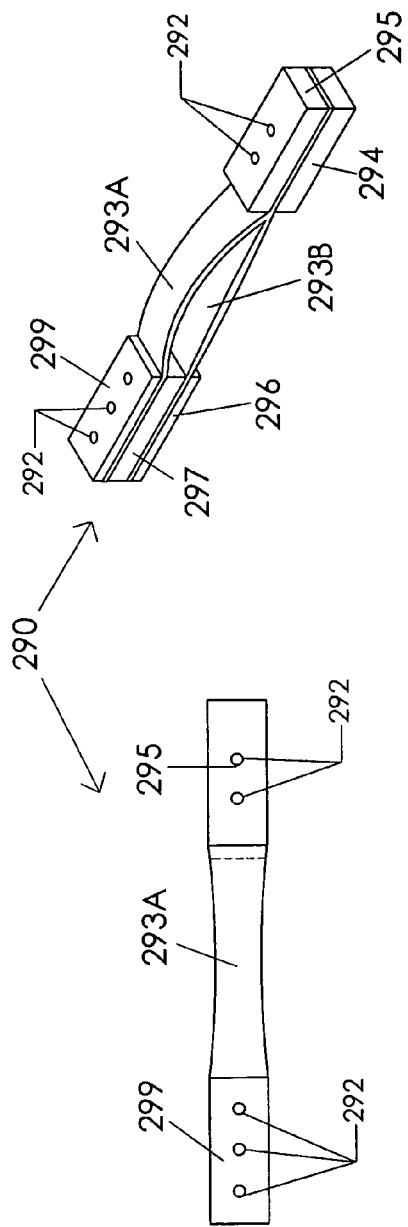
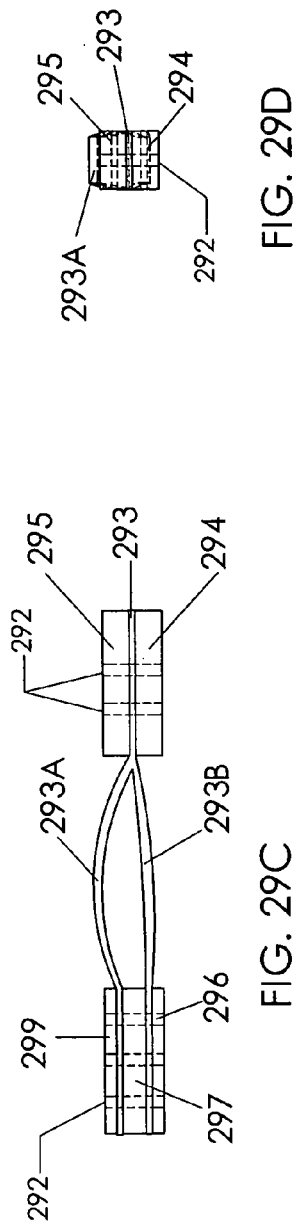
FIG. 29A
FIG. 29D
FIG. 29B
FIG. 29C

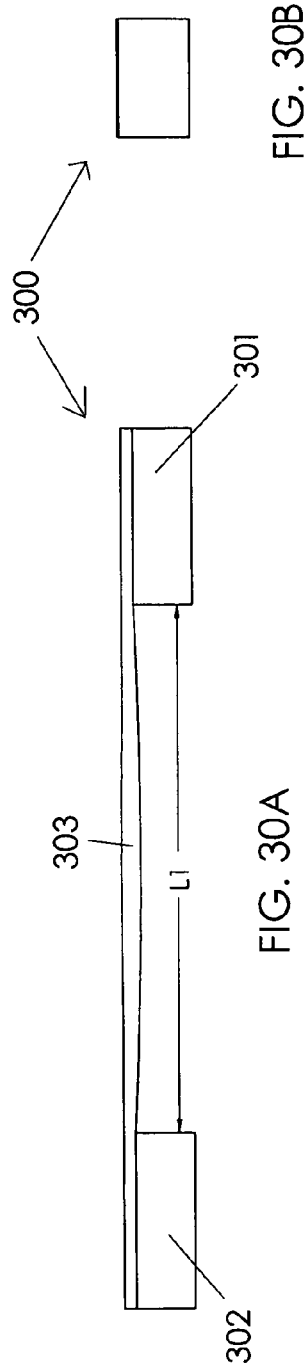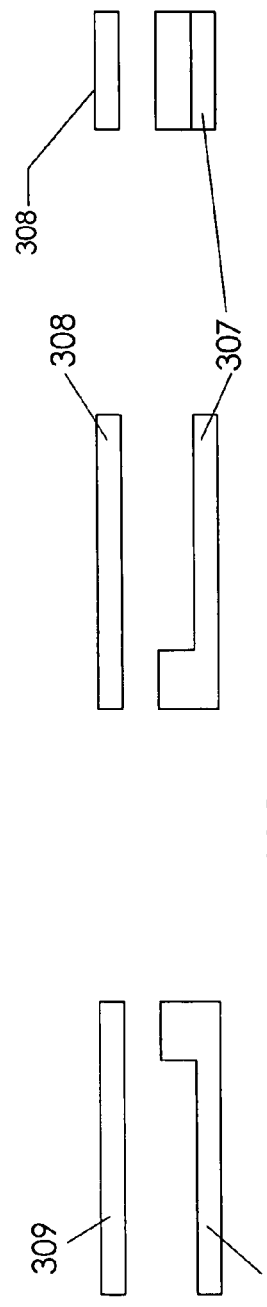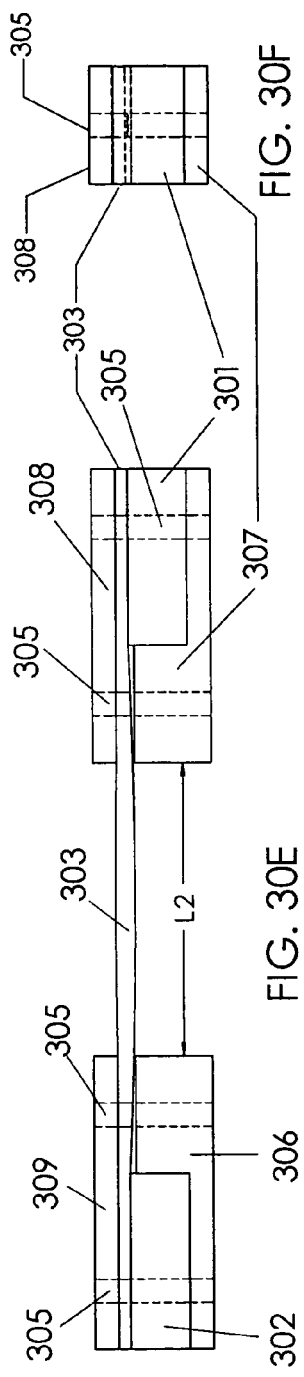

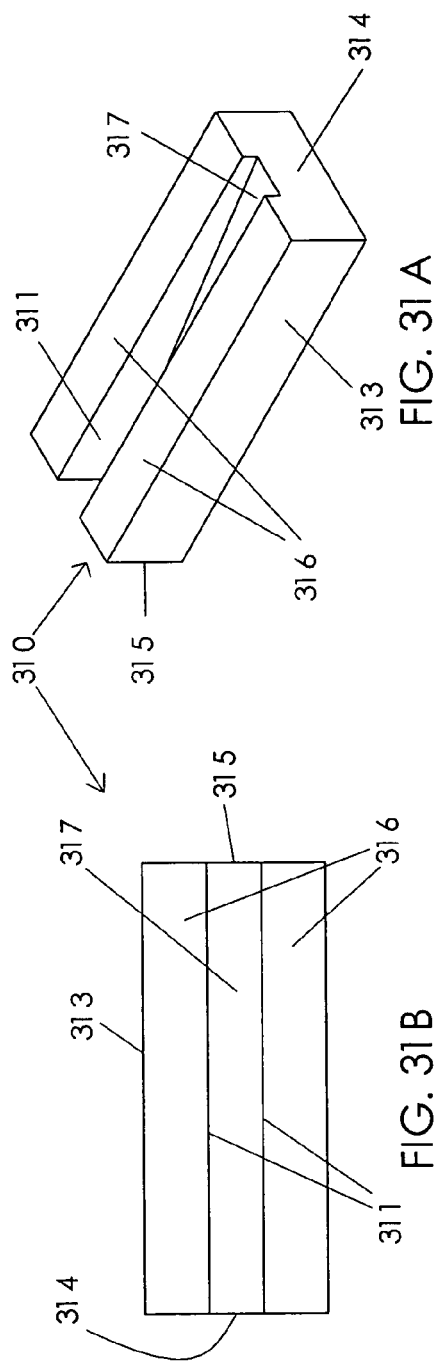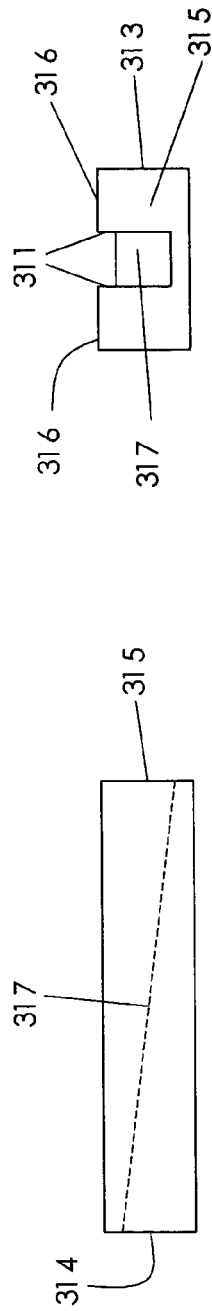
FIG. 31A
FIG. 31B
FIG. 31C
FIG. 31D

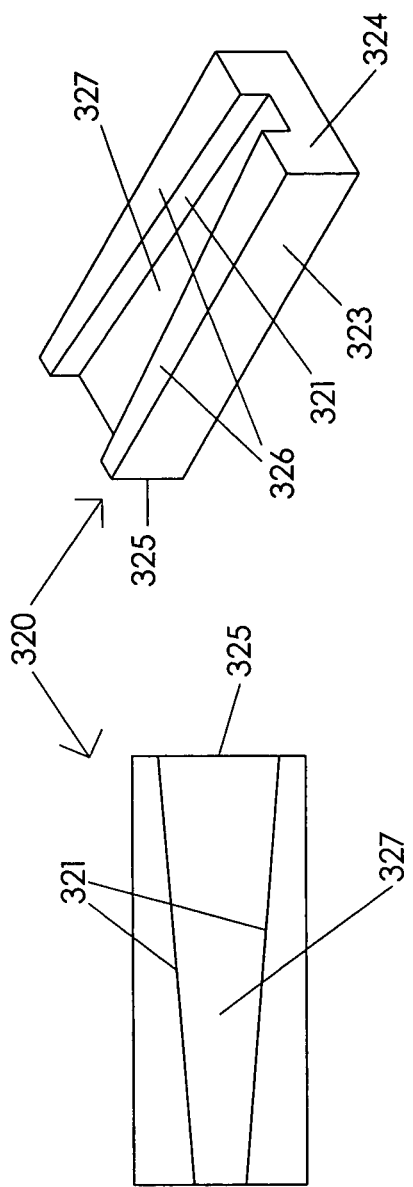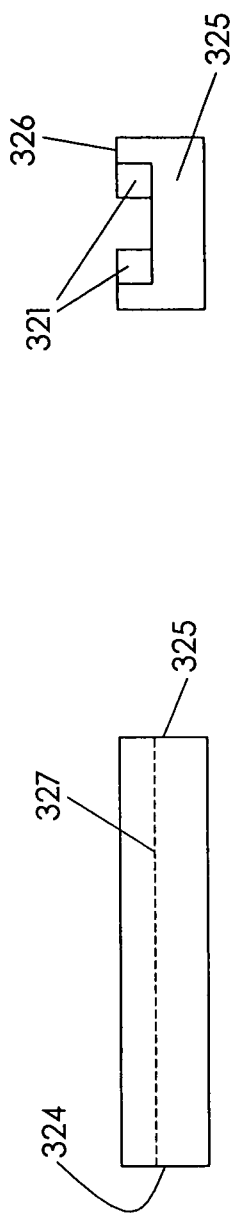
FIG. 32A
FIG. 32B
FIG. 32C
FIG. 32D

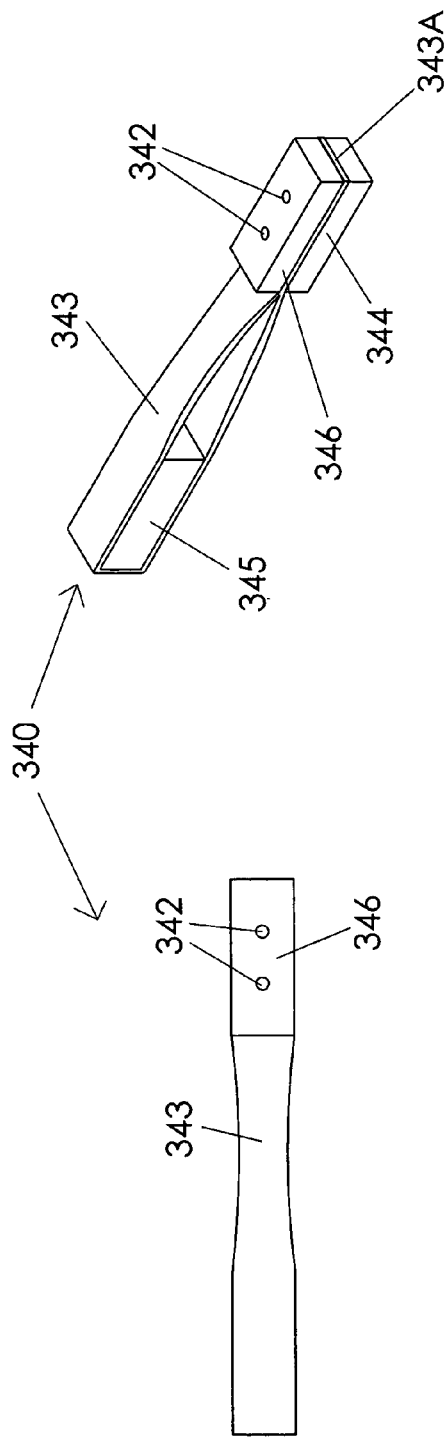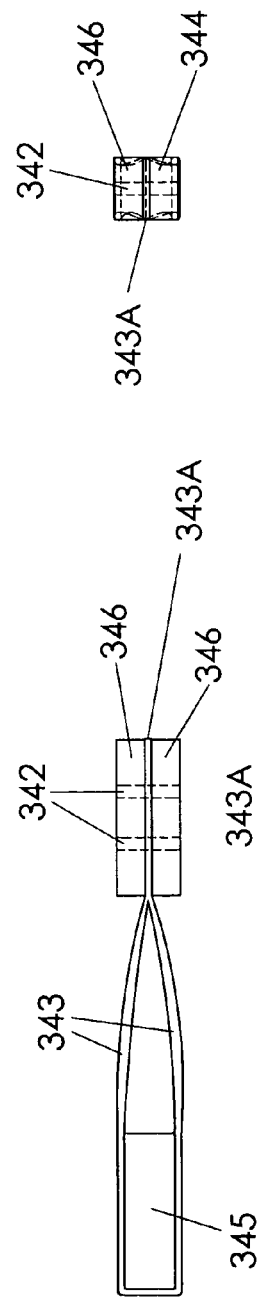
FIG. 34A
FIG. 34B
FIG. 34C
FIG. 34D

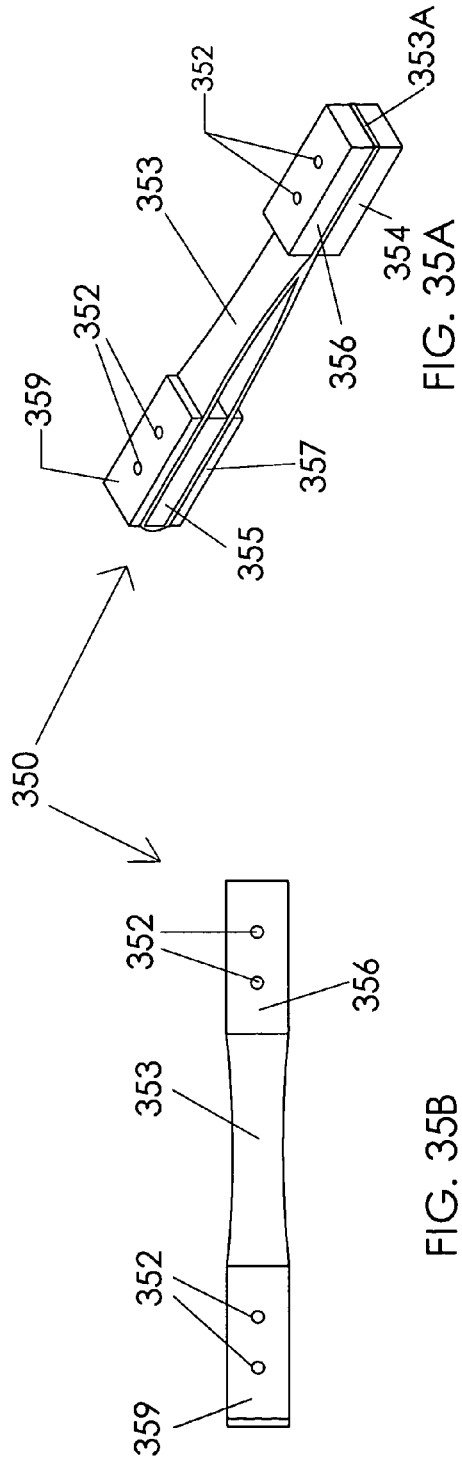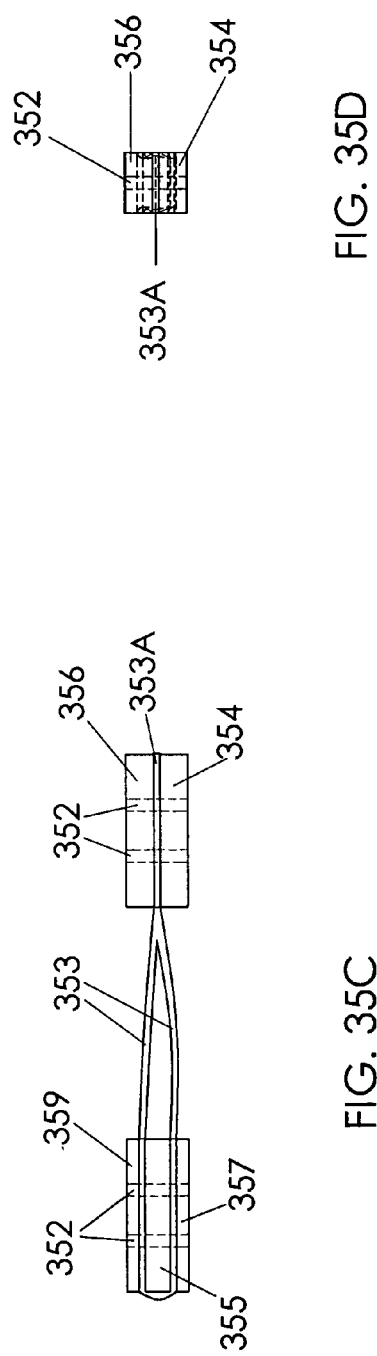

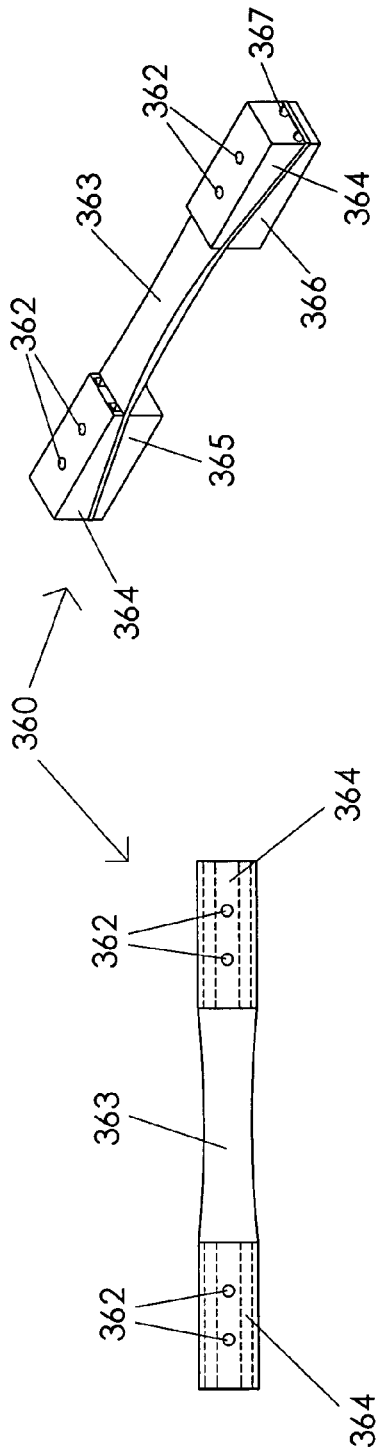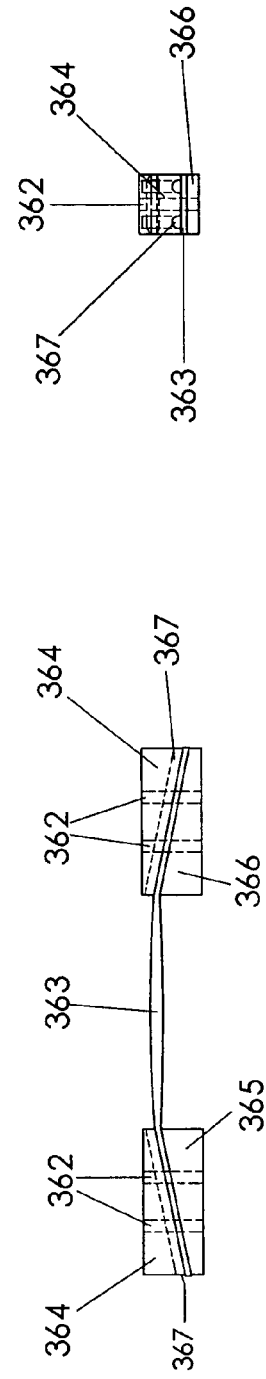
FIG. 36A
FIG. 36D
FIG. 36B
FIG. 36C

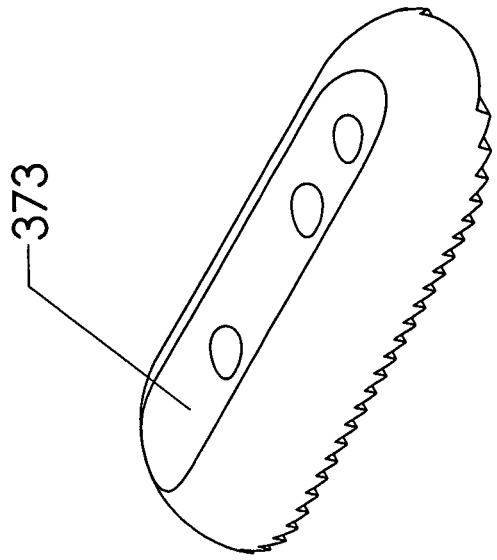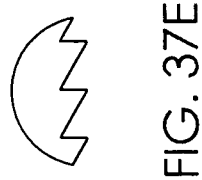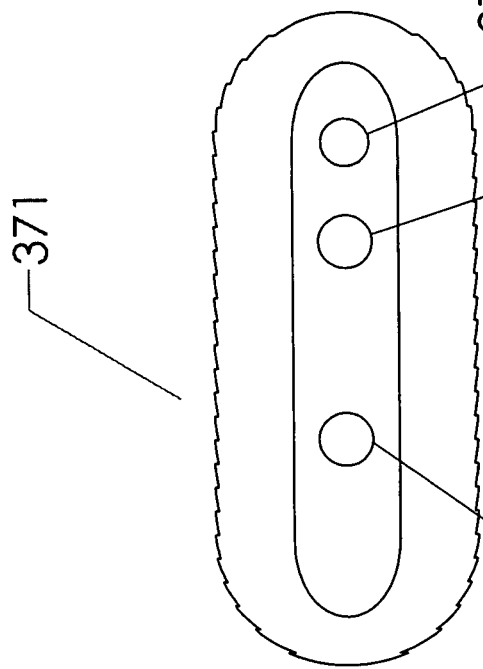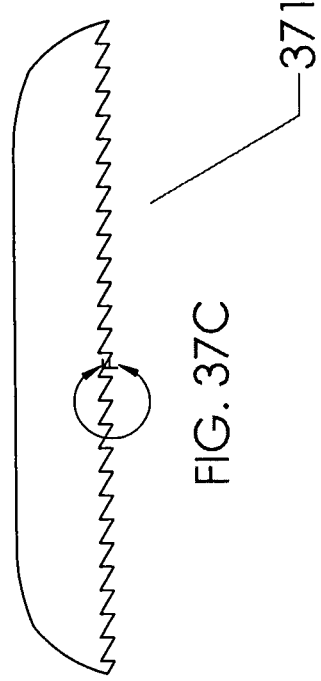

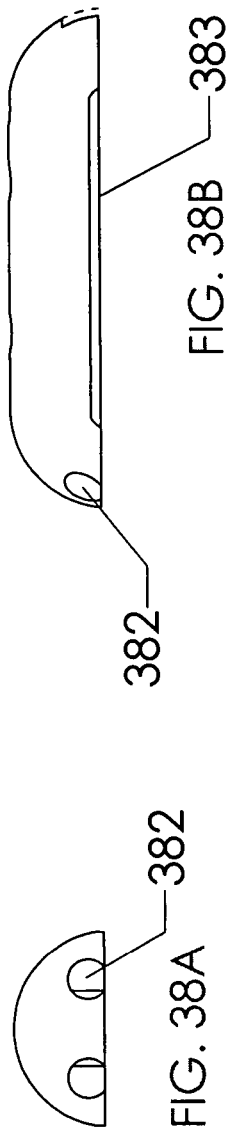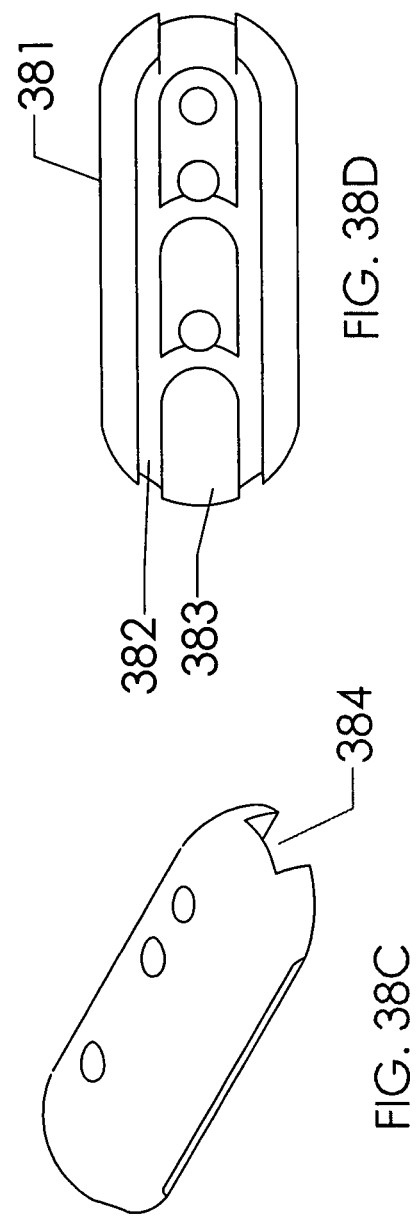

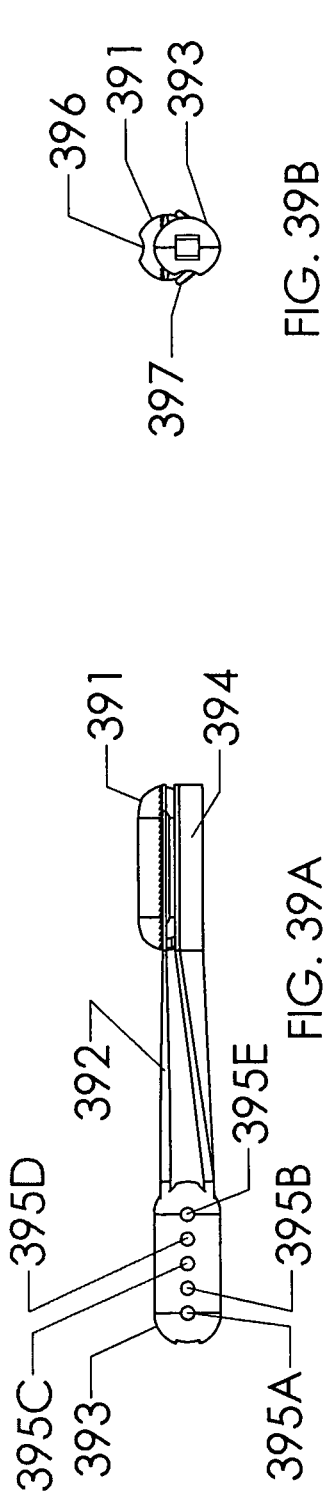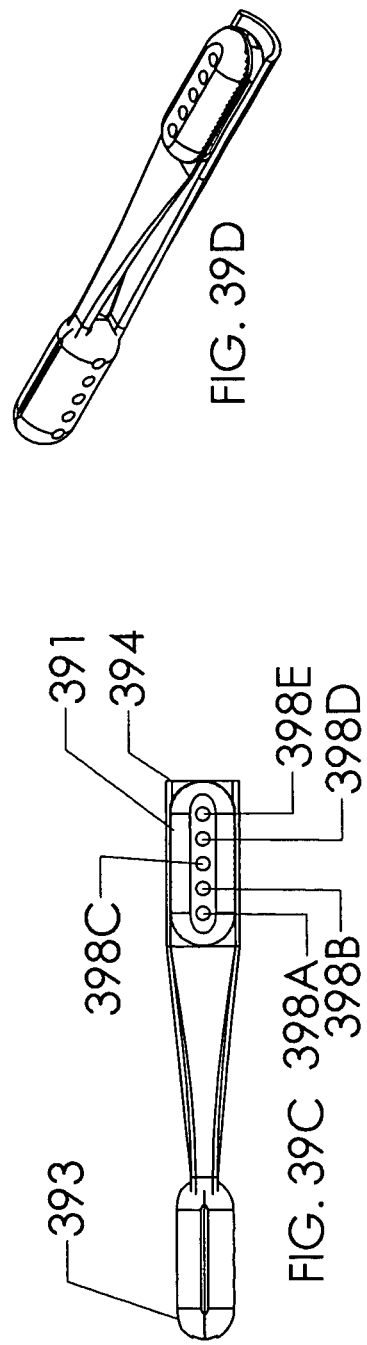

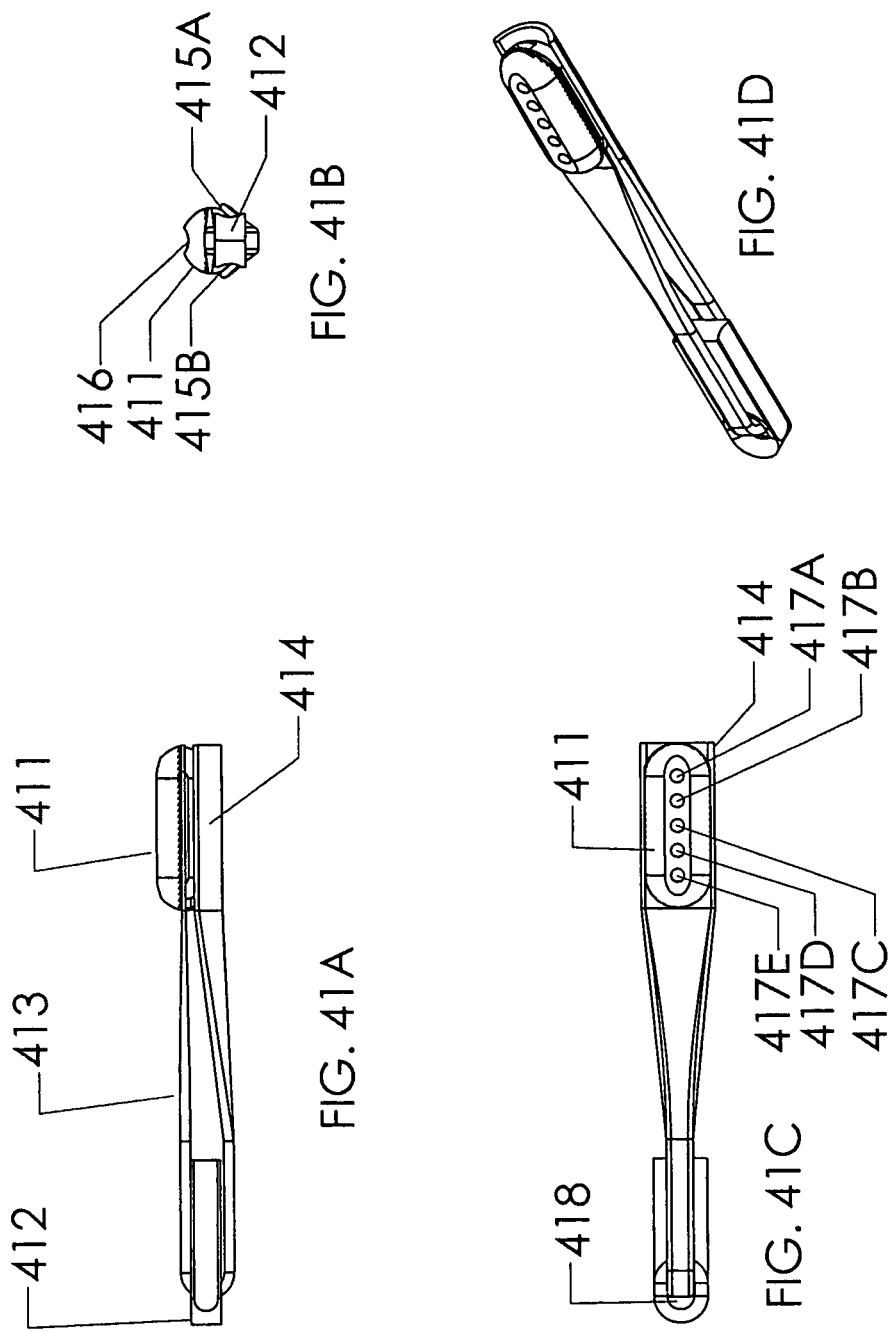

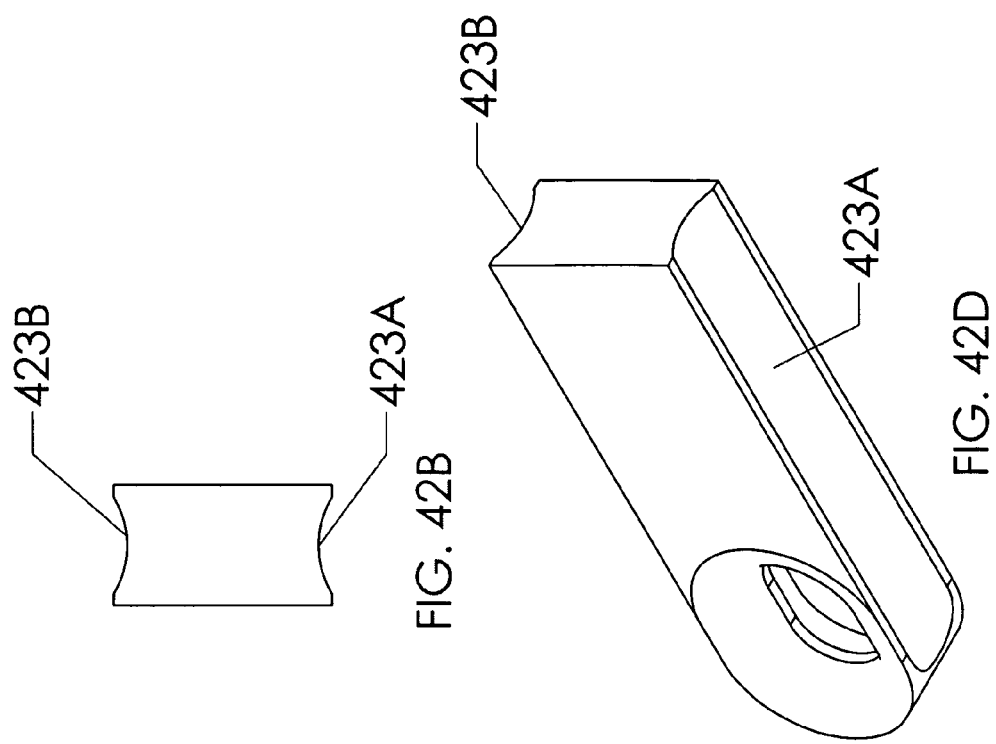
FIG. 42D
FIG. 42B
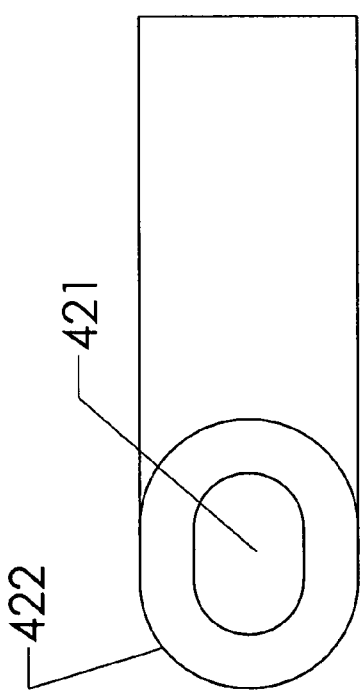
FIG. 42A
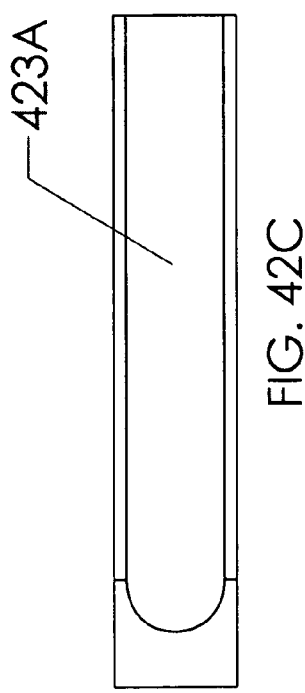
FIG. 42C

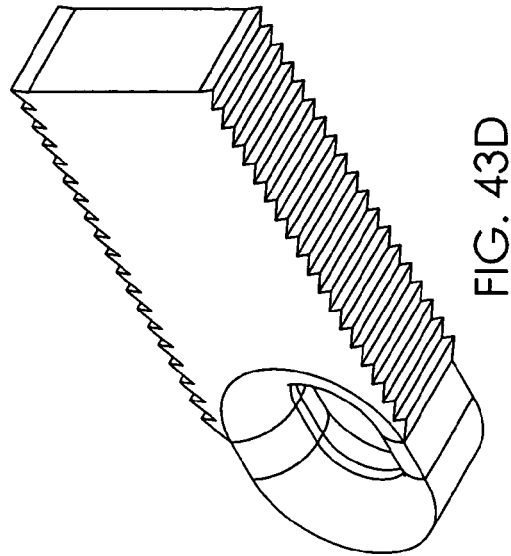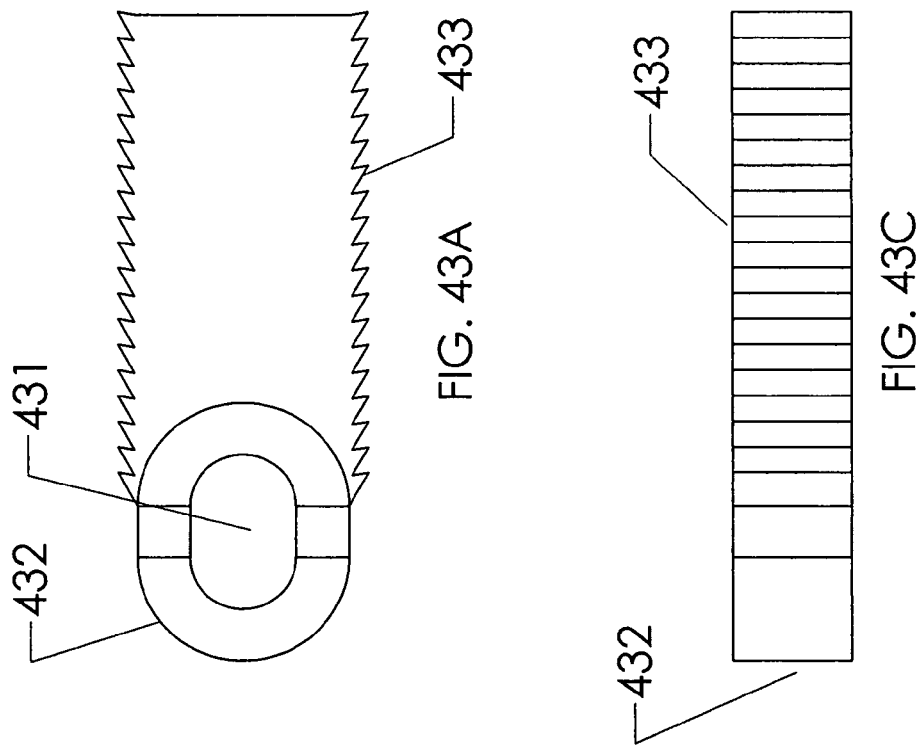

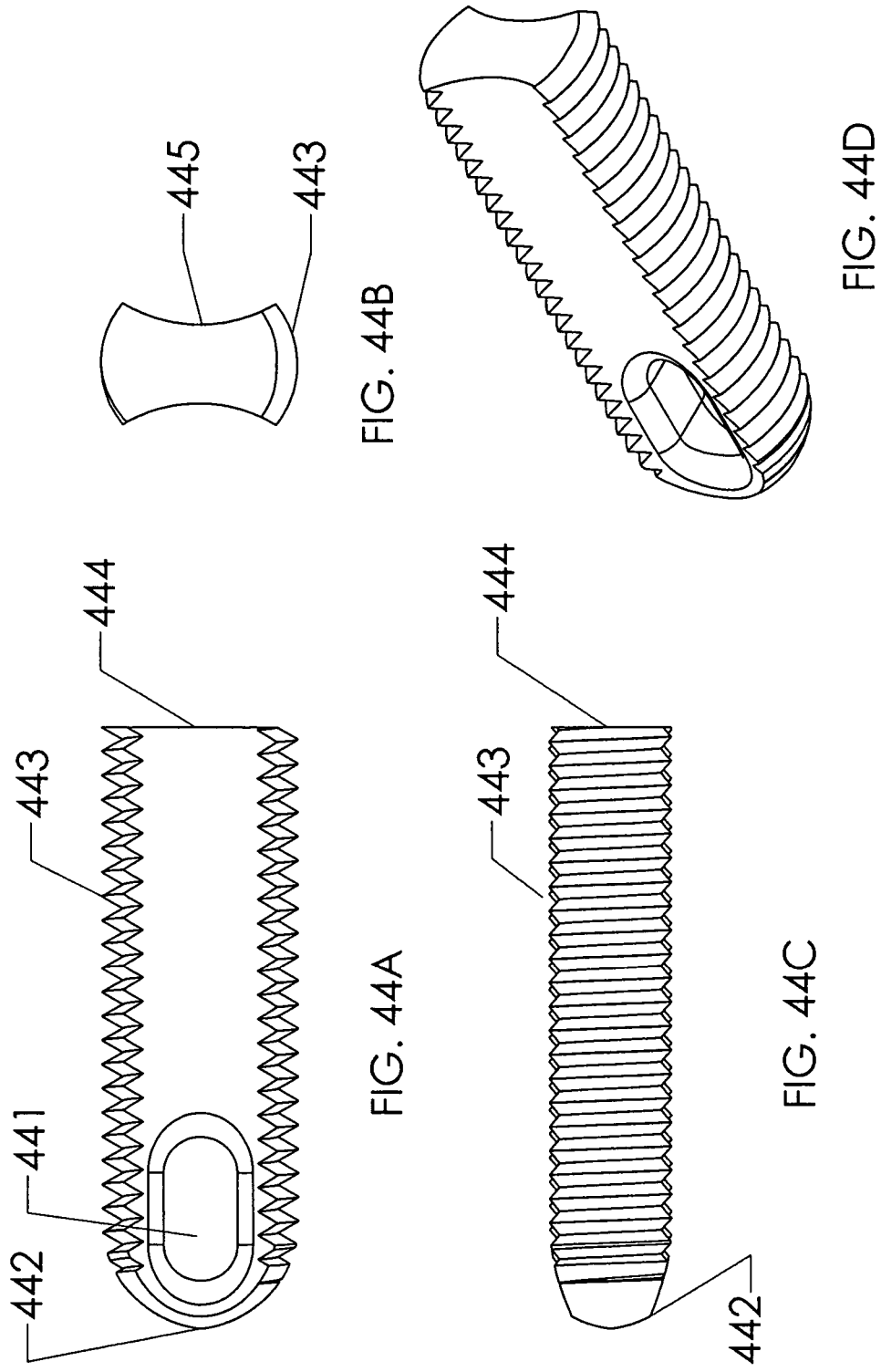

ADJUSTABLE AND FIXED ASSEMBLED
BONE-TENDON-BONE GRAFT

This application is a continuation-in-part of U.S. Ser. No. 11/073,281, filed Mar. 4, 2005, now U.S. Pat. No. 7,776,089.

FIELD OF THE INVENTION

The present invention is related to the field of bone-tendon-bone grafts and components thereof, for implantation in mammals, particularly for implantation in humans. More specifically, the present invention is directed to an intermediate bone block for use in bone-tendon-bone (BTB) grafts wherein the intermediate bone block is capable of being used with the same or a different bone block to form a bone block assembly that has an enhanced gripping feature for gripping soft tissue to form an assembled bone-tendon-bone graft suitable for implantation into a patient. The bone-tendon-bone grafts of the present invention are useful because they offer surgeons and patients the advantages of full internal tendon capture, bone to bone contact at the healing interface, use of any suitable tendon specimen, construction to a predetermined gage length, and adherence to preferred surgical technique and fixation methods, while maintaining a significantly increased tensile strength over BTB grafts formed by stitching, stapling or compression alone.

BACKGROUND OF THE INVENTION

In the field of medicine, there has been an increasing need to develop implant materials for correction of biological defects. Particularly in the field of orthopedic medicine, there has been the need to replace or correct bone, ligament and tendon defects or injuries. As a result, there have emerged a number of synthetic implant materials, including but not limited to metallic implant materials and devices, devices composed in whole or in part from polymeric substances, as well as allograft, autograft, and xenograft implants. It is generally recognized that for implant materials to be acceptable, they must be pathogen free, and must be biologically acceptable. Generally, it is preferable if the implant materials may be remodeled over time such that autogenous bone replaces the implant materials. This goal is best achieved by utilizing autograft bone from a first site for implantation into a second site. However, use of autograft materials is attended by the significant disadvantage that a second site of morbidity must be created to harvest autograft for implantation into a first diseased or injured site. As a result, allograft and xenograft implants have been given increasing attention in recent years. However, use of such materials has the disadvantage that human allograft materials are frequently low in availability and are high in cost of recovery, treatment and preparation for implantation. By contrast, while xenograft implant materials, such as bovine bone, may be of ready availability, immunological, regulatory and disease transmission considerations imply significant constraints on the ready use of such materials.

In view of the foregoing considerations, it remains the case that there has been a long felt need for increased supplies of biologically acceptable implant materials to replace or correct bone, ligament and tendon defects or injuries. This invention provides a significant advance in the art, and largely meets this need, by providing materials and methods for production of various bone-soft tissue implants from component parts to produce assembled implants.

Orthopedic medicine is increasingly becoming aware of the vast potential and advantages of using bone/tendon/bone grafts to repair common joint injuries, such as Anterior Cruciate Ligament (ACL) or Posterior Cruciate Ligament (PCL) tears. One technique that is currently used for repairing these types of injuries involves surgically reconnecting the torn portions of a damaged ligament. However, this technique is often not possible, especially when the damage to the ligament is extensive. To address situations where the damage to the joint ligaments is severe, another technique commonly performed involves redirecting tendons to provide increased support to a damaged knee. These conventional techniques are not without their shortcomings; in most cases, the repaired joint lacks flexibility and stability.

The recent utilization of bone/tendon grafts has dramatically improved the results of joint repair in cases of severe trauma. Even in cases of extensive damage to the joint ligaments, orthopedic surgeons have been able to achieve 100 percent range of motion and stability using donor bone/tendon grafts. Despite these realized advantages, there have been some difficulties encountered with utilizing bone/tendon grafts. For example, surgical procedures involving transplantation and fixation of these grafts can be tedious and lengthy. Currently, bone-tendon-bone grafts must be specifically shaped for the recipient during surgery, which can require thirty minutes to over an hour of time. Further, surgeons must establish a means of attaching the graft, which also takes up valuable surgery time. Accordingly, there is a need in the art for a system that addresses this and the foregoing concerns. Thus it is an object of this invention to provide a BTB that is constructed to precise dimensions and is adapted for robust fixation while allowing adherence to preferred surgical techniques.

Bone-tendon-bone (BTB) grafts of the prior art are made in one of two ways: (1) by harvesting a naturally occurring tendon/ligament and portions of the bone(s) to which it is attached, thus maintaining the naturally occurring attachment of tendon/ligament and bone; or (2) by attaching the opposing ends of one or more pieces of tendon, ligament or a synthetic material to separate bone blocks. The name BTB is used for historical reasons. One skilled in the art recognizes that by definition, a "tendon" is a collagenous cord that attaches muscle to its point of origin, typically to bone. By definition, a "ligament" is a band of collagenous tissue that connects bone or supports viscera. Thus, it would appear that a BTB would more properly be called a bone-ligament-bone implant. However, many of the earliest BTBs employed a tendon, which is larger and generally more plentiful in a body. Hence, the name BTB became adopted by the art. We have used the term BTB to encompass all of the bone-soft tissue grafts described herein.

Tendons (or ligaments) are fibrous semi-hard materials that are slippery and difficult to grip. Thus, one of the issues in manufacturing an assembled BTB is how to attach the slippery tendon to the bone. The tendon has a tendency to squirm and slip when compressed between boney surfaces, much like a banana peel compressed between the floor and one's foot. One solution that is commonly used is to bite the tendon with a component that has some sort of teeth or threads, providing improved gripping over a flat surface. However, teeth or threads have a tendency to cut into the tendon fibers when the tendon is pulled at high tensile strength. Thus, most assembled BTBs provide some sort of trade-off between reducing slipping and squirming by biting which does not allow for achievement of maximum tensile strength.

U.S. Pat. No. 5,370,662 ("the '662 patent"), which issued to Stone on Dec. 6, 1994 and which is entitled "Suture Anchor Assembly," discloses the use of a screw made from titanium, stainless steel, or some other durable, non-degradable, biocompatible material having a portal at one end for attaching a suture connected to a soft material, such as a ligament or tendon. U.S. Pat. No. 5,370,662 at col. 1, lines 8-9. One problem with such a device is that the screw, although biocompatible, will never become assimilated into the patient's body. A second problem is that the tendon or ligament will never form a natural attachment to the screw.

One attempt at solving these problems was disclosed in U.S. Pat. No. 5,951,560 ("the '560 patent"), which issued on Sep. 14, 1999 to Simon et al. and which is entitled "Wedge Orthopedic Screw." The '560 patent discloses a wedge-shaped interference screw made from a biocompatible material for use with a ligament and with two bone blocks for performing anterior cruciate ligament repairs. In the '560 patent, a bio-compatible, wedge-shaped interference screw, a bone block and a ligament are inserted into an osseous tunnel drilled into a bone of a patient in need of a ligament repair. The interference screw compresses the flat surface of a bone block against a ligament that is pressed into the wall of the osseous tunnel. As the interference screw advances, the force that it presses against the ligament is buttressed by the force against the opposing tunnel wall. A second interference screw compresses a second bone block against an opposing end of the ligament in a second osseous tunnel drilled in a second bone in need of ligament repair. It is more difficult to pull a predetermined tension on the tendon because the tendon slips in the bone tunnel and uncontrollably alters the tension when the interference screw is being threaded in the bone tunnel. The slippery ligament is also subject to slippage when compressed between the bone block and the tunnel wall. Such slippage results in a loss of tension in the joint. In the case of an anterior cruciate ligament (ACL) repair, this loss of tension causes a wobbly knee. This is undesirable in any human and particularly athletes. It is an object of the present invention to provide a bone to tendon connection that will decrease slippage and loss of tension in a BTB. Therefore, it is an object of the present invention to provide a BTB with a stiffness of at least 90N/mm, preferably 170N/mm, more preferably 230N/mm. It is also an object of the present invention to provide a BTB with an elongation of no more than 5 mm, preferably less than 2 mm, more preferably less than 1 mm. Stiffness and elongation for any given BTB can be calculated by methods known in the art. Stiffness is defined as the slope of the force-displacement curve when the BTB is subject to axial load increasing from below 100 Newtons to above at least 200 Newtons. Elongation is defined as the difference in length for a given BTB measured before the first cycle of a dynamic load test and after 1000 cycles of loading to at least 200 Newtons.

Another approach to making a BTB is disclosed in U.S. Pat. No. 5,961,520 ("the '520 patent") which issued to Beck, et al. on Oct. 5, 1999, and which is entitled "Endosteal Anchoring Device for Urging a Ligament Against a Bone." Like the '560 patent, the '520 patent utilizes an interference screw and a bone block (called an "anchor body" therein) to press the end of a ligament against the side wall of an osseous tunnel in the patient's bone. The '520 patent differs from the '560 patent in that the ligament loops around the bone block in a "U" shape. This "U" shape of the tendon captures the tendon in the first bone tunnel, but leaves two free tendon ends to be secured in the second bone tunnel. In addition in the '520 patent, the bone block, which presses the ligament against the walls of the osseous tunnel contains two grooves for "locking" (col. 7, line 2) the ligament in place, and "restricting excessive compression on the ligament" (col. 7, lines 8-9). The "locking" of the tendon against the tunnel wall still leaves the tendon free to move against the tunnel wall near the ends of the anchor body. This leads to impaired healing and recovery due to tendon to bone contact within the tunnel and also due to micromotions of the tendon within the tunnel. Additionally, the location of the tendon in the locking grooves is a function of the anchor body design and is not a controlled design parameter. Thus, the tendon placement with respect to either the tunnel wall or the tunnel centerline cannot be matched to particular surgical needs or to surgeon preference.

Yet another approach to making a BTB is disclosed in commonly assigned U.S. Pat Appl. Pub. No. 2003/0023304 ("the '304 application"), to Carter et al., which published on Jan. 30, 2003. The '304 application discloses several embodiments of a BTB. In each of the various embodiments, a tendon is bound in an internal chamber created in the bone blocks. For example, in FIG. 10 a plurality of cams reverse the direction of the tendon several times and cancellous chips packed in any open space bite into the tendon to keep it from slipping. In FIG. 12, a screw compresses the tendon against the side of an internal chamber. In FIG. 14, an internal wedge that has teeth bites into a tendon and tightens the grip as the tendon is pulled. In yet another embodiment, shown in FIG. 15, one end of a tendon is doubled over and the doubled over end is held in place by a series of grooves and rings. While all of these embodiments are useful, they each are challenging to manufacture and/or assemble due to their inherent complexity and reliance on small or intricate parts. It is an object of the present invention to provide a BTB having a robust design, simple components, ease of manufacturability, and high reliability, all while maintaining an acceptable tensile strength, stiffness, and elongation performance. This is important for all BTB grafts, especially for those implanted in athletes and other individuals where maximum performance is required.

One isolated and purified BTB that is not hindered by slippage or cut fibers when subjected to high tensile pulling is disclosed in commonly assigned U.S. Pat. No. 6,497,726 ("the '726 patent") which issued on Dec. 24, 2002 to Carter et al. The '726 patent discloses the use of natural BTBs that are cut from allograft or xenograft sources, commonly referred to as "pre-shaped BTBs." Typically, the BTB is cut as a single piece from a section of the patella (bone), patellar tendon and the tibia (bone) of the donor. One problem is that only 2-3 grafts can be obtained per knee of the donor, depending upon the donor's age and health. Hence, it is an object of the present invention to be able to make BTB grafts in large quantities. It is also an object of the present invention to make BTB grafts having high tensile strength, suitable for ACL repairs, from tendon and bone components, wherein the BTBs are constructed so as to minimize the art recognized slippage and tearing associated with conventional modes of construction as described above. Another problem with pre-shaped (natural) BTBs is that the size of the BTB or the length of the tendon between the two bone pieces cannot be precisely selected. Some of the physical dimensions of the graft, particularly tendon (ligament) length, are determined by the anatomy of the donor. Frequently, this leads to compromises such as excessive gage length, or length between the bone blocks, which result in surgical challenges and compromised healing and recovery. For example, a natural BTB with a tendon that is too long for an ACL repair results in having a length of unsecured and wobbling tendon in the bone tunnel between the ends of the secured bone portions. The wobbling tendon hinders healing in the bone tunnel. Hence, it is yet another object of the present invention to be able to make BTB grafts having a predetermined and variable set of design parameters including gage length, bone block diameter, tendon size, and bone block or tendon shape, size, orientation or a combination thereof.

SUMMARY OF THE INVENTION

The present invention relates to a bone-tendon-bone graft and components thereof. Various embodiments relate to bone blocks (alternatively referred to as "intermediate bone blocks") that can be used to secure soft tissue (e.g., tendon) in a patient. Embodiments of intermediate bone blocks of the present invention may be used singly or in combination with other bone blocks to form bone block assemblies for securing soft tissue.

One embodiment of an implant of the present invention comprises a first bone component at a first end of said implant, a second bone component at a second end of said implant; and a segment of soft tissue having a first end, a midsection and a second end; wherein said first bone component comprises a bone block assembly for securing soft tissue comprising a first intermediate bone block and a second intermediate bone block, said first intermediate bone block and said second intermediate bone block sandwiching said soft tissue therebetween; and wherein the first end and the second end of said soft tissue contact said first bone component, and the midsection of said soft tissue contacts said second bone component.

A second embodiment of an implant of the present invention comprises a first bone component at a first end of said implant, a second bone component at a second end of said implant; and a segment of soft tissue of sufficient length to extend between said first and second bone components; wherein said first bone component comprises a bone block assembly for securing soft tissue comprising a first intermediate bone block and a second intermediate bone block, said first intermediate bone block and said second intermediate bone block sandwiching said soft tissue therebetween, wherein said second bone component comprises a bone block assembly comprising a first intermediate bone block and a second intermediate bone block, said first intermediate bone block and said second intermediate bone block sandwiching said soft tissue therebetween, and wherein said soft tissue extends from said first bone component to said second bone component, is doubled back through or around said second bone component, and extends back to said first bone component.

A third embodiment of an implant of the present invention comprises a first bone component at a first end of said implant a second bone component at a second end of said implant; and a segment of soft tissue of sufficient length to extend between said first and second bone components; wherein said first bone component comprises a bone block assembly for securing soft tissue comprising a first intermediate bone block and a second intermediate bone block, said first intermediate bone block and said second intermediate bone block sandwiching said soft tissue therebetween, wherein said second bone component comprises an intermediate bone block comprising a top, a bottom, at least two lateral sides connecting said top and said bottom, and at least one portal through said intermediate bone block from said top side to said bottom side, and wherein said soft tissue contacts the first bone component in at least two places along the length of said soft tissue, and said soft tissue contacts the second bone component in at least one place along the length of said soft tissue.

In a preferred embodiment of an implant having a bone component at either end, the soft tissue extends from the first bone component to the second bone component, is doubled back through said second bone component, and ends underneath said first bone component such that it is compressed into the bone tunnel wall when an interference screw is used to secure the first bone component. Some embodiments may be assembled as implants of predetermined fixed gage lengths, while other embodiments allow physicians to adjust the gage length intraoperatively.

Another embodiment of an implant of the present invention has only one bone component. An implant of this type comprises a soft tissue component and a bone component; wherein said bone component comprises a top, a bottom, a leading end, a trailing end, at least two lateral sides connecting said top and said bottom, and at least one portal through said bone implant from said top side to said bottom side sized to accept said soft tissue. Preferably, one of said lateral sides comprises a retention feature for maintaining the implant at the site of implantation, selected from the group consisting of an interference screw groove, angled teeth, symmetrical teeth, and threads. It s also preferred that portal be located at said leading end, said leading end being rounded to aid in insertion of the implant.

The Applicants discovered that inserting one to ten cavities on the compressive surface (i.e., the soft tissue engaging surface) of a bone block (hereinafter Applicants' "intermediate bone block") provides the bone block with an unexpectedly superior grip of a tendon (or other soft tissue), relative to bone blocks with untextured (smooth) or textured tissue engaging surfaces. It is thought that the cavities on the tendon engaging face capture uncompressed tendon (or soft tissue) from above the cavity and the overflow of adjacent compressed tendon (or soft tissue) allowing the compressive surfaces of the Applicants' intermediate bone block to grab and hold the tendon (or soft tissue) without damaging it, rather than float on it. A preferred cavity is a channel in the tendon (or soft tissue) engaging face of the bone block.

The Applicants also discovered that the cross-sectional shape of the cavities, and the layout of the cavities across the soft tissue engaging face of the bone block greatly affected the overall grip on a segment of soft tissue sandwiched between the tissue engaging face of Applicants' intermediate bone block and any other bone block. Cavities have cross-sectional profiles that are rectangular, square, semi-circular, semi-ovular, triangular, trapezoidal, sinusoidal, curvilinear, dovetail, omega or a combination thereof. Preferably, the cavity has an omega ("Ω") shaped cross-section, i.e., is an omega shaped cavity. By the term "omega" shaped cross section is meant that the lateral cross section of the cavity that is cut into the face of the intermediate bone block has the shape of the Greek letter "Ω".

These compression surfaces and cavities (i.e., enhanced gripping features) result in a an intermediate bone block that has the advantages of full internal tendon capture, bone to bone contact at the healing interface, and the use of any suitable soft tissue (e.g., tendon) specimen, and adherence to preferred surgical technique and fixation methods, while maintaining a significantly increased tensile strength over BTBs formed by stitching, stapling or compression alone.

It was also unexpectedly discovered that when the cross-sectional shape of the cavity (preferably, a channel) was omega shaped "Ω", an even more enhanced gripping of the soft tissue (e.g., tendon) between the opposing faces of the bone blocks was achieved. It is believed that the undercut shape of the omega cavity or channel (collectively "cavity") allows it to advantageously capture and hold the uncompressed and overflow soft tissue. Specifically, the omega cavity has a unique shape because it has a narrower mouth than the width of its cross section due to the fact that the face of the bone block is undercut and the undercut is rounded. This feature allows the soft tissue to enter the undercut cavity and expand in a direction perpendicular to the direction of compression immediately above on the tissue engaging surface of the bone block. The rounded profile of the undercut cavity also greatly reduces stress concentrations and allows the soft tissue to distribute the compressive load more evenly across the entire cavity. As a result, the omega "Ω" cavity gently grips the soft tissue without cutting, and prevents it from slipping, sliding or flowing in the direction it is being pulled or squeezed. Moreover, unlike the edges of teeth or ridges (see FIGS. 6A-6D) that concentrate force on a tissue at all times during compression, the edge of the omega cavity only exerts force when needed in response to the tissue therein being pulled or squeezed. In addition, the narrow mouth of the omega cavity on the bone block surface provides an additional benefit by maximizing contact (and thus grip) between the soft tissue (e.g., tendon) and the tissue engaging surface of the bone block.

The unexpected discovery of the improved performance conferred by channels, and particularly the undercut channels, and most particularly the omega "Ω" channels, represents not only a progression of geometric design configuration, but more importantly a transformation in thought: from plain channels cut into the block to incrementally increase surface area or number of contact points, to a new paradigm of engineered cavities that are carefully designed and controlled to gently grab and hold tissue under load.

Based upon the above discovery, the present invention has multiple aspects. In its simplest aspect, the present invention is directed to an intermediate bone block comprising a machined segment of cortical bone, cancellous bone, artificial bone or a combination thereof, the intermediate having a soft tissue engaging face comprising one to ten compression surfaces and one to ten cavities, the compression surfaces suitable for compressing soft tissue, the one to ten cavities suitably sized for receiving uncompressed soft tissue and/or the compressed soft tissue that is being squeezed from adjacent compression surfaces. The one to ten cavity(ies) may be holes, pockets, or channels. When the cavities are holes or pockets, they are preferably undercut. Preferably, the one to ten cavity(ies) are channels. It is within the scope of the invention that the intermediate bone blocks may be made of artificial bone, by which is meant natural or synthetic materials including metals, ceramics polymers, composites or combinations thereof which exhibit properties similar to cortical bone. Commonly known examples are Poly L-Lactic Acid (PLLA) or calcium phosphate or hydroxyapatite based materials. These are available from various manufacturers such as U.S. Biomaterials, Alachua, Fla. and OsteoBiologics, Inc. (OBI), San Antonio, Tex.

When the one to ten cavities are channels, the channels typically have a cross-sectional shape that is rectangular, square, semi-circular, semi-ovular, triangular, trapezoidal, sinusoidal, curvilinear, dovetail, omega or a combination thereof, more typically square, rectangular, semi-circular, semi-ovular, dovetailed, or omega-shaped. Preferably, the one to ten channels have an undercut cross-sectional profile. By the term "undercut" is meant that the cavities open up to be wider than their surface opening, much like a doorway opening into a wider room. Two examples of an "undercut cross-sectional profile" are an omega ("Ω") cross-sectional profile or a blunted triangular cross-sectional profile (like an opening for receiving a dovetail-hereinafter "dovetailed"). An especially preferred cavity is a channel, wherein the channel has an omega cross-sectional profile.

The layout of the cavities and/or channels is also within the scope of this invention. In its simplest form, the cavity can be a single hole in the surface of the bone block with an omega shaped sidewall. Alternatively, the cavity can be a pocket or larger hole made by removing an area of material with an undercut around some or all of the periphery. When the cavity is a single channel or a plurality of channels, the channel(s) can run in the direction of pull of the tendon (FIGS. 12A-12D), or across the direction of pull of the tendon (FIGS. 13A-13D), or at an angle to the direction of pull of the tendon (FIGS. 16A-16D). In one embodiment of the present invention, the intermediate bone block has two channels with an omega cross-section running in the direction of pull of the tendon. See FIGS. 11A-11D. It is also within the scope of the present invention that one or both ends of the bone block have the edge of the tendon engaging face reduced. Typically, this is performed by sanding, routing, grinding or cutting the edge to produce a round, beveled or chamfered edge. See FIGS. 12A-12D. Preferably, this reduction of the end of the tendon engaging face results in an internal leading edge configuration that reduces tissue stresses during assembly and use. It is also within the scope of the present invention that the cross-sectional size of the cavities in any layout be the same (FIGS. 13A-13D) or different (FIGS. 14A-14D). It is additionally within the scope of this invention for the intermediate bone block to have an overall lengthwise tapering profile. See FIGS. 36A-36D.

In other embodiments of the present invention, the layout of the channels can be such that the channels intersect or cross one another. In FIGS. 15A-15D, a series of channels is shown that criss-cross one another to produce a waffle-like pattern on the tendon engaging face of the intermediate bone block. In a simpler embodiment, two channels intersect one another to produce a "V" shaped layout on the tendon engaging face of the intermediate bone block. See FIGS. 16A-16D. This embodiment can also be thought of as a single channel that changes direction much like a bend in the road. It is within the scope of the present invention that the layout of channels include a single "V" shape, a plurality of "V" shapes (see FIGS. 16A-16D) or some combination of different layouts. Other examples of layouts of the channels are "U" shaped, "W" shaped and "A" shaped. Alternative layouts for channels are graphic designs such as company insignia, random or psuedo-random designs such as a labyrinth or maze, or complex mathematically derived patterns such as fractal patterns.

A preferred layout for the channels is "U" shaped. The "U" shaped layout includes a single "U" or 2-10 "Us," which may be stacked or overlapped. Typically, the U's in the layout are stacked top to bottom. In a preferred embodiment, a set of three "U" channels are stacked top to bottom as shown in FIGS. 17A-17D. This layout can be thought of as a variation of the two channels of FIGS. 11A-11D with the channels being interconnected in three places. In an especially preferred embodiment, the intermediate bone block of the present invention has a layout on its tendon engaging face of three stacked "U" shaped channels (as shown in FIGS. 17A-17D), each channel having an omega-shaped cross-section. This channel arrangement of three stacked "U" shapes can also be interpreted as a double stacked "A" shape.

The intermediate bone block has a plurality of uses and can be used with a same or a different bone block to form a plurality of different bone block assemblies suitable for binding to a soft tissue to form an implantable graft suitable for repair of a defect or injury in the body of a mammalian patient. A particularly preferred graft is a bone-tendon-bone graft.

In a second aspect, the present invention is directed to a bone block assembly comprising two components: an intermediate bone block of the present invention in combination with a second bone block. The second bone block can be the same or different than the intermediate bone block as the advantages of the present invention accrue from Applicants' intermediate bone block having an overflow cavity, as described herein, being present on a single bone block. In the bone block assembly, the intermediate bone block and the second bone block are machined to receive 1 to 30 biocompatible connectors. As will be discussed later herein, these biocompatible connectors include any connectors capable of holding the intermediate bone block and the second bone block (i.e., the bone block assembly) together as a unit.

In a third aspect, the present invention is directed to a bone block assembly comprising two components: a first intermediate bone block of the present invention in combination with 2-10 other bone blocks, providing bone block assemblies containing 3-10 bone blocks. The 2-10 other bone blocks can be the same or different than the first intermediate bone block as the advantages of the present invention accrue from an omega cavity being present on a single intermediate bone block. The 3-10 intermediate bone blocks can have various configurations for sandwiching soft tissue. See e.g., FIGS. 27A-D, 28A-D and 29A-D. In these bone block assemblies, the intermediate bone blocks are also machined to receive 1 to 30 biocompatible connectors.

In a fourth aspect, the present invention is directed to an assembled bone-tendon-bone (BTB) implant comprising a bone block assembly of the present invention affixed to one or both ends of a length or a bundle of soft tissue. When the assembled BTB of the present invention has a bone block assembly of the present invention at only one end of the soft tissue, the opposing end of soft tissue may be free (e.g., free tendon end) or the bone block at the second and opposing end of the soft tissue is a naturally occurring bone block or portion of bone. Methods for obtaining a tendon that is naturally attached to a block of bone is disclosed commonly assigned U.S. Pat. No. 6,497,726, entitled "Materials and methods for improved bone tendon bone transplantation" which issued on Dec. 24, 2002, and in commonly assigned U.S. Pat. No. 6,805,713, entitled "Materials and methods for improved bone tendon bone transplantation" which issued on Oct. 19, 2004, both of which are expressly incorporated herein by reference in relation to their disclosure on BTBs and on obtaining a tendon naturally attached to a bone block. When the assembled BTB of the present invention has a bone block assembly of the present invention on each of its ends, the bone block assemblies may be the same or different. In this embodiment, the soft tissue is a length of tendon, a bundle of tendons of the same or different lengths, a length of ligament, a bundle of ligaments of the same length or different lengths, a segment or segments of pericardium, dermis or fascia, or a combination thereof. Preferably, the soft tissue is a length of tendon or ligament or a bundle of tendons or ligaments of the same length or different lengths, or a combination thereof. It is also within the scope of the present invention that the tendons or ligaments or both in the bundles be of the same thickness or of different thicknesses. In the bundles, the tendons, or ligaments or both are allograft, xenograft, synthetic, artificial ligament scaffolds or a combination thereof. Preferably, the tendons are allograft or xenograft. It is also within the scope of the present invention that the intermediate bone block, the second bone block or both may themselves be independently constructed from 1 to 30 bone portions, preferably from 1-10 bone portions, more preferably from 1 to 5 bone portions, even more preferably 1 to 3 bone portions, most preferably from 1 to 2 bone portions.

The bone block assemblies of the present invention are affixed to the end of a predetermined length of soft tissue (e.g., tendon) by 1 to 30 biocompatible connectors that engage each of the two opposing bone blocks and the tendon that is sandwiched therebetween. Suitable biocompatible connectors are disclosed herein and include pins that form an interference fit with holes machined in the bone blocks. Typical pins are made of stainless steel, titanium, or cortical bone. Preferred bone pins are cortical bone pins (i.e., pins made from cortical bone). The bone block assembly is made by stacking an intermediate bone block of the present invention or of the prior art into an assembly fixture (see e.g., FIGS. 33A-33E), then placing a piece of soft tissue into the fixture, followed by a second bone block of the present invention or of the prior art. The assembly fixture is then tightened or clamped to hold the pieces in register while the biocompatible connectors are installed. When the biocompatible connectors are pins, a drill is used to create holes through the assembly, then a reamer cleans and sizes the holes, and finally pins are pressed into the holes to hold the assembly together. The entire assembly is then treated through one or more cleaning or sterilization processes which produces an implantable graft without damaging the tissues in the graft. Alternatively, the components are be treated individually by an appropriate cleaning or sterilization process prior to assembly. In either case, the optional step of terminal sterilization is performed by methods known in the art such as gamma, e-beam, X-ray, or UV irradiation or by vapor phase hydrogen peroxide, or supercritical $CO_2$. Other optional steps include sterile packaging, and/or freezing or freeze drying.

BRIEF DESCRIPTION OF SEVERAL VIEWS OF THE DRAWINGS

FIG. 1 is a view of a first comparative bone block-tendon assembly comprising two bone blocks that sandwich a tendon, each bone block having a smooth tendon engaging surface. This first comparative bone block-tendon assembly is tested for average load to failure (Newtons) in Table 1 relative to bone block-tendon assemblies of FIGS. 2A-2B, 3A-3B, 4A-4D, 5A-5D, each having at least one different tendon engaging surface.

FIGS. 2A-2B are views of a second comparative bone block-tendon assembly comprising two bone blocks that sandwich a tendon, the first bone block having a smooth tendon engaging surface while the second bone block has on its tendon engaging surface a saw-tooth pattern of ridges running perpendicular to the direction of pull of the tendon and the length of the bone block. FIG. 2A is an exploded view of the second comparative bone block assembly. FIG. 2B is a detailed view of the tendon and bone blocks from FIG. 2A. This saw-tooth pattern of ridges is angled to engage the tendon in its direction of pull. (FIG. 6A). This second comparative bone block-tendon assembly is tested for average load to failure (Newtons) in Table 1 relative to bone block-tendon assemblies of FIGS. 1, 3A-3B, 4A-4D, and 5A-5D, each having at least one different tendon engaging surface.

FIGS. 3A-3B are views of a third comparative bone block-tendon assembly comprising two bone blocks that sandwich a tendon, each bone block having a textured (saw-tooth pattern) pattern (FIG. 6A) on its tendon engaging surface. FIG. 3A is an exploded view of the third comparative bone block assembly. FIG. 3B is a detailed view of the tendon and bone blocks from FIG. 3A. This third comparative bone block-tendon assembly is tested for average load to failure (Newtons) in Table 1 relative to bone block-tendon assemblies of FIGS. 1, 2A-2B, 4A-4D, and 5A-5D, each having at least one different tendon engaging surface.

FIGS. 4A-4D are views of a fourth comparative bone block-tendon assembly comprising two bone blocks that sandwich a tendon, the first bone block having a textured pattern (saw-tooth pattern of ridges) on its tendon engaging surface (FIG. 6A) while the second bone block is an intermediate bone block of the present invention having an a smooth tendon engaging (compressing) surface that is interrupted by two channels with rectangular cross-sections running the length of the bone block, which is in the direction of pull of the tendon. FIG. 4A is an exploded view of the fourth comparative bone block assembly. FIG. 4B is a side view of the assembled fourth comparative bone block assembly. FIG. 4C is an end view FIG. 4D is a detailed view of the tendon and bone blocks from FIG. 4A showing the lengthwise channels having a rectangular cross-section in the intermediate bone block of the present invention. This fourth comparative bone block-tendon assembly was tested for average load to failure (Newtons) in Table 1 relative to bone block-tendon assemblies of FIGS. 1, 2A-2B, 3A-3B and 5A-5D, each having at least one different tendon engaging surface.

FIGS. 5A-5D are views of a fifth comparative bone block-tendon assembly comprising two bone blocks that sandwich a tendon, the first bone block having a textured (saw-tooth) pattern of ridges on its tendon engaging surface (FIG. 6A) while the second bone block is a preferred intermediate bone block of the present invention having an a smooth tendon engaging (compressing) surface that is interrupted by two channels with omega cross-sections running the length of the bone block (FIG. 11A), which is in the direction of pull of the tendon. FIG. 5A is an exploded view of the fifth comparative bone block assembly. FIG. 5B is a side view of the assembled fifth comparative bone block assembly. FIG. 5C is an end view FIG. 5D is a detailed view of the tendon and bone blocks from FIG. 5A showing the lengthwise channels having a rectangular cross-section in the intermediate bone block of the present invention. This fifth comparative bone block-tendon assembly was tested for average load to failure (Newtons) in Table 1 relative to bone block-tendon assemblies of FIGS. 1, 2A-2B, 3A-3B, and 4A-4D, each having at least one different tendon engaging surface.

FIGS. 6A-6D show various views of the textured bone block used in the assemblies of FIGS. 2-5, wherein the texture was a saw-tooth pattern of ridges on the tissue (e.g., tendon) engaging surface. FIG. 6A is a perspective view of the textured bone block. FIG. 6B is a top view of the textured bone block looking directly down at the saw-tooth pattern of ridges on the (soft) tissue engaging surface. FIG. 6C is a side view of the textured bone block showing the pattern of ridges appearing from this perspective as angled teeth on the tissue engaging surface. FIG. 6D is a detail view of the saw-tooth pattern as shown on the textured surface in FIG. 6C.

FIGS. 7A-7D show various views of another embodiment of a textured bone block, wherein the texture is a pattern of ridges and valleys on the soft tissue (e.g., tendon) engaging surface. FIG. 7A is a perspective view of the textured bone block. FIG. 7B is a top view of the textured bone block looking directly down at the pattern. FIG. 7C is a side view of the textured bone block showing the pattern of ridges and valleys on the soft tissue (e.g., tendon) engaging surface. FIG. 7D is an end view of the textured bone block of FIG. 7A.

FIGS. 8A-8D show various views of one embodiment of an intermediate bone block of the present invention having channels with a square cross section running across the intended direction of pull (arrow) of a segment of soft tissue (e.g., tendon). FIG. 8A is a perspective view of the intermediate bone block. FIG. 8B is a top view of the intermediate bone block looking directly down at the layout (pattern) of channels. FIG. 8C is a side view of the intermediate bone block showing the shape and pattern of cavities (e.g., channels) and tissue compressing surfaces. FIG. 8D is an end view of the intermediate bone block of FIG. 8A.

FIGS. 9A-9D show various views of one embodiment of an intermediate bone block of the present invention having channels running across the intended direction of pull (arrow) of a segment of soft tissue (e.g., tendon). The channels are similar to those in FIGS. 8A-8D except that the bottom edges of the channels have a radius (R) edge. FIG. 9A is a perspective view of the intermediate bone block. FIG. 9B is a top view of the intermediate bone block looking directly down at the pattern of channels. FIG. 9C is a side view of the intermediate bone block showing the pattern of cavities (e.g., channels) and tissue compressing surfaces. FIG. 9D is an end view of the intermediate bone block of FIG. 9A.

FIGS. 10A-10D show various views of another embodiment of an intermediate bone block of the present invention having channels with a "V" shaped cross section running across the intended direction of pull (arrow) of a segment of soft tissue (e.g., tendon). FIG. 10A is a perspective view of the intermediate bone block. FIG. 10B is a top view of the intermediate bone block looking directly down at the layout (pattern) of channels. FIG. 10C is a side view of the intermediate bone block showing the pattern of cavities (e.g., channels) and tissue compressing surfaces. FIG. 10D is an end view of the intermediate bone block of FIG. 10A.

FIGS. 11A-11D show various views of one embodiment of an intermediate bone block of the present invention having channels with an omega-shaped cross section running substantially in the intended direction of pull (arrow) of a segment of soft tissue (e.g., tendon). FIG. 11A is a perspective view of one embodiment on an intermediate bone block having channels with an omega shaped cross section. FIG. 11B is a top view of the intermediate bone block looking directly down at the lengthwise pattern of channels. FIG. 11C is a side view of the intermediate bone block showing the pattern of cavities (e.g., parallel channels) and tissue compressing surfaces. FIG. 11D is an end view of the intermediate bone block of FIG. 11A. If the block of FIG. 11D is rotated 180° in the plane of the paper, the omega shape of channel 117 becomes more apparent.

FIGS. 12A-12D show various views of another embodiment of an intermediate bone block of the present invention having a layout of channels with an omega-shaped cross section running substantially in the intended direction of pull (arrow) of a segment of soft tissue (e.g., tendon). The intermediate bone block of this embodiment differs from that shown in FIGS. 11A-11D because the present embodiment has a broken edge 128. Preferably, this reduction of the end of the tendon engaging face results in an internal leading edge configuration that reduces tissue stresses during assembly and use. FIG. 12A is a perspective view of one embodiment on an intermediate bone block having channels with an omega-shaped cross section. FIG. 12B is a top view of the intermediate bone block looking directly down at the substantially parallel layout of channels. FIG. 12C is a side view of the intermediate bone block showing the pattern of cavities (e.g., parallel channels) and tissue compressing surfaces. FIG. 12D is an end view of the intermediate bone block of FIG. 12A. If the block of FIG. 12D is rotated 180° in the plane of the paper, the omega shape of channel 127 becomes more apparent.

FIGS. 13A-13D show various views of yet another embodiment of an intermediate bone block of the present invention having a layout of channels with an omega-shaped cross section running substantially across the intended direction of pull (arrow) of a segment of soft tissue (e.g., tendon). FIG. 13A is a perspective view of one embodiment on an intermediate bone block having channels with an omega-shaped cross section. FIG. 13B is a top view of the intermediate bone block looking directly down at the pattern of channels. FIG. 13C is a side view of the intermediate bone block showing the pattern of cavities (e.g., channels) and tissue compressing surfaces. If the block of FIG. 13C is rotated 180° in the plane of the paper, the omega shape of channel 137 becomes more apparent. FIG. 13D is an end view of the intermediate bone block of FIG. 13A.

FIGS. 14A-14D show various views of yet another embodiment of an intermediate bone block of the present invention having a plurality of channels with different sized omega-shaped cross sections running substantially across the intended direction of pull (arrow) of a segment of soft tissue (e.g., tendon). FIG. 14A is a perspective view of this embodiment on an intermediate bone block. FIG. 14B is a top view of the intermediate bone block looking directly down at the pattern of channels. FIG. 14C is a side view of the intermediate bone block showing the pattern of cavities (e.g., channels) and tissue compressing surfaces. If the block of FIG. 14C is rotated 180° in the plane of the paper, the omega shape of each of different sized channels 147A, 147B and 147C becomes more apparent. FIG. 14D is an end view of the intermediate bone block of FIG. 14A.

FIGS. 15A-15D show various views of yet another embodiment of an intermediate bone block of the present invention having a layout of channels with an omega-shaped cross section running substantially across the intended direction of pull (arrow) of a segment of soft tissue (e.g., tendon) and channels with an omega-shaped cross section running substantially in the intended direction of pull (arrow) of a segment of soft tissue (e.g., tendon). FIG. 15A is a perspective view of one embodiment on an intermediate bone block having channels with an omega-shaped cross section. FIG. 15B is a top view of the intermediate bone block looking directly down at the criss-crossing pattern of channels. FIG. 15C is a side view of the intermediate bone block showing the pattern of cavities (e.g., channels) and tissue compressing surfaces. FIG. 15D is an end view of the intermediate bone block of FIG. 15E also showing the omega cross-section of the channels. If the views of FIGS. 15C and 15D are rotated 180° in the plane of the paper, the omega cross-sectional shape of channels 157B and 157A, respectively becomes more apparent.

FIGS. 16A-16D show various views of yet another embodiment of an intermediate bone block of the present invention having a plurality of channels with omega-shaped cross sections running substantially across the intended direction of pull (arrow) of a segment of soft tissue (e.g., tendon). FIG. 16A is a perspective view of this embodiment on an intermediate bone block. FIG. 16B is a top view of the intermediate bone block looking directly down at the "V" shaped layout of the channels. FIG. 16C is a side view of the intermediate bone block showing the pattern of cavities (e.g., channels) and tissue compressing surfaces. If the block of FIG. 16C is rotated 180° in the plane of the paper, the omega shape of the channels 167 becomes more apparent. FIG. 16D is an end view of the intermediate bone block of FIG. 16A.

FIGS. 17A-17D show various views of a preferred embodiment of an intermediate bone block of the present invention having a plurality of channels with omega-shaped cross sections running substantially in the intended direction of pull (arrow) of a segment of soft tissue (e.g., tendon) and having a component that runs across the direction of intended pull of the segment of soft tissue. FIG. 17A is a perspective view of this embodiment on an intermediate bone block. FIG. 17B is a top view of the intermediate bone block of FIG. 17A looking directly down at the stacked triple "U" shaped (or double stacked "A") layout of the channels. FIG. 17C is a side view of the intermediate bone block showing the pattern of cavities (e.g., channels) and tissue compressing surfaces. If the block of FIG. 17C is rotated 180° in the plane of the paper, the omega shape of the channels 177 becomes more apparent. FIG. 17D is an end view of the intermediate bone block of FIG. 17A.

FIGS. 18A-18D show various views of one embodiment of an intermediate bone block of the present invention having channels with an omega-shaped cross section running substantially in the intended direction of pull (arrow) of a segment of soft tissue (e.g., tendon), and having a textured saw tooth pattern of ridges on the tissue engaging surface. FIG. 18A is a perspective view of this embodiment on an intermediate bone block showing the ridges on the soft tissue engaging surface angled to engage the soft issue in the direction of pull. FIG. 18B is a top view of the intermediate bone block looking directly down at the pattern of channels. FIG. 18C is a side view of the intermediate bone block showing the pattern of cavities (e.g., substantially parallel channels) and tissue compressing surfaces (ridges). FIG. 18D is an end view of the intermediate bone block of FIG. 18A. If the block of FIG. 18D is rotated 180° in the plane of the paper, the omega shape of channel 187 becomes more apparent.

FIGS. 19A-19D show a series of views of the external profile of one embodiment of an intermediate bone block of the present invention. FIGS. 19A-19D are essentially views of the flip side of the intermediate bone block of FIGS. 11A-11D, respectively, wherein all outside edges were rounded to have a radius. FIG. 19A is a perspective view of one embodiment of an intermediate bone block wherein each outside edge (i.e., non-soft tissue contacting edge) is a radius edge. FIG. 19B is a top view of the intermediate bone block 190 of FIG. 19A, showing that all corners are rounded corners of a defined radius. FIG. 19C is a side view of the bone block 190 of FIG. 19A, showing the radius edge R1 and showing as a broken line the internal omega shaped channel running the length of the bone block. FIG. 19D is an end view of the intermediate bone block of FIG. 19A viewed from its end 194 and looking down the length of the two channels 197 having the omega ("Ω") shaped cross section in upright configuration in this perspective.

FIGS. 20A-20D show various views of a semi-capsule shaped embodiment of an intermediate bone block of the present invention having channels with an omega-shaped cross section running substantially in the intended direction of pull (arrow) of a segment of soft tissue (e.g., tendon). FIG. 20A is a perspective view of this embodiment on an intermediate bone block showing holes for receiving a biocompatible pin or other connector that would hold the depicted intermediate bone block to any one of a variety of appropriately shaped opposing bone blocks and a segment of soft tissue sandwiched therebetween. FIG. 20B is a top view of the soft tissue engaging face of this intermediate bone block looking directly down at the pattern of channels and pin holes. FIG. 20C is a side view of the intermediate bone block showing its semi-capsular shape. FIG. 20D is an end view of the intermediate bone block of FIG. 20A. If the block of FIG. 20D is rotated 180° in the plane of the paper, the omega shape of channel 207 becomes more apparent.

FIGS. 21A-21D show various views of the exterior surface of a semi-capsule shaped embodiment of a bone block that can serve as the opposing bone block to the bone block of FIGS. 20A-20D. FIG. 21A is a perspective view of this embodiment of an opposing bone block showing holes for receiving a biocompatible pin or other connector (pin holes) that would hold this bone block to any one of a variety of appropriately shaped intermediate bone blocks (of the present invention) and to a segment of soft tissue sandwiched therebetween. FIG. 21B is a top view of the outside face of this opposing bone block looking directly down at its capsule shape and the position of the pin holes. FIG. 21C is a side view of the opposing bone block showing its semi-capsular shape. FIG. 21D is an end view of the opposing bone block of FIG. 21A. When the bone block of FIG. 21A has channels on its tissue engaging surface (not shown), it becomes an intermediate bone block of the present invention.

FIGS. 22A-22D show various views of the exterior profile of a semi-capsule shaped embodiment of an intermediate bone block of the present invention having channels with an omega-shaped cross section running substantially in the intended direction of pull (arrow) of a segment of soft tissue (e.g., tendon). In practice, this intermediate bone block may mate with the bone block of FIGS. 20A-20D or FIGS. 21A-21D. FIG. 22A is a perspective view of this embodiment on an intermediate bone block showing holes for receiving a biocompatible connector (e.g., pin or other connector) that would hold the depicted intermediate bone block to any one of a variety of appropriately shaped opposing bone blocks and a segment of soft tissue sandwiched therebetween. FIG. 22A also shows that the exterior surface has a curved notch or groove for maximizing engagement with an interference screw. FIG. 22B is a top view of this intermediate bone block looking directly down at the groove and pattern of pin holes. FIG. 22C is a side view of the intermediate bone block showing its semi-capsular shape. FIG. 22D is an end view of the intermediate bone block of FIG. 22A showing the groove having a radius R.

FIGS. 23A-23D show views of yet another alternate embodiment for the exterior surface of an intermediate bone block of the invention. FIG. 23A is a perspective view of this embodiment of an opposing bone block showing holes for receiving a biocompatible connector, e.g., pin or other connector, (pin holes) that would hold this bone block to any one of a variety of appropriately shaped bone blocks and to a segment of soft tissue sandwiched therebetween. Also shown on the exterior surface of this embodiment are ridges suitable for gripping the bone tunnel and reducing slippage in the direction of pull (arrow) of the tendon. FIG. 23B is a top view of the outside face of this intermediate bone block looking directly down at its capsule shape and the position of the pin holes. FIG. 23C is a side view of the opposing bone block showing its semi-capsular shape. FIG. 23D is an end view of the opposing bone block of FIG. 23A. In practice, the semi-capsule shaped intermediate bone block of FIG. 23A can mate with the bone block of FIG. 20A, 21A, 22A or preferably 23A.

FIG. 24A is a perspective view of one embodiment of an assembled BTB of the present invention. In this perspective view, the BTB is composed of two assembled bone block assemblies, one on each of the opposing ends of a segment of soft tissue. Each bone block assembly has at least one intermediate bone block of the present invention as a component thereof. FIG. 24B is a top view of the assembled BTB wherein one embodiment for positioning the bone pins is shown. FIG. 24C is a side view of the assembled BTB clearly showing the soft tissue (e.g., tendon) sandwiched between opposing bone blocks at each end. FIG. 24D is an end view of the assembled BTB clearly showing the soft tissue (e.g., tendon) sandwiched between opposing bone blocks at each end.

FIGS. 25A-25D are views of another embodiment of a BTB of the present invention. FIG. 25A is an exploded perspective view of a preferred embodiment of an assembled BTB of the present invention. In this exploded perspective view, the BTB is composed of two assembled bone block assemblies, one on each of the opposing ends of a segment of soft tissue. Each bone block assembly has at least one intermediate bone block of the present invention as a component thereof. FIG. 25B is a top view of the assembled BTB wherein one embodiment for positioning the bone pins is shown. FIG. 25C is a side view of the assembled BTB clearly showing the soft tissue (e.g., tendon) sandwiched between opposing bone blocks at each end. FIG. 25D is an end view of the assembled BTB clearly showing the soft tissue (e.g., tendon) sandwiched between opposing bone blocks at each end. In this latter view, the bone block-tissue assembly is generally cylindrical, having the approximate diameter of a bone tunnel into which it can be inserted, and a groove for maximizing contact with an interference screw.

FIGS. 26A-26D are views of another embodiment of a BTB of the present invention. FIG. 26A is a perspective view of another embodiment of an assembled BTB of the invention. In this perspective view, the soft tissue (e.g., tendon) is attached to the bone block as in FIG. 24A, but then each of the bone block assemblies is flipped 180° in the plane of the paper such that the segment of soft tissue doubles back over the exterior surface of one of the bone blocks. FIG. 26B is a top view of the assembled BTB wherein only the soft tissue is visible FIG. 26C is cross-sectional side view CC of the assembled BTB clearly showing the soft tissue (e.g., tendon) sandwiched between opposing bone blocks at each end and the presence of the biocompatible bone pins. FIG. 26D is a side view of the assembled BTB clearly showing the soft tissue (e.g., tendon) sandwiched between opposing bone blocks at each end.

FIGS. 27A-27D are views of another embodiment of a BTB of the present invention. FIG. 27A is a perspective view of the BTB of FIG. 26A further comprising a third bone block at each end sandwiching the soft tissue along the exterior of the bone blocks shown in FIG. 27A to produce a 5 layer sandwich assembly at each end comprising layers of bone: soft tissue:bone:soft tissue:bone. FIG. 27B is a top view of the assembled BTB wherein the assembly appears the same as in FIG. 24B. FIG. 27C is cross-sectional side view BB of the assembled BTB, clearly showing three bone blocks sandwiching two portions of the length of soft tissue (e.g., tendon) as those portions in turn sandwich the central bone block. The assembly is held together at each end by biocompatible pins or other connectors. FIG. 27D is a side view of the assembled BTB clearly showing the soft tissue (e.g., tendon) sandwiched between opposing bone blocks at each end.

FIGS. 28A-28D are views of another embodiment of a BTB of the present invention comprising a 5 layer assembly at each end. FIG. 28A is a perspective view of a double tendon BTB comprising layers of bone:soft tissue:bone:soft tissue: bone. FIG. 28B is a top view of the assembled BTB wherein the assembly appears the same as in FIG. 24B. FIG. 28C is a side view of the assembled BTB, clearly showing three bone blocks sandwiching two distinct lengths of soft tissue (e.g., tendon) as those portions in turn sandwich the central bone block. The assembly is held together at each end by biocompatible pins or other connectors. FIG. 28D is an end view of the BTB of FIG. 28A.

FIGS. 29A-29D are views of a dual tendon BTB that is a hybrid of FIGS. 28A and 24A insofar as the bone-tendon assembly at one end is a three layer sandwich and at the opposing end is a five layer sandwich. FIG. 29A is a perspective view of a double tendon BTB comprising 5 layers (bone: soft tissue:bone:soft tissue:bone) at one end and 3 layers (bone:soft tissue:bone) at the opposing end. FIG. 29B is a top view of the assembled BTB wherein the assembly appears substantially the same as in FIG. 24B. FIG. 29C is a side view of the assembled BTB, clearly showing three bone blocks sandwiching two distinct lengths of soft tissue (e.g., tendon) at one end and two bone blocks sandwiching a single length of soft tissue at the opposing end. The assembly is optionally held together at each end by 2-3 biocompatible connectors, e.g., pins or other mechanical connectors. FIG. 29D is an end view of the BTB of FIG. 29A.

FIGS. 30A-30B are side and end views, respectively, of a harvested BTB 300 having a tendon 303 of a first defined length L1 naturally attached at its first end to a first bone block and naturally attached at its second end to a second bone block. FIGS. 30C and 30D are side and end views, respectively, of 2 spacers for reducing the first defined length L1 of tendon 303 to a shorter functional length L2, and optionally, 2 bone blocks for capping the tendon and providing for greater bone to bone contact between the graft and the a bone tunnel in a patient. FIGS. 30E and 30F are side and end views, respectively, of an assembled bone block wherein the length L1 of the tendon in a harvested BTB has been reduced to L2 by assembling a spacer and an intermediate bone block of the invention to each of the naturally attached bone blocks.

FIGS. 31A-31D are views of an alternate embodiment of an intermediate bone block of the present invention. FIG. 31A is a perspective view of one embodiment on an intermediate bone block having a sloped channel of uniform width. FIG. 31B is a top view of the intermediate bone block looking directly down at the central sloped channel. FIG. 31C is a side view of the intermediate bone block showing the slope of the central channel. FIG. 31D is an end view of the intermediate bone block of FIG. 31A looking up the sloping channel.

FIGS. 32A-32D are views of an alternate embodiment of an intermediate bone block of the present invention. FIG. 32A is a perspective view of one embodiment on an intermediate bone block having a converging channel of substantially uniform depth. FIG. 31B is a top view of the intermediate bone block showing the channel converging from the opposing end. FIG. 31C is a side view of the intermediate bone block showing that the channel is of a substantially uniform depth. FIG. 31D is an end view of the intermediate bone block of FIG. 31A looking toward the converging channel at the opposing end.

FIG. 33A is an exploded view of the template showing the upper and lower halves, the locking screws, and the holes for positioning the interference pins prior to impaling them into the templated bone:tendon:bone sandwich locked in position below. FIG. 33B is a perspective view of the assembled template which in this locked position would place a standard amount of tension on the pre-sized bone blocks and soft tissue placed therein prior to insertion of the interference pins. FIG. 33C is a top view of the assembled template. FIG. 33D is a front view of the assembled template showing opening 339 where the segment of soft tissue (e.g., tendon) would extend outside the device. FIG. 33E is a side view of the assembled template.

FIGS. 34A-34D provide views of another embodiment of an assembled BTB of the present invention wherein a single segment of soft tissue (e.g., tendon or ligament) is doubled back to provide a double tendon BTB. FIG. 34A is a perspective view of the assembled BTB of this invention having an intermediate bone block 344 of the present invention sandwiching a tendon between an opposing bone block 346. FIG. 34B is a top view of the BTB where the biocompatible connectors in the top of the opposing bone block are clearly visible. FIG. 34C is a side view showing tendon 343 doubling back on itself. FIG. 34D is view of the proximal end of the BTB in FIG. 34A, showing the bone blocks sandwiching the doubled up tendon.

FIGS. 35A-35D provide views of another embodiment of an assembled BTB of the present invention wherein a single segment of soft tissue (e.g., tendon or ligament) is doubled back to provided a double tendon BTB. This embodiment is a variation of the embodiment of FIG. 34 but further includes two additional bone blocks at the two tendon end to sandwich the tendon and provide for bone to bone contact between the graft and the patient's bone when the graft is implanted in the surgically excised bone tunnel in the patient. FIG. 35A is a perspective view of the assembled BTB of this invention having an intermediate bone block 354 of the present invention sandwiching a tendon between an opposing bone block 356. FIG. 35B is a top view of the BTB where the biocompatible connectors in the top of the opposing bone block-tendon assemblies are clearly visible. FIG. 35C is a side view showing tendon 353 doubling back on itself FIG. 35D is an end view of the BTB at the end where the two bone blocks sandwich the doubled up tendon.

FIGS. 36A-36D are a series of views of another embodiment of an assembled BTB of the present invention. FIG. 36A is a perspective view of an assembled BTB comprising a length of soft tissue having opposing first and second ends, wherein the first and second ends, respectively, of the soft tissue are separately sandwiched between wedge shaped opposing bone blocks, the angle of the wedges being such that in combination, the wedges form a 3 dimensional shape whose opposing longitudinal surfaces are substantially parallel. Thus, the opposing faces of the bone blocks contain a lengthwise tapering profile. FIG. 36B is a top view of this embodiment of assembled BTB. FIG. 36C is a side view of this embodiment of assembled BTB showing the assembly details and the use of suitable biocompatible connectors. FIG. 36D is an end view of the proximal end of the assembled BTB as positioned in FIG. 36A.

FIGS. 37A-37D show various views of the exterior profile of a preferred semi-capsule shaped embodiment of an intermediate bone block of the present invention having a sawtooth pattern of striations 371 on the tissue (e.g., tendon) engaging surface. FIG. 37A is a top view of this embodiment of an intermediate bone block showing holes 372A-372C for receiving a biocompatible pin or other connector that would hold the depicted intermediate bone block to any one of a variety of appropriately shaped opposing bone blocks and a segment of soft tissue sandwiched therebetween. FIG. 37B is a perspective view showing that the exterior surface of this embodiment of an intermediate bone block has a curved notch or groove 373 for maximizing engagement with an interference screw. FIG. 37C is a side view of the intermediate bone block showing its semi-capsular shape. FIG. 37D is an end view of the intermediate bone block of FIG. 37A. FIG. 37E is a detail view of the saw-tooth pattern as shown on the textured surfaces in FIGS. 37A-37D.

FIGS. 38A-38D show various views of the exterior profile of another preferred semi-capsule shaped embodiment of an intermediate bone block of the present invention having a plurality of channels with omega-shaped cross sections running substantially in the intended direction of pull of a segment of soft tissue (e.g., tendon) and having a component that runs across the direction of intended pull of the segment of soft tissue. FIG. 38D is a top view of the intermediate bone block looking directly down at the stacked triple "U" shaped (or double stacked "A") layout of the channels. FIG. 38C is a perspective view of this embodiment on an intermediate bone block showing a notch 384 cut out of the intermediate bone block. FIG. 38B is a side view of this embodiment of an intermediate bone block showing it semi-capsular shape. FIG. 38A is an end view of the intermediate bone block of FIG. 38D, in which the omega ("Ω") shape of the channels 382 becomes more apparent.

FIGS. 39A-39D provide views of another embodiment of an assembled BTB of the present invention wherein a single segment of soft tissue (e.g., tendon or ligament) 392 is gripped by a first bone block assembly at the first end of the BTB and is doubled back through a second bone block assembly 393 at the second end of the BTB to provide a double tendon BTB. FIG. 39A is a side view of the embodiment of a BTB. FIG. 39B is an end view of this embodiment of a BTB of the present invention as viewed looking from the tip of the bone block assembly 393 at the second end of the BTB. FIG. 39C is a side view of the embodiment of a BTB showing the top of bone block assembly 391. FIG. 39D is a perspective view of this embodiment showing the second end of the soft tissue wrapped under the bottom of bone block assembly 391.

FIG. 40A is a top view of the tissue engaging surface 403 of the intermediate bone block. FIG. 40B is a perspective view of this embodiment on an intermediate bone block showing a notch 405 cut out of the intermediate bone block. FIG. 40C is a side view showing the semi-capsular shape of the intermediate bone block. FIG. 40D is an end view of the intermediate bone block in which the "U" shape of the channel or groove becomes more apparent.

FIGS. 41A-41D provide views of another embodiment of an assembled BTB of the present invention wherein the distal end of a single segment of soft tissue (e.g., tendon or ligament) 413 is gripped by a first bone block assembly 411 at the first end of the BTB and is doubled back through a second bone block 412 at the second end of the BTB to provide a double tendon BTB. FIG. 41A shows a side view of this embodiment. FIG. 41B shows an end view of this BTB embodiment. FIG. 41C is a top view of a BTB wherein portal 418 is shown through which the soft tissue passes. FIG. 41D is a perspective view showing soft tissue threaded through a portal in the bone block at the second end of a BTB and having the proximal end of the soft tissue wrap under the bone block assembly at the first end of the BTB.

FIGS. 42A-42D provide views of one embodiment of an intermediate bone block. FIG. 42A is a top view of this embodiment. FIG. 42B is an end view of this embodiment. FIG. 42C is a side view of this embodiment. FIG. 42D is a perspective view of this embodiment.

FIGS. 43A-43D provide views of one embodiment of an intermediate bone block. FIG. 43A is a top view of this embodiment. FIG. 43B is an end view of this embodiment. FIG. 43C is a side view of this embodiment. FIG. 43D is a perspective view of this embodiment.

FIGS. 44A-44D provide views of one embodiment of an intermediate bone block. FIG. 44A is a top view of this embodiment. FIG. 44B is an end view of this embodiment. FIG. 44C is a side view of this embodiment. FIG. 44D is a perspective view of this embodiment.

Figure 24A:
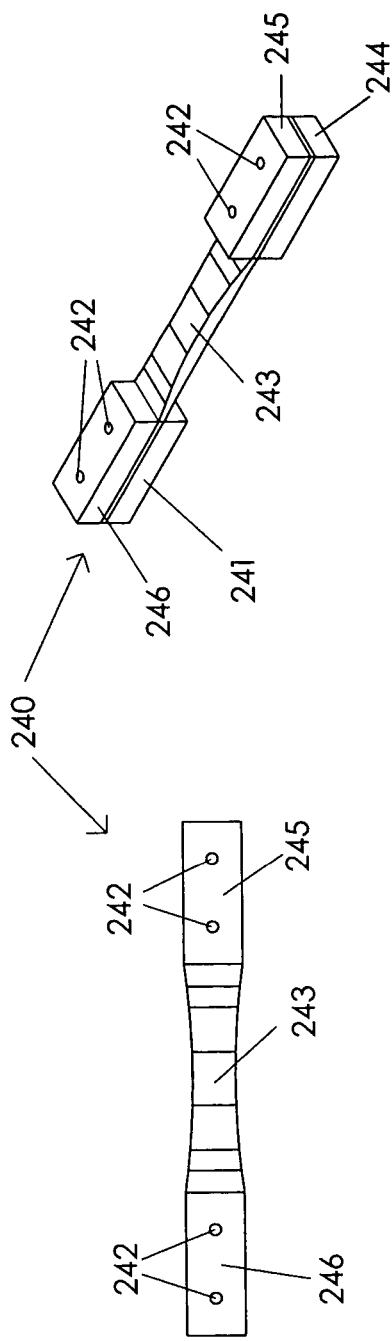
FIGS. 24A-24D are various views of one embodiment of a BTB of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

The present invention has multiple aspects. In its simplest aspect, the present invention is directed to an intermediate bone block comprising a machined segment of cortical bone, cancellous bone, artificial bone or a combination thereof, the intermediate bone block having a face comprising one to ten compression surfaces and one to ten cavities, the compression surfaces suitable for compressing soft tissue, the one to ten cavities suitably sized for receiving uncompressed soft tissue and/or the compressed soft tissue that is being squeezed from adjacent compression surfaces. Preferably, the bone block is cortical bone or cancellous bone or a combination thereof. More preferably, the bone block is cortical bone. While engineering an assembled BTB, the Applicants discovered that combining the compressive surfaces of a bone block with one to ten cavities on the tendon engaging surface of a the bone block, allows the uncompressed soft tissue and the overflow of the compressed soft tissue to flow into the cavities. The Applicants discovered that both the presence of the cavities on the tendon engaging faces of the bone blocks and the cross-sectional shape and layout of the cavities contributed to the overall grip of the bone blocks to the soft tissue sandwiched between tendon engaging faces of independent opposing bone blocks.

The cavities are preferentially channels cut into the tendon engaging face of the bone blocks. Applicants discovered that the channels unexpectedly increase the grip of the tendon between the bone blocks. It is thought that the cavities (preferably, channels) capture uncompressed soft tissue (e.g., tendon) and the overflow of the adjacent compressed tissue allowing the compressive surfaces of the bone block to grab and hold the tissue rather than float on it. It was unexpectedly discovered that when the cross-sectional shape of the cavities is an omega shape, the maximum gripping of the tendon between the opposing bone blocks is achieved. It is believed that the omega shaped cross section advantageously captures and holds the uncompressed and overflow soft tissue. Specifically, the omega shaped cavity (preferably, channel) has a narrower mouth than the body of the cavity (channel) because the tendon engaging face of the bone block is undercut. This feature allows the soft tissue to enter the cavity and expand in a direction opposite to the direction of the compressed soft tissue immediately above on the surface of the bone block. The rounded omega profile also eliminates stress concentrations and allows the soft tissue to expand and distribute the compressive load evenly across the entire cavity. This controlled expansion and even distribution of load occurs without compromising the internal structure and related natural properties of the soft tissue. As a result, the omega cavity gently grips the soft tissue without cutting, and prevents it from slipping, sliding or flowing in the direction it is being pulled or squeezed. Moreover, unlike teeth, the edge of the omega cavity only exerts force when needed in response to being pulled or squeezed. In addition, the narrow mouth of the omega cavity (or channel) on the bone block surface maximizes contact between the bone block surface (tendon engaging surface) and the tendon, and thus maximizes grip.

In a preferred intermediate bone block of the present invention, the one to ten cavity(ies) have an undercut cross-sectional profile. By the term "undercut" is meant that the cavities open up to be wider than their surface opening, much like a doorway opening into a wider room. Two examples of an "undercut cross-sectional profile" are an omega cross-sectional profile or a blunted triangular cross-sectional profile (like an opening for receiving a dovetail). An preferred cavity is a channel, more preferably a channel with an undercut profile, most preferably, a channel that has an omega cross-sectional profile.

The intermediate bone block of the present invention has a plurality of uses and can be used with an identical bone block, a different bone block of the present invention, or a bone block of the prior art, to enhance the grip upon any soft tissue that engages its soft tissue (e.g., tendon) engaging surface. Thus, the intermediate bone block of the present invention is a versatile and functional component that can be combined with other components to form a plurality of different bone block assemblies suitable for binding to a soft tissue to form an implantable graft suitable for repair of a defect or injury in the body of a mammalian patient. A particularly preferred graft is a bone-tendon-bone graft. This graft is described in more detail below.

By the term "mammalian" patients is meant humans, domesticated animals and zoological specimens. Typical domesticated mammals are dogs, cats, horses, goats, sheep, pigs, llamas, and cattle. The bone source for the intermediate bone block of the present invention is autograft, allograft, xenograft, or artificial bone. However, because the intermediate bone block is machined, it is typically allograft, xenograft, or artificial bone. Preferably, the bone source is allograft or xenograft bone. When the recipient patient is a human, the bone source is preferably human allograft bone. Due to constraints of human allograft availability and current advances in the use and processing of xenografts, there are also some cases where the bone source is preferably xenograft bone, and more preferably xenograft bone treated to reduce antigenicity and immune response.

The soft tissue is typically a collagenous material that is autograft, allograft or xenograft. Alternatively, the soft tissue may be a natural or synthetic material. Preferably, the soft tissue is a predetermined length of tendon, a bundle of tendons of the same or different lengths, a predetermined length of ligament, a bundle of ligaments of the same length or different lengths, a segment or segments of pericardium, dermis, fascia, dura, skin, submucosal tissue (e.g., intestinal tissue), cartilage, or a combination thereof. Typically, the source of the soft tissue is autograft, allograft, or xenograft. Most typically, the source of the soft tissue is allograft or xenograft. When the recipient patient is a human, the source is preferably human allograft. However, in some situations, particularly in tendon repair, a tendon bundle comprising a xenograft tendon bundle or a combination of allograft and xenograft tendons of different thicknesses and lengths, provides for enhanced performance under extreme stresses. This combination is discussed further herein in relation to an assembled bone-tendon-bone implant of the present invention To make an omega-shaped cavity, the surface is undercut with a ball mill to produce a cavity that has a greater interior width than the surface opening. The cavities with the omega cross section preferably run as one or more independent or intersecting channels on the soft tissue engaging surface of the intermediate bone block. See FIGS. 11-18. In one embodiment, the layout of one or more of the channels across the soft tissue-engaging surface is linear across the face of the intermediate bone block. See FIGS. 11A-11D. In another embodiment, one or more of the channels is laid out to form a "V"-shaped channel (when viewed from above) across the soft tissue-engaging surface of the intermediate bone block. See FIGS. 16A-16D. In yet another embodiment, the layout of channels can form a series of "V"s across the soft tissue-engaging surface. In yet another embodiment, one of the omega channels is laid out as a W-shaped channel (when viewed from above) across the tissue-engaging surface of the intermediate bone block. The omega cross section can be made by precision milling parallel to the surface of the intermediate bone block with a ball shaped end mill, such that the tool removes some of the surface bone but primarily undercuts bone just below the surface. Such a tool is available from Dremel, Racine Wis. Another means for making the omega cross section is to use a router and the appropriate bit or bits. Because a router can be easily templated to switch directions, it is most convenient for laying out channels that switch directions across the face of the bone block, such as the "A," "U," "V" and "W" layout of channels having an omega cross section.

In a second aspect, the present invention is directed to a bone block assembly comprising an intermediate bone block of the present invention in combination with a second bone block. The second bone block can be the same or different than the intermediate bone block as the advantages of the present invention accrue from Applicants' intermediate bone block having an overflow cavity, as described herein, being present on a single bone block. In the bone block assembly, the intermediate bone block and the second bone block are machined to receive 1 to 30 biocompatible connectors. As will be discussed later herein, these biocompatible connectors include any connectors capable of holding the intermediate bone block and the second bone block (i.e., the bone block assembly) together as a unit.

In a third aspect, the present invention is directed to a bone block assembly comprising a first intermediate bone block of the present invention in combination with 2-10 other bone blocks, providing bone block assemblies containing 3-10 bone blocks. The 2-10 other bone blocks can be the same or different than the first intermediate bone block as the advantages of the present invention accrue from an omega cavity being present on a single intermediate bone block. The 3-10 intermediate bone blocks can have various configurations for sandwiching soft tissue. See e.g. FIGS. 27, 28 and 29. In these bone block assemblies, the intermediate bone blocks are also machined to receive 1 to 30 biocompatible connectors.

In a fourth aspect, the present invention is directed to an assembled bone-tendon-bone (BTB) implant comprising a bone block assembly of the present invention affixed to one or both ends of a length or a bundle of soft tissue. When the assembled BTB of the present invention has a bone block assembly of the present invention at only one end of the soft tissue, the opposing end of soft tissue may be free (e.g., free tendon end) or the bone block at the second and opposing end of the soft tissue is a naturally occurring bone block or portion of bone. Methods for obtaining a tendon that is naturally attached to a block of bone is disclosed commonly assigned U.S. Pat. No. 6,497,726, entitled "Materials and methods for improved bone tendon bone transplantation" which issued on Dec. 24, 2002, and in commonly assigned U.S. Pat. No. 6,805,713, entitled "Materials and methods for improved bone tendon bone transplantation" which issued on Oct. 19, 2004, both of which are expressly incorporated herein by reference in relation to their disclosure on BTBs and on obtaining a tendon naturally attached to a bone block. When the assembled BTB of the present invention has a bone block assembly of the present invention on each of its ends, the bone block assemblies may be the same or different. In this embodiment, the soft tissue is a length of tendon, a bundle of tendons of the same or different lengths, a length of ligament, a bundle of ligaments of the same length or different lengths, a segment or segments of pericardium, dermis or fascia, or a combination thereof. Preferably, the soft tissue is a length of tendon or ligament or a bundle of tendons or ligaments of the same length or different lengths, or a combination thereof. It is also within the scope of the present invention that the tendons or ligaments or both in the bundles be of the same thickness or of different thicknesses. In the bundles, the tendons, or ligaments or both are allograft, xenograft, synthetic, artificial ligament scaffolds or a combination thereof. Preferably, the tendons are allograft or xenograft. It is also within the scope of the present invention that the intermediate bone block, the second bone block or both may themselves be independently constructed from 1 to 30 bone portions, preferably from 1-10 bone portions, more preferably from 1 to 5 bone portions, even more preferably 1 to 3 bone portions, most preferably from 1 to 2 bone portions.

As used herein, the "T" component of the BTB is intended to refer to a length of tendon, a bundle of tendons of the same or different lengths, a length of ligament, a bundle of ligaments of the same length or different lengths, a segment or segments of pericardium, dermis, fascia, dura, skin, submucosal tissue (e.g. intestinal tissue), cartilage, or a combination thereof. Bundles refer to 1-10 discrete tendons or ligaments, which themselves can be made up of smaller fibers of tendons/ligaments that are stapled, glued, sutured, woven or braided. Alternatively, tendons or other soft tissues are crosslinked with a crosslinking agent. In another alternate embodiment, the segment of soft tissue is sufficiently large so that excess tissue extends beyond the end or sides of the bone block assembly. This excess soft tissue is useful for surgical placement and/or fixation. As used herein, the "T" component or the BTB may also contemplate an engineered construct of natural or synthetic origin, such as a synthetic ligament repair scaffold, other flexible synthetic biomaterial, or specially formulated natural material such as that disclosed in the applicant's copending applications U.S. Ser. No. 10/754,310, entitled "Matrix Composition For Human Grafts/Implants" and filed Jan. 9, 2004, and in U.S. Ser. No. 10/793,976, entitled "Muscle-Based Grafts/Implants" and filed Mar. 5, 2004. Engineered constructs include, for example, processed collagen-based tissue matrix, such as the product sold under the trade name GraftJacket®, by Wright Medical Technology, Inc., Arlington, Tenn.

When the assembled BTB of the present invention has a bone block assembly of the present invention on the opposing ends of the soft tissue, the bone block assemblies may be the same or different. In this embodiment, the soft tissue is a length of tendon, a bundle of tendons of the same or different lengths, a length of ligament, a bundle of ligaments of the same length or different lengths, a segment or segments of pericardium, dermis, fascia, dura, skin, submucosal tissue (e.g. intestinal tissue), cartilage, or a combination thereof. Preferably, the soft tissue is a length of tendon or ligament or a bundle of tendons or ligaments of the same length or different lengths, or a combination thereof.

By selecting a bundle of tendons or ligaments of different length, or a combination thereof, the assembled BTB of the present invention can be tailored to the needs of the patient. For example, when two of the shorter ligaments stretch under strain to the length of one or more longer ligaments, the restraint posed by the longer ligaments engages and acts to stabilize the joint. See, e.g., FIG. 28A-D. By having a BTB with two to four lengths of ligament, tendon or a combination thereof, a reconstructed tendon can have multiple fall back positions to stabilize a joint. This effect can also be achieved by utilizing assemblies that contain 3 or more bone blocks. See, e.g., FIGS. 28A-D & 29A-D. Alternatively, multiple tendons can be designed to have multiple points of attachment or rotation, mimicking the structure and function of the multi-bundled native anterior cruciate ligament (ACL) construct.

Such construction is particularly useful for anterior cruciate reconstruction in a human knee joint. By varying the number and length of ligaments or tendons in a bundle, an assortment of BTBs can be made that would be customized and suitable for a range of patients from the 65-year-old recreational shuffleboard enthusiast to the 25 year old star professional football running back.

It is also within the scope of the present invention that the tendons or ligaments or both in the bundles are of the same cross-sectional area or of different cross-sectional area. In the bundles, the tendons, or ligaments or both are allograft, xenograft or a combination thereof. Preferably, the tendons are allograft.

Additionally, in some cases an entire BTB comprising a combination of allograft, xenograft, synthetic or artificial tissues offers advantages in strength, fixation, mechanical properties, biochemical properties, healing, design freedom and/or availability. In one embodiment, a BTB is constructed of synthetic or allograft or autograft tendon, with a xenograft bone block assembly at one or both ends. In another embodiment, a BTB is constructed of artificial or allograft bone with xenograft tendons. In yet another embodiment, an allograft tendon is attached to a conventional bone block by a naturally occurring attachment at one end, and attached to a xenograft or artificial bone block assembly at the other end. In yet another embodiment, a combination of allograft and xenograft tendons is assembled with a combination of allograft or xengraft or synthetic bone blocks.

Finally, it is also within the scope of the present invention that the intermediate bone block, the second bone block or both are independently constructed or assembled from 1 to 30 bone portions, preferably from 1-10 bone portions, more preferably from 1 to 5 bone portions, even more preferably from 1 to 3 bone portions, most preferably from 1 to 2 bone portions. The bone portions are cortical bone, cancellous bone, artificial bone or a combination thereof. Preferably, the bone block portions are cortical bone, cancellous bone or a combination thereof. More preferably, the bone block portions are cortical bone. Typically, a majority of the bone portions are cortical bone.

By way of example, 30 planks of cortical bone 1 mm in width are stacked right to left with their ends in the direction of pull of the tendon. With the planks being held in juxtaposition to one another, from 2 to 10 through holes of a predetermined diameter are precision drilled across the width of the 30 stacked planks. Typically, the width of the through holes is from about 1 mm to about 2 mm. Into each of the through holes is then inserted an appropriately shaped biocompatible connector that has an interference fit with the through-hole As noted above, the bone block assemblies of the present invention are affixed to the end of a predetermined length of soft tissue (e.g., tendon) by 1 to 30 biocompatible connectors that engage each of the two opposing bone blocks and the tendon that is sandwiched therebetween. The term "biocompatible connector" includes but is not limited to a pin, screw, suture, staple, rivet, strap, nail, band, adhesive, or chemical cross linker. The biocompatible connector may be made from: metal, polymer, bone or other biologics including connective tissues. It is understood that when discussing sutures, adhesives, cross linkers, and other continuous or non-unitary biocompatible connectors, that a single application of the biocompatible connector type may contain multiple smaller units. For example, a single suture connection can be fabricated by stitching a plurality of sutures, e.g., 10 to 100 small individual sutures, and a single adhesive connection may be made by applying a plurality of drops of adhesive, e.g., 10 to 100 small individual drops of adhesive. A suitable biocompatible connector is pin that is press fitted into a hole machined in the bone block. A typical pin is made from stainless steel, titanium, or cortical bone. A preferred pin is a cortical bone pin (i.e., a pin made from cortical bone). Interference fit cortical bone pins are preferred over the alternative biocompatible connector types listed above because they offer a strong and predictable fixation, are readily manufactured, incorporate and heal into the body, are simple to assemble, integrate easily into most graft designs and have minimal regulatory or safety risks.

It is desirable to have a tight and accurate interference fit between the pin(s) and the hole(s) in bone pieces that are connected by the pin(s). The target range for the pin in such an interference fit is 0.001 inches (0.0254 mm) to 0.003 inches (0.0762 mm) larger than the hole diameter, and is pressed fit into place. However, when the pin is made from cortical bone, it has been learned that freeze-drying the bone pins and other bone pieces exerts a disproportionate shrinkage upon the pins compared to the hole diameters. That is, the pin shrinks slightly more than the hole shrinks. Uncorrected, this would result in a less accurate, and less acceptable, interference fit.

The following method can to solve this problem. A bone pin, preferably of cortical bone, of a desired diameter is vacuum dried for at least five hours. This drying is preferably at room temperature and at a negative pressure of approximately 100 milliTorre. This pre-treatment results in a shrinkage of approximately 80 percent of the total shrinkage that would occur in freeze drying. The pin diameter is measured, and a hole is made in the portions to be assembled using an appropriately sized drill bit. The target size for the hole is 0.002 inches (0.0508 mm) to 0.0025 inches (0.0635 mm) smaller than the post-vacuum-drying pin diameter. Preferably, prior to this drilling, the bone portions to be assembled have been kept saturated with moisture to maintain a consistent size and subsequent shrinkage percent. After all holes are drilled, the pin(s) are press fitted into the through holes, machined into an intermediate bone block of the present invention (or into a second bone block), and then freeze dried. The resulting assembled allografts have been found to have interference fits in the desired target range. This method is applicable to the various embodiments described in this disclosure. Where the bone pins are not freeze dried, it is sufficient to dip them in alcohol to facilitate their insertion (press fitting).

To be suitable for implantation in humans, the bone block and soft tissue of the present invention must be treated to remove any antigenic proteins, which may generate a rejection of the implant. It also must be treated to remove any bacteria and viruses. Suitable processes for removing antigenic proteins and sterilizing to neutralize any bacteria and viruses are known in the art. See U.S. Pat. No. 5,846,484, entitled "Pressure flow system and method for treating a fluid permeable workpiece such as a bone," which issued to Scarborough, et al. on Dec. 8, 1998. In the present case, the applicants utilized the assignees' well known method for defatting tissue, which also has the added benefit of removing blood, cellular debris, and soluble and antigenic proteins, by subjecting the muscle tissue to alternating cycles of pressure and vacuum in the sequential presence of solvents, such as isopropyl alcohol, hydrogen peroxide and a detergent. These assignee's processes also neutralize any bacteria and viruses. These processes are disclosed in full detail in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety.

An improved process for cleansing (treating) soft tissues (and bone) for implantation, while preserving the desirable traits of flexibility and strength in the soft tissue, is disclosed in commonly assigned U.S. patent application Ser. No. 10/828,653, entitled "Process and Apparatus for Treating Implants Comprising Soft Tissue," in the name of Mills et al., filed Apr. 20, 2004, which is hereby incorporated by reference for its disclosure on such process for cleansing.

The various aspects of the present invention can best be understood by reference to the drawings. FIGS. 1, 2A-B, 3A-B, 4A-D and 5A-D provide comparative drawings of the bone-block tendon assemblies (BTAs) that were tested in triplicate (n=3) for average (mean) load to failure in Newtons as reported in Table 1.

TABLE 1

| FIG. No. showing the Bone block-Tendon assembly | Description of the tendon engaging surfaces of the two Bone Blocks of the Bone Block-Tendon Assembly | Average Load to Failure Newtons (n = 3) |
|---|---|---|
| 1 | Flat-Flat | 260 N |
| 2 | Flat-Textured* | 344 N |
| 3 | Textured-Textured | 343 N |
| 4 | Textured-Rectangular Channels | 426 N |
| 5 | Textured-Omega Channels | 516 N |

*In all these examples, textured means texture was provided by a saw-tooth pattern.

In Table 1, load to failure was the average of three measurements made on an Instron model 5800 force testing machine, Instron, Canton, Mass. and reflects the amount of force at which the bone block tendon assembly (BTA) failed to retain the tendon when the tendon was pulled opposite the direction of the bone block. In Table 1, a bone block of each of the BTAs of FIGS. 1-5 differed from the prior BTA in the Table solely in the characteristics of one of the tendon engaging surfaces of the two bone blocks that sandwiched the tendon therebetween. In Table 1, the BTA of FIG. 1 had two bone blocks wherein each had a smooth tendon engaging surface. The BTA of FIG. 2A had one bone block with a smooth tendon engaging surface and a second bone block with a tendon engaging surface (FIG. 6A) that was textured with a saw tooth pattern (0.030 inch, or 0.76 mm teeth) that gripped opposite the direction of pull of the tendon. The BTA of FIG. 3A had both a first bone block and a second bone block each of which had a tendon engaging surface (FIG. 6A) that was textured with a saw tooth pattern (0.76 mm teeth) that gripped opposite the direction of pull of the tendon. The BTA of FIG. 4 had one bone block with a tendon engaging surface of the present invention (i.e., having a channel with a cavity with a rectangular cross-sectional area that ran in the direction of pull of the tendon) and a second bone block with a tendon engaging surface (FIG. 6A) that was textured with a saw tooth pattern (0.76 mm teeth) that gripped opposite the direction of pull of the tendon. Finally, the BTA of FIGS. 5A-D had one bone block with a tendon engaging surface (FIG. 11A) of the present invention (i.e., having a channel with an omega cavity that ran in the direction of pull of the tendon) and a second bone block with a tendon engaging surface (FIG. 6A) that was textured with a saw tooth pattern (0.76 mm teeth) that gripped opposite the direction of pull of the tendon.

As reflected in Table 1, the BTA of FIG. 1 with the two opposing smooth tendon engaging surfaces exhibited failure under the lowest load of 260 N (n=3). When one of the bone blocks with the smooth tendon engaging surfaces of FIG. 1 was substituted with a bone block having a frictional engaging surface (i.e., having saw teeth) to produce the BTA of FIG. 2, the average load to failure of the BTA increased by 84 N to 344 N (n=3). However, substituting a second frictional engaging surface having saw teeth for the smooth bone block of FIG. 2 to produce the BTA of FIG. 3 did not produce any incremental gain in average load to failure, i.e., average load to failure remained essentially the same as the BTA of FIG. 2 at 343 N (n=3). However, when one of the frictional engaging surfaces of the BTA of FIG. 3 was substituted with an intermediate bone block of the present invention having a smooth surface that was interrupted by two channels having a rectangular cross-section to produce the BTA of FIG. 4, the average load to failure of the resulting BTA unexpectedly increased by 83 N to 426 N (n=3). When the same frictional engaging surfaces of the BTA of FIG. 3 was substituted with an intermediate bone block of the present invention having a smooth surface that was interrupted by two channels having an omega-shaped cross-section to produce the BTA of FIG. 4, the average load to failure of the resulting BTA unexpectedly increased by 173 N to 516 N (n=3).

Table 2 is compares the mean load to failure of five bone tendon assemblies as a function of the layout or configuration of channels (having an omega cross section) in five intermediate bone blocks of the present invention.

Referring to Table 2, it is apparent that decreasing the surface area of the intermediate bone block of this invention (designs 01-05) surprisingly increases the mean load to failure of the tendon in the bone block-tendon assembly. For example, in going from design 1 (double "I" layout) to design 02 (inverted "U" layout), which involved adding a channel that runs across the direction of pull under the same controlled conditions, there resulted an increase in mean load to failure of 14 N. In going from design 02 (inverted "U" layout) to design 03 (inverted big "U" layout), which involved increasing the width of the channel at the curved base of the "U," there resulted an increase in mean load to failure of 8 N under the same controlled conditions. In going from design 02 (inverted "U" layout) to design 04 ("A" shaped layout), which involved adding a cross channel at about the middle of the block to convert the inverted "U" to an "A" shaped layout, surprisingly increased the mean load to failure by 40 N under the same controlled conditions. Adding a second cross channel to design 04 to produce design 05 (having a double stacked "A" layout (or a triple stacked "U" layout, depending upon your perspective)), further increases the mean load to failure of the tendon in the bone block-tendon assembly by 5 N to 565 N. In each case, the decrease in surface area corresponded to a proportionally larger increase in percent volume removed.

TABLE 2

| Filename | Description | Area of Compression Surface Remaining (mm$^2$)[1] | Percent Compression Surface Remaining (%) | Volume Removed (mm$^3$) | Percent Volume Removed (%) | Mean Load to Failure (N) |
| --- | --- | --- | --- | --- | --- | --- |
| design01 | Double "I" layout e.g. FIG. 12A | 194.8 | 77.9 | 137.0 | 30.4 | 506 |
| design02 | Inverted "U" layout | 190.7 | 76.3 | 147.2 | 32.7 | 520 |
| design03 | Inverted big "U" layout | 166.8 | 66.7 | 187.5 | 41.7 | 528 |
| design04 | "A" shaped layout | 149.6 | 59.8 | 217.0 | 48.2 | 560 |
| design05 | Double "A" layout e.g. FIG. 17A | 129.5 | 51.8 | 251.9 | 56.0 | 565 |

[1]The original area of the compression surface of the uncut block is 10 mm × 25 mm = 250 mm$^2$.

Separately, Table 2 compares the mean load to failure of the various layouts as a function of the volume (mm$^3$) of bone block removed by creation of the channels. In generating the data for Table 2, each of designs 01-05 was cut into the same size (10 mm×5 mm×25 mm) cortical bone block. The omega channels were cut with a 2.4 mm diameter ball end cutter, to a depth of 1.8 mm. The values for % Volume Removed were calculated based on the percentage of the machinable volume cut away, in this case defined by the maximum machinable depth of 1.8 mm. The opposing (cortical) bone blocks that were opposite each of designs 01-05 were substantially identical (to within manufacturing tolerances) and were the same length (25 mm), width (10 mm) and thickness (5 mm) as the bone blocks of designs 01-05. Each of the opposing bone blocks had the identical tendon engaging surface which was sawtooth. Substantially identical segments of allograft tendon were cut and sized prior to sandwiching between a design block (01-05) and an opposing bone block. For each of designs 01-05, bone block-tendon assemblies were made in triplicate and then tested. Testing was accomplished on an Instron Model 5800 force testing machine, Canton, Mass. by measuring the load to failure (N) for each bone block-tendon assembly. Failure occurred when the tendon was pulled free from the bone block assembly. The mean load to failure from the triplicate measurements was then calculated and reported in Table 2.

The various embodiments of the of the intermediate bone blocks, the bone block assemblies and the assembled BTBs of the present invention can be better understood by reference to the Figures.

FIG. 1 is a view of a first comparative bone block-tendon assembly 10 comprising two bone blocks (1 and 2) that sandwich a tendon 3, each bone block having a completely smooth (flat) tendon engaging surface. This first comparative bone block-tendon assembly 10 is tested for average load to failure (Newtons) in Table 1 relative to bone block-tendon assemblies of FIGS. 2-5, each having at least one different tendon engaging surface. When this bone block-tendon assembly 10 was made and comparatively tested for load strength relative to other substantially identical bone tendon assemblies that differed solely in their tendon engaging surfaces, this bone block-tendon assembly fared the worst and only had a mean load to failure of 260 N. See Table 1.

FIGS. 2A-2B provide views of a second comparative bone block-tendon assembly 20 comprising two bone blocks (1 and 4) that sandwich a tendon 3, the first bone block 1 having a smooth tendon engaging surface while the second bone block 4 has a saw tooth pattern or ridges on its tendon engaging surface. FIG. 2A is an exploded view of the second comparative bone block assembly. FIG. 2B is a detailed view of the tendon and bone blocks from FIG. 2A. When this bone block-tendon assembly 20 was made and comparatively tested for average load to failure relative to other substantially identical bone tendon assemblies that differed solely in their tendon engaging surfaces, this bone block-tendon assembly fared better that the flat:flat tendon engaging surface. In particular, this bone block-tendon assembly 20 had an average load to failure of 344N. See Table 1. Thus, substituting a bone block 4 having a saw tooth pattern of ridges as a textured surface for bone block 2 having a flat (smooth) surface increased the load required to induce failure of the resulting bone block tendon assembly 20 by 84 N (or by 32%) under these standardized conditions.

FIG. 3 is a drawing of a third comparative bone block-tendon assembly comprising two bone blocks that sandwich a tendon, each bone block having a textured (saw-tooth pattern) pattern of ridges on its tendon engaging surface. This third comparative bone block-tendon assembly was made and tested for average load to failure (Newtons) in Table 1 relative to bone block-tendon assemblies of FIGS. 1, 2A-2B, 4A-4B, and 5A-5B, each having at least one different tendon engaging surface. Since substituting one of the flat tendon engaging surfaces of FIG. 1 with a textured (saw tooth pattern of ridges) tendon engaging surface as in FIG. 2 produced a 32% improvement in load until failure, one would have thought that substituting the remaining bone block with the flat tissue engaging surface of FIG. 2A with another bone block with a textured (saw tooth pattern of ridges) would have resulted in a bone block-tendon assembly with an increased load at failure relative to the assembly of FIG. 2A. However, the resulting bone block-tendon assembly of FIG. 3A had an average load to failure of 343 N, and thus produced no improvement over the bone block-tendon assembly of FIG. 2A under these standardized conditions.

FIGS. 4A-4D are views of a fourth comparative bone block-tendon assembly 40 comprising two bone blocks that sandwich a tendon 3, the first bone block 4 having a textured pattern (saw-tooth pattern of ridges) on its tendon engaging surface (as for FIG. 3) while the second bone block 5 is an intermediate bone block of the present invention having an a smooth tendon engaging (compression) surface that is interrupted by two channels with rectangular cross-sections 6 running across the direction of pull of the tendon 3. FIG. 4A is an exploded view of the fourth comparative bone block assembly. FIG. 4B is a side view of the assembled fourth comparative bone block assembly. FIG. 4C is an end view FIG. 4D is a detailed view of the tendon and bone blocks from FIG. 4A showing the lengthwise channels having a rectangular cross-section in the intermediate bone block of the present invention. This fourth comparative bone block-tendon assembly was made and tested for average failure load (Newtons) in Table 1 relative to bone block-tendon assemblies of FIGS. 1, 2A-2B, 3A-3B and 5A-5D, each having at least one different tendon engaging surface. Surprisingly, the resulting bone block-tendon assembly 40 of FIGS. 4A-4D had an average load to failure of 426 N, and thus produced an 83 N (24%) improvement over the bone block-tendon assembly of FIG. 3A and a 166 N (64%) improvement over the bone block tendon assembly 10 of FIG. 1 under these standardized conditions.

FIGS. 5A-5D are views of a fifth comparative bone block-tendon assembly 50 comprising two bone blocks (4 and 7) that sandwich a tendon 3, the first bone block 4 having a textured pattern (saw-tooth pattern of ridges) on its tendon engaging surface while the second bone block 7 is a preferred intermediate bone block of the present invention having an a smooth tendon engaging (compression) surface that is interrupted by two channels 8 with omega cross-sections running in the direction of pull of the tendon 3. FIG. 5A is an exploded view of the fifth comparative bone block assembly. FIG. 5B is a side view of the assembled fifth comparative bone block assembly. FIG. 5C is an end view. FIG. 5D is a detailed view of the tendon and bone blocks from FIG. 5A showing the lengthwise channels having a rectangular cross-section in the intermediate bone block of the present invention. This fifth comparative bone block-tendon assembly 50 was made and tested for average load to failure (Newtons) in Table 1 relative to bone block-tendon assemblies of FIGS. 1, 2A-2B, 3A-3B, and 4A-4D, each having at least one different tendon engaging surface. Surprisingly, just changing the shape of the two channels in the bone block-tendon assembly of FIGS. 4A-4D from having a rectangular to an omega cross section to produce the bone block tissue assembly of FIGS. 5A-5D, resulted in a bone-block tendon assembly that would not fail until an average load of 516 N. This change in channel cross sectional shape resulted in an additional 90 N of load to failure or an increase in load to failure of 21% relative the bone block tendon assembly of FIGS. 4A-4D. Viewed from another perspective, merely swapping the intermediate bone block of the present invention (with the omega cross section) for one of the textured bone blocks of FIGS. 3A-3B resulted in a gain in load to failure of 173 N (a 50% increase) over the assembly of FIGS. 3A-3B under these standardized test conditions.

Thus, the intermediate bone blocks of the present invention, which are characterized by the interruption of the soft tissue (e.g., tendon) engaging surface of a bone block with 1-10 surface cavities, particularly channels, and particularly the channels with the undercut or omega cross section, provide enhanced gripping of a soft tissue (particularly a tendon) without tearing or cutting, in a bone block-tendon assembly, such as used in Applicants' assembled BTB.

FIGS. 6A-6D show various views of the textured bone block 60 used in the assemblies of FIGS. 2-5, wherein the texture was a saw-tooth pattern on the tissue (e.g., tendon) engaging surface. FIG. 6A is a perspective view of the textured bone block 60, having opposing end walls 64 and 65, side wall 63, and showing rows of ridges 62 in a saw tooth pattern angled away from the direction of pull of the tendon (arrow). FIG. 6B is a top view of the textured bone block looking directly down at the saw-tooth pattern of ridges on the (soft) tissue engaging surface 61. FIG. 6C is a side view of the textured bone block showing the pattern of ridges 62 which look like angled teeth from this perspective. FIG. 6D is a blow-up of the details of the angled ridges shown in 6D, having a height A and an attack angle B.

FIGS. 7A-7D show various views of an alternative textured bone block 70, wherein the texture is a pattern of ridges and valleys on the tendon engaging surface. FIG. 7A is a perspective view of the textured bone block 70, having opposing end walls 74 and 75, side wall 73 and a textured soft tissue engaging surface 71. FIG. 7B is a top view of the textured bone block 70 looking directly down at the textured pattern on soft tissue engaging surface 71. FIG. 7C is a side view of the textured bone block showing the pattern of mounds 76 and valleys 77 on the soft tissue (e.g., tendon) engaging surface 71. FIG. 7D is an end view of the textured bone block of FIG. 7A showing a different perspective of the mounds and valleys. As shown, the pattern of mounds and valleys is symmetrical. However, it is also within the scope of the present invention that the mounds be angled to preferentially engage the soft tissue in one direction as shown in FIG. 6A.

FIGS. 8A-8D show a series of views of one embodiment of an intermediate bone block of the present invention having channels 87 with a square cross section running substantially perpendicular to the length of the bone block 80 and the intended direction of pull (arrow) of a segment of soft tissue (e.g., tendon). Even if one direction if pull is indicated, it is within the scope of the present invention that the intermediate bone blocks be used in a bone block assembly in either lengthwise orientation (shown as a double headed arrow). FIG. 8A is a perspective view of the intermediate bone block 80, having opposing end walls 84 and 85, side wall 83, and soft tissue engaging surface 81. The soft tissue engaging surface 81 is broken up by a series of channels 87 having a square cross section, leaving a plurality of isolated tissue compression surfaces 86. FIG. 8B is a top view of the intermediate bone block looking directly down at the layout (pattern) of channels 87 in tissue engaging surface 81. FIG. 8C is a side view of the intermediate bone block showing the pattern of cavities (e.g., channels 87) with a square cross section and a plurality of tissue compression surfaces 86 bordering the channels 87. When the width A and the depth B of the channels are equal, the cross section of the channels is a square. However, it is also within the scope of the present invention that A and B are not equal, such that the cross section of the channel 87 is a rectangle. FIG. 8D is a view of the intermediate bone block 80 of FIG. 8A viewed from end 84.

The size range in the intermediate bone blocks of the present invention are based upon the intended use of the bone block and in some instances the size of the patient. Typical sizes of the intermediate bone block range in length from 10 mm to 50 mm; in width from 2 mm to 15 mm; and in height or diameter from 2 mm to 15 mm. Preferably, the length ranges from from 15 mm to 35 mm; more preferably from 20 mm to 25 mm. Preferably, the width ranges from from 6 mm to 13 mm; more preferably from 9 mm to 12 mm. Preferably, the height or diameter ranges from 6 mm to 13 mm; more preferably from 9 mm to 12 mm.

FIGS. 9A-9D show views of another embodiment of an intermediate bone block of the present invention having a plurality of channels 97 running substantially perpendicular to the length of the bone block 90 and the intended direction of pull (arrow) of a segment of soft tissue (e.g., tendon). The plurality of channels 97 are similar to the channels 87 in FIGS. 8A-8D except that the bottom edges of the channels 97 have a radius (R) edge. FIG. 9A is a perspective view of the intermediate bone block 90, having opposing end walls 94 and 95, side wall 93, and soft tissue engaging surface 91. The soft tissue engaging surface 91 is broken up by a series of channels 97 having a rounded square cross section, leaving a plurality of isolated tissue compression surfaces 96. FIG. 9B is a top view of the intermediate bone block 90 looking directly on soft tissue engaging surface 91, which is characterized by a plurality of channels 97 interrupting the surface and leaving a plurality of isolated soft tissue compression surfaces 96. FIG. 9C is a side view of the intermediate bone block showing the pattern of cavities (e.g., channels 97) and tissue compression surfaces 96. The cross section of the channels 97 is shown as square with rounded edges (i.e., a rounded square). In this embodiment as shown, the depth B of the channel 97 equals its width A. However, it is also within the scope of the present invention that A and B are not equal, such that the cross section of the channel 97 is a rectangle. FIG. 9D is a view of the intermediate bone block 90 of FIG. 9A viewed from end 94.

FIGS. 10A-10D show a series of views of another embodiment of an intermediate bone block of the present invention having a plurality of channels 107 running substantially perpendicular to the length of the bone block 100 and the intended direction of pull (arrow) of a segment of soft tissue (e.g., tendon). The plurality of channels 107 have a triangular cross section. FIG. 10A is a perspective view of the intermediate bone block 100, having opposing end walls 104 and 105, side wall 103, and soft tissue engaging surface 101. The soft tissue engaging surface 101 is broken up by a series of channels 107 having a triangular ("V" shaped) cross section, leaving a plurality of isolated tissue compression surfaces 106. FIG. 10B is a top view of the intermediate bone block 100 looking directly on soft tissue engaging surface 101, which is characterized by a plurality of channels 107 interrupting the surface and leaving a plurality of isolated soft tissue compression surfaces 106. FIG. 10C is a side view of the intermediate bone block showing the pattern of cavities (e.g., channels 107) and tissue compression surfaces 106. The cross section of the channels 107 is shown as triangular. In this embodiment as shown, the channel has a depth B and an angle A at its tip. While the triangular channel is shown as equilateral, it is also within the scope of the present invention that the side walls of the triangle not be equal. FIG. 10D is a view of the intermediate bone block 100 of FIG. 10A viewed from end 104.

FIGS. 11A-11D show a series of views of one preferred embodiment of an intermediate bone block of the present invention as used in the test block of FIG. 5 and Table 1. FIG. 11A is a perspective view of one embodiment on an intermediate bone block 110 having opposing end walls 114 and 115, side wall 113, and two channels 117 with an (inverted) omega-shaped cross section running the length of the bone block and substantially in the intended direction of pull (arrow) of a segment of soft tissue (e.g., tendon). The two channels 116 are surrounded by soft tissue compression surfaces 116. FIG. 11B is a top view of the intermediate bone block looking directly down on soft tissue engaging surface 111, having two channels 117 surrounded by soft tissue compression surfaces 116. FIG. 11C is a side view of the intermediate bone block 110, showing that the channels have a substantially uniform depth. However, it is also within the scope of the present invention that the channels 117 have a slope (as also shown elsewhere) between opposing ends 114 and 115, or have incremental changes in depth. FIG. 11D is an end view of the intermediate bone block 110 viewed from end 114, showing the cross sectional (omega) shape of the channels 117. If the block of FIG. 11D is rotated 180° in the plane of the paper, the omega ("Ω") shape of channel 117 becomes more apparent.

FIGS. 12A-12D show a series of views of one preferred embodiment of an intermediate bone block of the present invention. FIG. 12A is a perspective view of one embodiment on an intermediate bone block 120 having opposing end walls 124 and 125, side wall 123, and two channels 127 with an omega-shaped cross section running the length of the bone block and substantially in the intended direction of pull (arrow) of a segment of soft tissue (e.g., tendon). The two channels 126 are surrounded by soft tissue compression surfaces 126. End 124, which is the end from which the soft tissue (e.g., tendon) would extend and be pulled has a radius curve 128 to minimize any sharp edge that could cut into the tendon or fray its edges. This results in an internal leading edge configuration that reduces tissue stresses during assembly and use. FIG. 12B is a top view of the intermediate bone block looking directly down on soft tissue engaging surface 121, having two channels 127 surrounded by soft tissue compression surfaces 126. FIG. 12C is a side view of the intermediate bone block 120, showing that the channels have a substantially uniform depth. However, it is also within the scope of the present invention that the channels 127 have a slope (as also shown elsewhere) between opposing ends 124 and 125, or have incremental changes in depth. FIG. 12D is an end view of the intermediate bone block 120 viewed from end 124, showing the cross sectional (omega) shape of the channels 127. If the block of FIG. 12D is rotated 180° in the plane of the paper, the omega ("Ω") shape of channel 127 becomes more apparent.

FIGS. 13A-13D show a series of views of one embodiment of an intermediate bone block of the present invention having channels 137 with an omega shaped cross section running substantially perpendicular to the length of the bone block 130 and the intended direction of pull (arrow) of a segment of soft tissue (e.g., tendon). FIG. 13A is a perspective view of the intermediate bone block 130, having opposing end walls 134 and 135, side wall 133, and soft tissue engaging surface 131. The soft tissue engaging surface 131 is broken up by a series of channels 137 having an omega shaped square cross section, leaving a plurality of isolated tissue compression surfaces 136. FIG. 13B is a top view of the intermediate bone block looking directly down at the layout (pattern) of channels 137 cut into tissue engaging surface 131, leaving four soft tissue compression surfaces separated by the channels. FIG. 13C is a side view of the intermediate bone block showing the omega cross-sectional shape of the channels. More particularly, when the block of FIG. 13C is rotated 180° in the plane of the paper, the omega ("Ω") shape of channel 137 becomes more apparent. FIG. 13D is a view of the intermediate bone block 130 of FIG. 13A viewed from end 134.

FIGS. 14A-14D show various views of yet another embodiment of an intermediate bone block of the present invention having a plurality of channels with different sized omega-shaped cross sections running substantially perpendicular to the length of the bone block 140 and the intended direction of pull (arrow) of a segment of soft tissue (e.g., tendon). As reflected in the double sided arrow, this bone block which has an asymmetrical layout of channels may have the segment of soft tissue pull in either direction. FIG. 14A is a perspective view of this embodiment on an intermediate bone block, having opposing ends 144 and 145, side 143, tissue engaging surface 141 that is broken up by three different sized channels (147A, 147B and 147C) with omega shaped cross sections, leaving four soft tissue compression surfaces. FIG. 14B is a top view of the intermediate bone block looking directly down at the pattern of channels. FIG. 14C is a side view of the intermediate bone block, showing the pattern of cavities (e.g., channels) and tissue compression surfaces. If the block of FIG. 14C is rotated 180° in the plane of the paper, the omega shape of each of different sized channels 147A, 147B and 147C become apparent. FIG. 14D is an end view of the intermediate bone block of FIG. 14A as viewed from end 144.

FIGS. 15A-15D show various views of yet another embodiment of an intermediate bone block of the present invention. FIG. 15A is a perspective view of one embodiment on an intermediate bone block 150, having opposing ends 154 and 155, sidewall 153 running the length of the bone block 150, soft tissue engaging surface 151 that is broken up by a layout of channels 157B with an (inverted) omega-shaped cross section running substantially perpendicular to the length of the bone block 150 across the intended direction of pull (arrow) of a segment of soft tissue (e.g., tendon) and more channels 157A with an (inverted) omega-shaped cross section running substantially in the intended direction of pull (arrow) of a segment of soft tissue (e.g., tendon). The layout of channels cut into tissue engaging surface 151 leave behind a plurality of soft tissue (e.g., tendon) compression surfaces 156. FIG. 15B is a top view of the intermediate bone block looking directly down at tissue engaging surface 151 having criss-crossing channels 157A and 157B producing a waffle pattern of plateaus of tissue compression surfaces 156. FIG. 15C is a side view of the intermediate bone block showing the pattern of cavities (e.g., channels) 157B with the omega shaped cross section. FIG. 15D is an end view of the intermediate bone block of FIG. 15A also showing a lengthwise view of channels 157A having the omega shaped cross-section. If the views of FIGS. 15C and 15D are rotated 180° in the plane of the paper, the omega cross-sectional shape of channels 157B and 157A, respectively becomes more apparent.

FIGS. 16A-16D show various views of yet another embodiment of an intermediate bone block of the present invention having a plurality of channels with omega-shaped cross sections running generally widthwise and across the intended direction of pull (arrow) of a segment of soft tissue (e.g., tendon). FIG. 16A is a perspective view of intermediate bone block 160, having opposing ends 164 and 165, sidewall 163 running the length of the bone block 160, soft tissue engaging surface 161 that is broken up by a "V" shaped layout of channels 167 with an (inverted) omega-shaped cross section running substantially across the intended direction of pull (arrow) of a segment of soft tissue (e.g., tendon). The layout of channels 167 cut into tissue engaging surface 161 leave behind a plurality of soft tissue (e.g., tendon) compression surfaces 166. The asymmetry of the layout of the channels does not limit the bone block to be limited to one particular direction of use. As shown in the double headed arrow, the bone block 160 can be used in either lengthwise direction relative to the direction of pull of the soft tissue. FIG. 16B is a top view of the intermediate bone block looking directly down at tissue engaging surface 161 having a "V" shaped layout of four channels 167 cut therein, leaving a plurality of tissue compression surfaces 166. FIG. 16C is a side view of the intermediate bone block showing the (inverted) omega cross sectional shape of the channels 167. If the block of FIG. 16C is rotated 180° in the plane of the paper, the omega ("Ω") shape of the channels 167 becomes more apparent. FIG. 16D is an end view of the intermediate bone block 160 of FIG. 16A viewed from end 164.

FIGS. 17A-17D show a series of views of a more preferred embodiment of an intermediate bone block of the present invention. FIG. 17A is a perspective view of intermediate bone block 170, having opposing ends 174 and 175, sidewall 173 running the length of the bone block 170, soft tissue engaging surface 171 that is broken up by a stacked/overlapping double "A" (or stacked or overlapping triple "U") pattern of channels 177 (as tested in Table 2). In this embodiment, the layout of the channels has a first component that runs lengthwise parallel wall 173 and in the intended direction of pull (arrow) of a segment of soft tissue (e.g., tendon), and a second component that runs widthwise and/or across the intended direction of pull of the tendon. The layout of channels 177 that are cut into tissue engaging surface 171 leave behind a plurality of soft tissue (e.g., tendon) compression surfaces 177. While the embodiment of FIG. 17A shows the triple "U" pattern, it is also within the scope of the present invention that the channel layout be a single "U" pattern (as in designs 2 and 3 of Table 2) or a double "U" pattern. FIG. 17B is a top view of the intermediate bone block looking directly down at the triple "U" shaped layout of the channels. FIG. 17C is a side view of the intermediate bone block showing the pattern of cavities (e.g., channels) and tissue compression surfaces. If the block of FIG. 17C is rotated 180° in the plane of the paper, the omega ("Ω") shape of the channels 177 becomes apparent. FIG. 17D is an end view of the intermediate bone block of FIG. 17A.

FIGS. 18A-18D show a series of views of another embodiment of an intermediate bone block of the present invention. This embodiment is essentially the intermediate bone block of FIGS. 11A-11B that is modified to have as its tendon engaging surface the textured surface of FIGS. 6A-6C. Other textured surfaces can be utilized in the same manner as the tendon engaging surface, e.g., that shown in FIGS. 7A-7D. FIG. 18A is a perspective view of intermediate bone block 180, having opposing ends 184 and 185, sidewall 183 running the length of the bone block 180, soft tissue engaging surface 181 having rows of ridges 189 angled to engage the soft issue in the direction of pull of the tendon, the soft tissue engaging surface being broken up by two channels 187 cut therein, the channels running the length of the bone block 180 and having an (inverted) omega-shaped cross section. FIG. 18B is a top view of the intermediate bone block 180 looking directly down at tissue engaging surface 181 and the two substantially parallel channels 187 cut therein, leaving three textured soft tissue compression surfaces 186. FIG. 18C is a side view of the intermediate bone block showing the saw tooth pattern of angled ridges 189 appearing as angled teeth in this perspective. FIG. 18D is an end view of the intermediate bone block of FIG. 18A viewed from end 184, showing the omega shaped cross section of channels 187. If the block of FIG. 18D is rotated 180° in the plane of the paper, the omega ("Ω") shape of each of channels 187 becomes more apparent.

FIGS. 19A-19D show a series of views of the external profile of one embodiment of an intermediate bone block of the present invention. FIGS. 19A-19D are essentially views of the flip side of the intermediate bone block of FIG. 11A-11D, respectively, wherein all outside edges were rounded to have a radius. FIG. 19A is a perspective view of intermediate bone block 190, having opposing ends 194 and 195 each with a radius edge 199 of radius R1, sidewall 193 extending the length of the bone block 190 and having radius edge 198 of radius R2. The radius R1 typically ranges from 0.5 mm to 5 mm. The radius R2 typically ranges from 0.5 mm to 5 mm. FIG. 19B is a top view of the intermediate bone block 190 of FIG. 19A, showing an exterior surface 196 opposite the tissue engaging surface 191 (not shown) and radius edges 198 and 199. FIG. 19C is a side view of the bone block 190 of FIG. 19A showing the outside corners having a rounded edge of radius R1, and showing as a broken line the internal omega shaped channel running the length of the bone block. FIG. 19D is an end view of the intermediate bone block of FIG. 19A viewed from its end 194 and looking down the length of the two channels 197 having the omega ("Ω") shaped cross section in upright form in this perspective. Alternative embodiments of shapes for the outer surface of the intermediate bone block or bone block assembly include but are not limited to polygonal, cylindrical, threaded, bulleted, chamfered, angled, ridged, capsule shaped, tapered or a combination thereof.

FIGS. 20A-20D show a series of views of one embodiment for the exterior shape of an intermediate bone block of the present invention. This embodiment essentially superimposes a capsule shape on the intermediate bone block of FIGS. 11A-11D. FIG. 20A is a perspective view of capsule shaped intermediate bone block 200, having soft tissue (e.g. tendon) engaging surface 201 with two channels 207 cut therein and running the length of the capsule, the channels 207 having in this view an (inverted) omega-shaped cross section. Soft tissue engaging surface 201 also has three soft tissue compression surfaces 206 that are interrupted by two holes 202, sized and placed for receiving a pin (not shown) that would engage and penetrate any soft tissue thereon and any opposing bone block face thereon. The length of any of the capsule shaped intermediate bone blocks of the present invention typically range from 10 mm to 50 mm, more typically from 15 mm to 35 mm, preferably from 20 mm to 25 mm. FIG. 20B is a top view of the soft tissue engaging face 201 of the intermediate bone block 200 looking directly down at the pattern of channels 207 and pin holes 202. The undercut nature of the omega channels is seen as the broken lines running parallel channels 207. This view also shows the capsular shape of the bone block which facilitates its introduction into a bone tunnel in a patient to be treated. Each of the ends of the bone block have a first radius R1. The radius R1 ranges from 3 mm to 10 mm. Alternatively, the radius R1 may be defined such that it creates a full round across the entire end of the bone block. Each of the ends of the bone block have a second radius R2. The radius R2 ranges from 3 mm to 10 mm. Alternatively, the radius R2 may be defined such that it creates a full round across the entire end of the bone block assembly when assembled with another bone block having similar external geometry. The body of the cylinder has a radius R3. Typical dimensions of a circular surgical bone tunnel have a diameter of between about 7 mm and 12 mm. Hence, a typical diameter (2×R3) of the semi capsular bone block 200 is from about 7 mm to about 12 mm, respectively or slightly smaller. Different combinations of radius values for R1, R2, and R3 will result in tangent, truncated, or sharp corner edge transitions between the end of the bone block and the body of the bone block, e.g., 7 mm diameter bone block with a 10 mm R1 will produce a sharp edge or corner between the body and the end as seen in FIG. 20B, while a 10 mm diameter bone block with a 5 mm R1 will produce a tangent edge between the end of the bone block and the body of the bone block. FIG. 20C is a side view of the intermediate bone block 200 showing another view of its semi-capsular shape. In this perspective, which is rotated 90° along the long axis of the capsule in FIG. 20B, the radius at each end remains R1 as in FIG. 20B. FIG. 20D is an end view of the intermediate bone block of FIG. 20A. If the block of FIG. 20D is rotated 180° in the plane of the paper, the omega shape ("Ω") of channel 207 becomes more apparent.

FIGS. 21A-21D show various views of the exterior surface of a semi-capsule shaped embodiment of a bone block. The semi-capsular bone block of FIGS. 21A-21D can serve as the opposing bone block to the bone block of FIGS. 20A-20D. FIG. 21A is a perspective view of semi capsular bone block 210 showing holes 212 for receiving a biocompatible pin (not shown) that would hold this bone block to any one of a variety of appropriately shaped intermediate bone blocks (of the present invention) and to a segment of soft tissue sandwiched therebetween. FIG. 21B is a top view of the outside face of this opposing bone block looking directly down at its capsule shape, having ends with radius R1 and holes 212 for receiving an interference pin. The radius R1 typically ranges from 3 mm to 10 mm. Alternatively, the radius R1 may be defined such that it creates a full round across the entire end of the bone block. Each of the ends of the bone block have a second radius R2. The radius R2 ranges from 3 mm to 10 mm. Alternatively, the radius R2 may be defined such that it creates a full round across the entire end of the bone block assembly when assembled with another bone block having similar external geometry. The body of the cylinder has a radius R3. Typical dimensions of a circular surgical bone tunnel have a diameter of between about 7 mm and 12 mm. Hence, a typical diameter (2×R3) of the semi capsular bone block 210 is from about 7 mm to about 12 mm, respectively or slightly smaller. Different combinations of radius values for R1, R2, and R3 will result in tangent, truncated, or sharp corner edge transitions between the end of the bone block and the body of the bone block, e.g., 7 mm diameter bone block with a 10 mm R1 will produce a sharp edge or corner between the body and the end as seen in FIG. 21B, while a 10 mm diameter bone block with a 5 mm R1 will produce a tangent edge between the end of the bone block and the body of the bone block. FIG. 21C is a side view of the opposing bone block 210 showing its semi-capsular shape. In this perspective, which is rotated 90° along the long axis of the capsule in FIG. 21B, the radius at each end remains R1 as in FIG. 21B. FIG. 21D is an end view of the opposing bone block of FIG. 21A. When the bone block of FIG. 21A has channels (not shown) on its tissue engaging surface 211, it becomes an intermediate bone block of the present invention. In the present embodiment, the opposing bone block 210 is shown with a flat tissue engaging surface 211. However, it is also within the scope of the present invention that the opposing bone block (to any of Applicants' intermediate bone blocks) also have a textured surface, two of which are exemplified in FIGS. 6A-6C and 7A-7D.

FIGS. 22A-22D show a series of views of an embodiment of the exterior profile of an intermediate bone block of the present invention. FIG. 22A is a perspective view of the exterior surface of intermediate bone block 220, which is analogous to the intermediate bone block of FIGS. 20A-20D, except that intermediate bone block 220 has a longitudinal groove 229 running its length. Groove 229 has radius R, which is suitable for maximizing radial contact with an interference screw (not shown). Groove 229 also has two holes 222 positioned thereon and suitably sized for receiving an interference pin (not shown) which would hold intermediate bone block 220 to a suitably sized opposing bone block (e.g., 200 or 210) and a segment of soft tissue sandwiched therebetween. Intermediate bone block 220 also has a pair of channels 22 with an omega shaped cross section running the length of its tissue engaging surface 221. FIG. 22B is a top view of intermediate bone block 220 looking directly down at its capsular shape from this perspective, having opposing ends with a radius R1, centrally positioned groove 229, and the two symmetrically placed pin holes 222 in the groove 229. In an alternate embodiment, the groove is positioned off center. The radius R1 typically ranges from 3 mm to 10 mm. Alternatively, the radius R1 may be defined such that it creates a full round across the entire end of the bone block. Each of the ends of the bone block have a second radius R2. The radius R2 ranges from 3 mm to 10 mm. Alternatively, the radius R2 may be defined such that it creates a full round across the entire end of the bone block assembly when assembled with another bone block having similar external geometry. The body of the cylinder has a radius R3. Typical dimensions of a circular surgical bone tunnel have a diameter of between about 7 mm and 12 mm. Hence, a typical diameter (2×R3) of the semi capsular bone block 220 is from about 7 mm to about 12 mm, respectively or slightly smaller. Different combinations of radius values for R1, R2, and R3 will result in tangent, truncated, or sharp corner edge transitions between the end of the bone block and the body of the bone block, e.g., 7 mm diameter bone block with a 10 mm R1 will produce a sharp edge or corner between the body and the end as seen in FIG. 22B, while a 10 mm diameter bone block with a 5 mm R1 will produce a tangent edge between the end of the bone block and the body of the bone block. FIG. 22C is a side view of the intermediate bone block showing its semi-capsular shape and the positions of the holes 222 running through to tissue engaging surface 221. FIG. 22D is an end view of the intermediate bone block of FIG. 22A, showing the generally hemispherical shape of radius R3 interrupted by groove 229 having a radius R. The radius R typically ranges from 1 mm to 10 mm. Typically, an intermediate bone block has 1 such groove for an interference screw, alternatively an intermediate bone block can have 2 to 6 such grooves, resulting in final bone block assemblies with grooves to accommodate from 1 to 12 interference screws, preferably 1 to 6 interference screws, more preferably 2 to 4 interference screws. Grooves for interference screws have threads, tapped threads or no threads. In an alternate embodiment, grooves for interference screws are specifically not included (e.g., when other fixation methods are used). In another alternate embodiment, a same or similar groove is included in the design to accommodate soft tissue that is external to the bone block assembly. Looking longitudinally down the capsular shape, there is a pair of channels 22 having an omega shaped cross section. In practice, this intermediate bone block may serve as the opposing bone block for the bone blocks of FIGS. 20A-20D or FIGS. 21A-21D.

FIGS. 23A-23D show views of an alternate embodiment for the exterior surface of an intermediate bone block 230 of the present invention. Intermediate bone block 230 is semi-capsule shaped bone block that can be combined with the opposing bone block of FIGS. 20A-20D, 21A-21D, 22A-22D or itself 23A-23D. FIG. 23A is a perspective view of semi-capsule shaped intermediate bone block 230, having rounded opposing ends of radius R1, holes 232 for receiving a biocompatible pin (not shown) that would hold this bone block to any one of a variety of appropriately shaped intermediate bone blocks and to a segment of soft tissue sandwiched therebetween. Also shown on the exterior surface of this embodiment are ridges 239 suitable for gripping a bone tunnel and reducing slippage in the direction of pull (arrow) of the tendon. Alternative embodiments of shapes for the outer surface of the intermediate bone block or bone block assembly include but are not limited to polygonal, cylindrical, threaded, bulleted, chamfered, angled, ridged, capsule shaped, tapered or a combination thereof. FIG. 23B is a top view of the outside face of this intermediate bone block 230 looking directly down at its capsule shape (from this perspective) and the position of the pin holes 232. In this figure, the hemispherical ends have radius R1, and the ridges project at an angle "C". The angle C ranges from 1° to 60°. The radius R1 typically ranges from 3 mm to 10 mm. Alternatively, the radius R1 may be defined such that it creates a full round across the entire end of the bone block. Each of the ends of the bone block have a second radius R2. The radius R2 ranges from 3 mm to 10 mm. Alternatively, the radius R2 may be defined such that it creates a full round across the entire end of the bone block assembly when assembled with another bone block having similar external geometry. The body of the cylinder has a radius R3. Typical dimensions of a circular surgical bone tunnel have a diameter of between about 7 mm and 12 mm. Hence, a typical diameter (2×R3) of the semi capsular bone block 230 is from about 7 mm to about 12 mm, respectively or slightly smaller. Different combinations of radius values for R1, R2, and R3 will result in tangent, truncated, or sharp corner edge transitions between the end of the bone block and the body of the bone block, e.g., 7 mm diameter bone block with a 10 mm R1 will produce a sharp edge or corner between the body and the end as seen in FIG. 23B, while a 10 mm diameter bone block with a 5 mm R1 will produce a tangent edge between the end of the bone block and the body of the bone block. FIG. 23C is a side view of the intermediate bone block 230 showing its semi-capsular shape and channel 237 running its length. FIG. 23D is an end view of the intermediate bone block 230, showing the generally hemispherical shape of radius R1. The radius R1 ranges from 3 mm to 10 mm. Looking longitudinally down the capsular shape, there is a pair of channels 22 having an omega shaped cross section. In practice, this intermediate bone block may be combined with the bone block of FIG. 20A, FIG. 21A, FIG. 22A or preferably FIG. 23A.

Figure 24B:
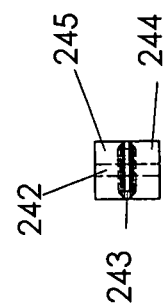
Figure 24C:
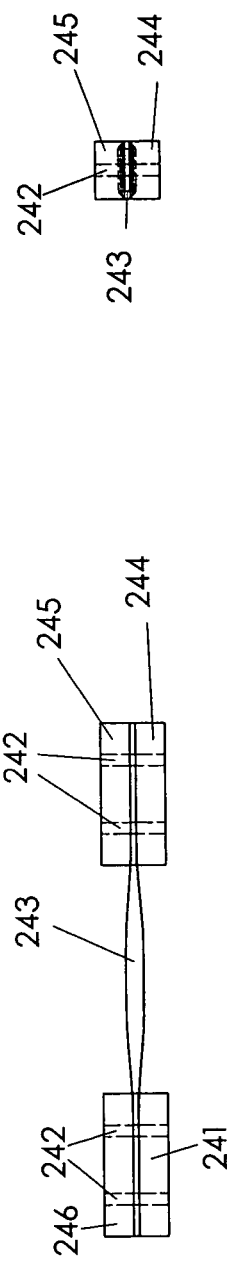
Figure 24D:
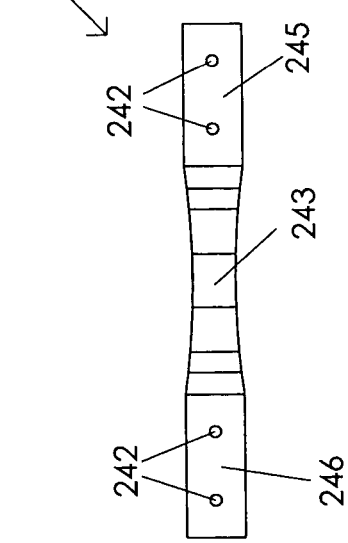

FIGS. 24A-D are views of one embodiment of a BTB of the present invention, defined as a length of soft tissue (e.g., typically tendon or ligament) having opposing ends and a bone block-tendon assembly at each of the opposing ends. FIG. 24A is a perspective view of an assembled BTB 240 of the present invention. In this perspective view, the BTB 240 is composed of a predetermined length of soft tissue 243 having opposing ends with bone blocks 244 and 245 sandwiching the soft tissue 243 at a first opposing end and bone blocks 241 and 246 sandwiching the soft tissue 243 at its second opposing end. The bone blocks 241, 244, 245 and 246 may be the same or different. At least one of the bone blocks at each opposing end is an intermediate bone block of the present invention. Preferably, one of the bone blocks at each end has 1-10 channels on the soft tissue engaging surface, wherein the channel(s) has an omega shaped cross section. The soft tissue 243 can be any of the soft tissues described herein. Pins 242 are inserted in holes in the opposing bone blocks and provide an interference fit, holding the bone blocks in juxtaposition and sandwiching the soft tissue therebetween to form a unitary device. The pins can be any of the pins described herein. Preferably, they are cortical bone pins. FIG. 24B is a top view of the assembled BTB 240, wherein one embodiment for positioning two bone pins is shown. It is within the scope of the present invention to have up to 30 pins. Typically, 1-5 pins are used per bone block assembly. More typically, 2-3 pins are used per bone block assembly. FIG. 24C is a side view of the assembled BTB clearly showing the soft tissue 243 sandwiched between opposing bone blocks at each end. FIG. 24D is an end view of the assembled BTB 240 clearly showing the soft tissue 243 sandwiched between opposing bone blocks 244 and 245 with pin 242 shown as internally transversing opposing bone blocks 244 and 245, and soft tissue 243 sandwiched therebetween.

FIGS. 25A-25D are views of another embodiment of a BTB of the present invention. FIG. 25A is an exploded perspective view of a preferred embodiment of an assembled BTB 250 of the present invention. In this exploded perspective view, the BTB 250 is composed of two assembled bone block assemblies, one on each of the opposing ends of a segment of soft tissue 253 of predetermined length. Typical lengths for the soft tissue depends upon the application and the size of the patient. In the case of a BTB intended for anterior cruciate ligament repair in a human patient, the length of the soft tissue between the bone blocks ranges from about 32 mm to about 58 mm, preferably from about 38 mm to about 52 mm, and more preferably from about 42 mm to about 48 mm. In FIG. 25A, each bone block-tendon assembly has at least one intermediate bone block 251 of the present invention as a component thereof. Each of intermediate bone blocks 251 are shown as having soft tissue engaging face 251A with a stacked/overlapping triple "U" pattern of channels 257 thereon, each channel having the omega-shaped cross section. Intermediate bone blocks 251 also have holes 252 for receiving interference pins 257. Bone blocks 256 have a groove 258 of a predetermined radius (see the discussion of FIG. 22) for accommodating the curvature of an interference screw. FIG. 25B is a top view of the assembled BTB wherein one embodiment for positioning three bone pins 257 is shown. Additional holes 259 can be used to accommodate additional pins, or may be used for two pin placement instead of the currently shown three pin placement, or to accept suture during surgery for purposes of holding, guiding, or pulling graft into place in the bone tunnel and for tensioning the graft prior to and during fixation. Additional relief or guidance features such as slots, ridges, or small grooves (not shown) allow the suture to be routed away from the interference screw and thus protected from damage or cutting of the suture as the interference screw advances, thus ensuring the ability to hold tension on the graft during fixation. Depressions 255 are useful as physical and visual placement aids during surgery, as they provide a visual marker for the surgeon to align fixations devices such as an interference screw, and they also provide a physical reference point and positive location and contact for instruments or guide wires to push or guide the graft into place. FIG. 25C is a side view of the assembled BTB 250 wherein the bone blocks 256 are shown as having a soft tissue engaging face 256A with teeth (actually row of ridges) angled against the direction of pull of the tendon (arrows) and engaging the soft tissue 253. FIG. 25D is an end view of the assembled BTB clearly showing the soft tissue 253 sandwiched between opposing semi-capsular bone blocks 251 and 256, having a cross sectional radius R1. In this view, the assembled BTB has the generally circular diameter of a bone tunnel into which it can be inserted during a surgical repair of a tendon in a patient in need of such a repair. In this view, the groove 258 is visible and would accommodate an interference screw (not shown) for locking that end of the BTB in its corresponding bone tunnel. In an alternate embodiment, grooves for interference screws are specifically not included (e.g., when other fixation methods are used).

FIGS. 26A-26D are views of another embodiment of a BTB of the present invention. FIG. 26A is a perspective view of assembled BTB 260 of the present invention. In this perspective view, a length of the soft tissue 263 having two opposing ends is wrapped around three sides of bone block 265 at its first opposing end and around three sides of bone block 267 at its second opposing end, to produce a three layer soft tissue:bone:soft tissue sandwich. The segment 263A of the soft tissue 263 engages the soft tissue engaging face of bone block 264 to produce the fourth layer of the sandwich. The segment 263B of the soft tissue 263 engages the soft tissue engaging face of bone block 266 to produce the fourth layer of the sandwich. In the BTB of 260, at least one of the two bone blocks at each end of tendon 263 is an intermediate bone block of the present invention. Preferably, the soft tissue engaging face of the intermediate bone block of the present invention engages soft tissue segment 263A at the first opposing end and soft tissue segment 263B at its second opposing end. FIG. 26B is a top view of the assembled BTB wherein only the soft tissue 263 is visible. FIG. 26C is cross-sectional side view CC of the assembled BTB clearly showing the soft tissue 263A and 263B sandwiched between opposing bone blocks at each end and the presence of the biocompatible pins 262 holding the opposing bone blocks as an assembled unitary piece. FIG. 26D is a side view of the assembled BTB 260 clearly showing the soft tissue 263A sandwiched between bone blocks 264 and 265 at the first opposing end and soft tissue 263B sandwiched between bone blocks 267 and 266 at the second opposing end. In an alternate embodiment, a groove (not shown) is included in the design to accommodate the soft tissue that is external to the bone block assembly.

FIGS. 27A-27D are views of another embodiment of a BTB of the present invention. FIG. 27A is a perspective view of BTB 270 of the present invention, which is essentially BTB 260 of FIG. 26A further comprising a third bone block at each end sandwiching the exterior layer of soft tissue above the bone block to produce a five layer assembled sandwich. In particular, FIG. 27A is a perspective view of assembled BTB 270, having a length of the soft tissue 273 having two opposing ends. The soft tissue of this BTB or any BTB described herein is selected from any of the soft tissue described herein. Preferably, the soft tissue is a tendon or a ligament or a bundle of 2-10 tendons or 2-20 ligaments, or a mixture thereof, any of which are of the same or different lengths, and/or are braided, side-by-side or overlapping. The first opposing end of the soft tissue 273 engages bone block 275 and wraps around three faces of bone block 275 to produce a soft tissue (273A):bone block (275): soft tissue (273) sandwich. The first soft tissue portion 273A of this sandwich is covered with the soft tissue engaging face of bone block 274 and the second soft tissue portion 273 of the sandwich is covered with the tissue engaging face of bone block 279, resulting in a 5 layer bone:soft tissue:bone:soft tissue:bone sandwich. This 5 membered sandwich is held together by biocompatible connectors 272, as described herein, preferably interference pins, more preferably pin of cortical bone that provide an interference fit. Preferred pins are cortical bone pins. The second opposing end of the soft tissue 273 engages bone block 277 and wraps around three faces of bone block 277 to produce a soft tissue (273B):bone block (277): soft tissue (273) sandwich. The first soft tissue portion 273B of this sandwich is covered with the soft tissue engaging face of bone block 276 and the second soft tissue portion 273 of the sandwich is covered with the tissue engaging face of bone block 278, resulting in a 5 layer bone:soft tissue:bone:soft tissue:bone sandwich. This 5 membered sandwich is held together by biocompatible connectors 272, as described herein, preferably interference pins, more preferably pin of cortical bone that provide an interference fit. Preferred pins are cortical bone pins. FIG. 27B is a top view of the assembled BTB wherein the assembly appears the same as in FIG. 24B. FIG. 27C is cross-sectional side view CC of the assembled BTB, clearly showing three bone blocks sandwiching two portions of the length of soft tissue (e.g., tendon) as those portions in turn sandwich the central bone block. The assembly is held together at each end by biocompatible connectors 272, preferably interference pins, more preferably cortical bone pins providing an interference fit. FIG. 27D is a side view of the outside face of the assembled BTB clearly showing the soft tissue sandwiched between opposing bone blocks at each end. In each of the 5 layered (bone:soft tissue:bone:soft tissue:bone) sandwiches at each end of the assembled BTB, there are four bone tendon interfaces and three bone blocks. In a BTB of the present invention, at least one of the bone blocks must be a bone block of the present invention. It is also within the scope of the present invention that 2 or all three of the bone blocks of the sandwich are an intermediate bone block of the present invention. However, it is also within the scope of the invention that 1 or 2 of the 3 bone blocks of the sandwich have a textured surface. For example, in one embodiment, the center bone block of the sandwich has teeth that are angled toward the direction of pull of the soft tissue. In this embodiment, it must be kept in mind that the direction of pull of the tendon reverses on opposing sides of the central bone block. In an alternate embodiment, a groove (not shown) is included in the design to accommodate the soft tissue that is external to the bone block assembly.

FIGS. 28A-28D are views of another embodiment of a BTB of the present invention comprising two segments of soft tissue of different lengths (shown) as members of a 5 layer assembly of bone and soft tissue at each end. In this embodiment, the two segments of soft tissue may have the same or different widths, or areas, or they may come from different sources or species. In another embodiment (not shown), the lengths of soft tissue are the same. FIG. 27A is a perspective view of a double tendon (soft tissue) BTB 280 comprising layers of bone:soft tissue:bone:soft tissue:bone. In FIG. 28A, there is a first segment of soft tissue 283B of a predetermined length and a second segment of soft tissue 283A of a longer predetermined length. Typically the difference in length between the two segments of soft tissue in this embodiment ranges from 1 mm to 10 mm depending upon surgical or anatomical requirements influenced by factors such as age, sex, physical size and activity level of the intended patient as well as the nature of injury and any complicating factors such as additional injuries or previous condition of the patients knee. Preferably, the difference in length between the two segments of soft tissue in this embodiment ranges from 1 mm to 8 mm, more preferably from 1 mm to 5 mm, most preferably 1 mm to 3 mm. The length of the first segment of soft tissue 283B determines the length of this BTB because the additional length in the second segment of soft tissue 283A is allowed to bow as shown in FIGS. 28A, 28C and 28D. At the first opposing end (the proximal end in FIG. 28A) of the BTB 280, there is a five membered sandwich comprising in ascending order: bone block 284 having a tissue engaging face, a first end of soft tissue segment 283B, bone block 285 having two tissue engaging faces, a first end of soft tissue segment 283A, and bone block 289 having a tissue engaging face engaging the first end of soft tissue segment 283A. At the second opposing end (the distal end in FIG. 28A) of the BTB 280, there is a five membered sandwich comprising in ascending order: bone block 284 having a tissue engaging face, a first end of soft tissue segment 283B, bone block 285 having two tissue engaging faces, a first end of soft tissue segment 283A, and bone block 289 having a tissue engaging face engaging the first end of soft tissue segment 283A. Each of the five layered sandwiches is held together as a unit by biocompatible connectors 272 as described herein (e.g., screws, pins), preferably interference pins, more preferable cortical bone pins. In FIG. 28B is a top view of the assembled BTB wherein the assembly appears the same as in FIG. 24B. FIG. 28C is a side view of the assembled BTB, clearly showing three bone blocks sandwiching two distinct lengths of soft tissue (e.g., tendon) 283A and 283B, as those lengths of soft tissue sandwich the central bone blocks 285 and 287 at their opposing ends. FIG. 28D is an end view of the BTB of FIG. 28A showing the longer soft tissue segment 283A extending beyond the plane of the bone blocks and the 5 membered sandwich. In each of the 5 layered (bone:soft tissue:bone:soft tissue:bone) sandwiches at each end of the assembled BTB, there are four bone tendon interfaces and three bone blocks. In a BTB of the present embodiment, at least one of the bone blocks must be a bone block of the present invention. It is also within the scope of the present embodiment that 2 or all three of the bone blocks of the sandwich are an intermediate bone block of the present invention. However, it is also within the scope of the present embodiment that 1 or 2 of the 3 bone blocks of the sandwich have a textured surface. For example, in one embodiment, the center bone block of the sandwich has teeth that are angled toward the direction of pull of the soft tissue. Although this embodiment shows the use of two biocompatible connectors 272 in each bone block-tendon assembly (5 layered sandwich), it is within the scope of this invention to employ up to 9 biocompatible connectors, typically 3-5.

FIGS. 29A-29D are views of a dual tendon BTB 290 that is a hybrid of FIGS. 28A and 24A insofar as the bone-tendon assembly at the first opposing end is a three layer sandwich and at the second opposing end is a five layer sandwich. FIG. 29A is a is a perspective view of a double tendon BTB 290 comprising 3 layers of bone:soft tissue:bone at one end and 5 layers of bone:soft tissue:bone:soft tissue:bone at the opposing end. In FIG. 29A, the length of soft tissue 293 has two segments 293A and 293B coming from a single segment 293 between bone blocks 294 and 295. In one embodiment, the single segment of soft tissue is merely sliced down the middle at one end to produce a "Y" shaped tissue having segments 293A and 293B. In another embodiment, separate and distinct soft tissue segments 293A and 293B (typically, tendons or ligaments) are stapled, glued, sutured, woven or braided together to form single segment 293. In this latter embodiment, the soft tissue segments may be the same or different, and they may be of the same or different lengths, widths, areas, sources or species. Typically, the split is stapled, glued, sutured, woven, braided or clamped together or with an additional piece of soft tissue in order to support or control the location of the split in the "Y" geometry. The FIG. 29B is a top view of the assembled BTB wherein the assembly appears substantially the same as in FIG. 24B. The number and placement of the biocompatible connectors 292 in this embodiment (or any other embodiments herein) may vary from one bone block assembly to another. FIG. 29C is a side view of the assembled BTB, clearly showing three bone blocks sandwiching two distinct lengths of soft tissue (e.g., tendon) 293A and 293B at one end and two bone blocks 294 and 295 sandwiching a single length of soft tissue 293 at the opposing end. The assembly is optionally held together at each end by 2-3 biocompatible connectors 292 as described herein (e.g., screws, pins), preferably interference pins, more preferable cortical bone pins. FIG. 29D is an end view of the BTB of FIG. 29A showing the longer soft tissue segment 293A extending above the plane of the bone blocks.

FIGS. 30A-30B are side and end views, respectively, of a harvested BTB 300 having a tendon 303 of a first defined length L1 naturally attached at its first end to a first bone block 301 and naturally attached at its second end to a second bone block 302. FIGS. 30C and 30D are side and end views, respectively, of spacers 306 and 307 for increasing the length of bone (and reducing the exposed length of tendon) in an assembled BTB of FIG. 30E. Spacers 306 and 307 are shown as being the same length. However, it is also within the scope of the present invention that their lengths are different. Bone blocks 309 and 308 are optional and are used to cap the exposed tendon sandwich. These bone blocks may have a smooth tissue engaging surface, a textured tissue engaging surface (such as shown in FIG. 6A or 7A), or be intermediate bone blocks of the present invention. Preferably, they are an intermediate bone block of the present invention. Also, it is within the scope of the invention that the outside edges of the caps be rounded or that in FIG. 30D, that bone block 308 be semi-circular or semi-ovular instead of rectangular (as shown). FIGS. 30E and 30F are side and end views, respectively, of an assembled bone block wherein the length L1 of the tendon in a harvested BTB has been reduced to length L2 by assembling spacers 306 and 307 to opposing naturally attached bone blocks 302 and 301, respectively. The tendons are capped at each end by bone blocks 308 and 309 and the sandwich comprising cap (bone block), tendon and naturally attached bone block, and spacer block are formed into a unitary assembled device by insertion of biocompatible connectors 305 that traverse each component of the assembly. The biocompatible connectors 305 (e.g., screws, pins) are any mechanical connectors that are disclosed herein, preferably interference pins, more preferably cortical bone pins providing an interference fit. In an alternate embodiment, one or both spacers 306 or 307 may be omitted or replaced with a bone block of approximately equal size to the naturally attached bone block. The bone block used in place of the spacer is an intermediate bone block of the present invention or other bone block.

FIGS. 31A-31D are views of an alternate embodiment of an intermediate bone block of the present invention. FIG. 31A is a perspective view of intermediate bone block 310 having a channel of uniform width therein. The channel is defined by a sloped floor 317 (relative to tissue engaging surface 316) and substantially parallel sidewalls 311. However, in other related embodiments that are not shown, it is also within the scope of the present invention that the sidewalls diverge or converge depending upon perspective. FIG. 31B is a top view of the intermediate bone block looking directly down at the central channel with substantially parallel side walls 311 and sloped floor 317. FIG. 31C is a side view of the intermediate bone block showing the slope of the floor 317 in the central channel. FIG. 31D is an end view of the intermediate bone block of FIG. 31A looking up the channel at sloping floor 317. Although the present embodiment can be used with the soft tissue extending from end 314 having the shallow end of the channel or end 315 having the deep end of the channel, it is preferred that the soft tissue extend from end 314 having the shallow end of the channel.

FIGS. 32A-32D are views of an alternate embodiment of an intermediate bone block of the present invention. FIG. 32A is a perspective view of intermediate bone block 320, having a converging channel of substantially uniform depth. The converging channel is defined by floor 327 of substantially uniform depth (relative to the tissue engaging surfaces 326) and sidewalls 321 that converge as the walls extend from end 325 to opposing end 324. FIG. 31B is a top view of the intermediate bone block 320 showing the channel with floor 327 and converging side walls 321. While the side walls are shown at wide divergence at end 325, it is also within the scope of the present invention that the sidewalls 321 be relatively closer together than shown in FIG. 32B at end 325 and that the angle of convergence be from 1° to 12° relative to a center line in the channel. FIG. 31C is a side view of the intermediate bone block showing that the channel with floor 327 is of a substantially uniform depth. FIG. 31D is an end view of the intermediate bone block of FIG. 31A looking down the channel from end 325 at converging sidewalls 321.

Figure 33A:
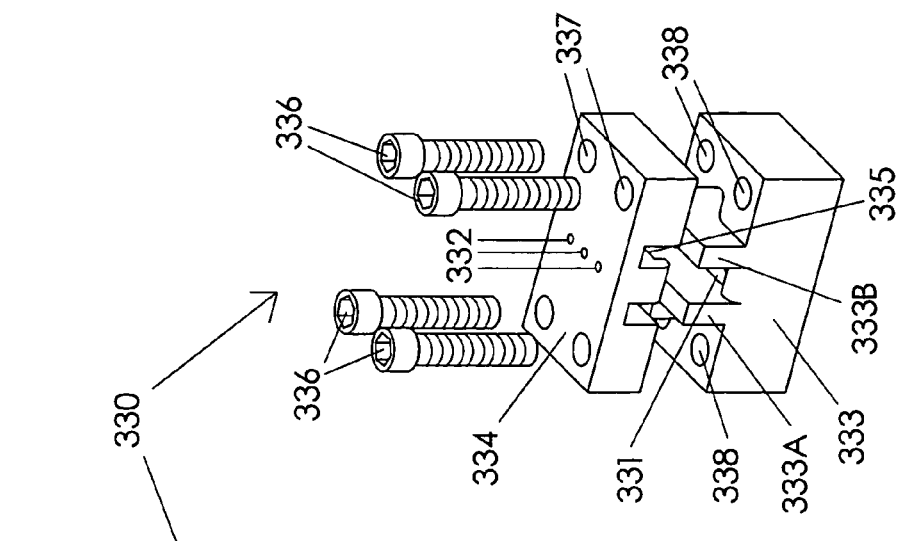
FIGS. 33A-33E are views of a template (jig or assembly fixture) used to assemble one end of a BTB (i.e., a bone block-tendon assembly).
Figure 33B:
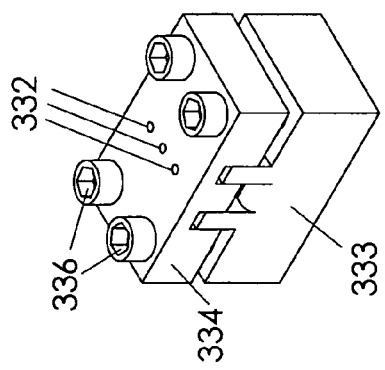
Figure 33C:
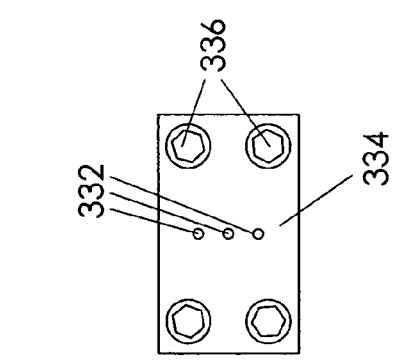
Figure 33E:
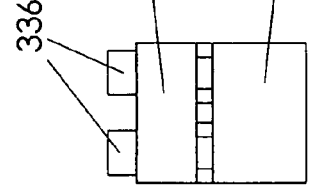
Figure 33D:
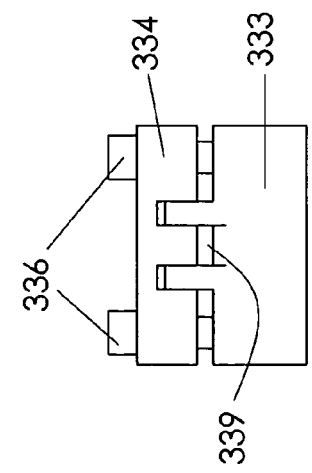

FIGS. 33A-33E are views of a template (jig) 300 used to assemble one end of a BTB (i.e., a bone block-tendon assembly). FIG. 33A is an exploded view of the template 300 showing the upper half 334 and lower half 333, and the four tensioning screws 336 for compressing upper half 334 against lower half 333. Lower half 333 has 4 threaded (tapped) holes 338 for receiving the 4 threaded screws 336. The lower half also has cavity 331 which is sized for receiving two or more bone blocks of defined length and width and height and segments of soft tissue of predefined length and width. There is a template for each bone block-tendon assembly of defined length, width and height. Cavity 331 is defined in part by side walls 333A and 333B which also act as stops when upper half 334 is compressed against lower half 333 by engagement of tensioning screws 336. In practice, the tensioning screws compress the correctly positioned bone and soft tissue segments placed in cavity 331 to the proper tension which is achieved at the engagement of the stops between the upper and lower halves. Because the holes are predrilled by a commercially available computer driven drill press or lathe, the holes 332 are merely guides for use in inserting (driving) pins into the properly aligned components of the bone block-soft tissue assembly. FIG. 33B is a perspective view of the assembled template 330 which in this locked position would place a standard amount of tension on the pre-sized bone blocks and soft tissue placed therein prior to insertion of any pins. FIG. 33C is a top view of the assembled template. FIG. 33D is a front view of the assembled template showing opening 339 where the segment of soft tissue (e.g., tendon) would extend outside the device. FIG. 33E is a side view of the assembled template.

FIGS. 34A-34D provide views of another embodiment of an assembled BTB 340 of the present invention wherein a single segment of soft tissue (e.g., tendon or ligament) 343 is doubled back around a bone block 345 to provide a double tendon BTB. Typically, the doubled up segment of the tendon is stapled, glued, sutured, woven, braided or clamped together or with an additional piece of soft tissue to prevent slippage of one tendon face against the other. FIG. 34A is a perspective view of assembled BTB 340 having an intermediate bone block 344 of the present invention sandwiching the doubled up soft tissue 343A between opposing bone block 346. Opposing bone block 346 has a surface that is smooth, textured or that has the cavities or channels that characterize the intermediate bone block of this invention. The bone block-soft tissue (e.g., tendon) assembly at the proximal end of FIG. 34A comprising bone block 344, soft tissue 343A and bone block 346 is held together as a unit by biocompatible connectors 342, as described herein (e.g., screws, pins), preferably interference pins, more preferable cortical bone pins. FIG. 34B is a top view of the BTB where the biocompatible connectors (e.g., interference pins) in the top of the opposing bone block are clearly visible. FIG. 34C is a side view showing tendon 343 doubling back on itself around bone block 345 at the left side of the figure, and showing bone block 344, soft tissue 343A and bone block 346 held together as a unit by biocompatible connectors 342 at the right side of the figure. FIG. 34D is an view of the bone block-soft tissue assembly at the proximal end of the BTB 340, as it is positioned in FIG. 34A, showing the bone blocks 344 and 346 sandwiching the doubled up tendon 343A, all being held together as a unitary assembled structure by biocompatible connector 342. In an alternate embodiment, a groove (not shown) is included in the design to accommodate the soft tissue that is external to the bone block assembly.

FIGS. 35A-35D provide views of another embodiment of an assembled BTB of the present invention wherein a single segment of soft tissue (e.g., tendon or ligament) is doubled back to provided a double tendon BTB. This embodiment is a variation of the embodiment of FIG. 34 but further includes at the turnabout end two additional bone blocks 357 and 359 that sandwich the reversing ends of tendon 353 to central bone block 355, and allow both ends of the resulting BTB 350 to provide for maximum bone to bone contact between the graft and the patient's bone when the graft is implanted in a surgically excised bone tunnel in a patient. FIG. 35A is a perspective view of the assembled BTB 350 as described above. FIG. 35A shows BTB 350 having at the proximal end in the figure an intermediate bone block 354 of the present invention having its soft tissue engaging face engaging one face of the doubled up soft tissue 353A, while bone block 356 has its soft tissue engaging face engaging the opposing face of the soft tissue. The resulting assembly of the three respective layers are sandwiched one on top of the other and are held together as a unit by biocompatible connectors 352, as described herein (e.g., screws, pins), preferably interference pins, more preferable cortical bone pins. Although 2 biocompatible connectors are shown, it is within the scope of the present embodiment that from 2-5 biocompatible connectors be used. At the distal end of the BTB 350 shown in FIG. 35A, there is a five layer sandwich comprising in stacked form from bottom to top: bone block 357, soft tissue 353, central bone block 355, soft tissue 353, and bone block 359. This 5 layer stacked assembly is held together as a unit by biocompatible connectors 352, as described herein (e.g., screws, pins), preferably interference pins, more preferable cortical bone pins. In this 5 layer assembly, at least one of bottom bone block 357, central bone block 355 or capping bone block 359 is an intermediate bone block of the present invention having its soft tissue engaging face engaging one face of tendon 353; preferably two are intermediate bone blocks, more preferably, all three are intermediate bone blocks of the present invention. FIG. 35B is a top view of the BTB 350 where the biocompatible connectors 352 in the tops of the opposing bone block-soft tissue assemblies are clearly visible. FIG. 35C is a side view showing tendon 353 doubling back and forming the above-described five layer sandwich at the left end of the figure and the above described three layer sandwich at the right end of the figure. FIG. 35D is a view of the proximal end of the BTB 350, as positioned in FIG. 35A, showing the three layer bone-soft tissue assembly (sandwich) as one looks down the length of the BTB 350. In an alternate embodiment, a groove (not shown) is included in the design to accommodate the soft tissue that is external to the bone block assembly.

FIGS. 36A-36D are a series of views of another embodiment of an assembled BTB of the present invention. FIG. 36A is a perspective view of assembled BTB 360 comprising a length of soft tissue 363 having opposing first and second ends, wherein the first end of the soft tissue is sandwiched between wedge shaped opposing bone blocks 366 and 364, the angle of the wedges being such that in combination, the wedges form a 3 dimensional shape whose opposing longitudinal surfaces are substantially parallel. This results in an intermediate bone block where the bone block (364, 366) has a lengthwise tapering (wedge shaped) profile. The resulting wedge (366):soft tissue (363):wedge (364) sandwich is held together as a unit by suitable biocompatible connectors 362, as described herein (e.g., screws, pins), preferably interference pins, more preferable cortical bone pins. Likewise, the second end of the length of soft tissue 363 is sandwiched between wedge shaped opposing bone blocks, the angle of the wedges being such that in combination, the wedges form a 3 dimensional shape whose opposing longitudinal surfaces are substantially parallel. This resulting wedge (365):soft tissue (363):wedge (364} sandwich is also held together as a unit by suitable biocompatible connectors 362, as described herein (e.g., screws, pins), preferably interference pins, more preferable cortical bone pins. Moreover, at least one of the opposing wedge shaped bone blocks 364 at each end of the length of soft tissue 363 has cavities or channels 367 such that it is an intermediate bone block of the present invention. FIG. 36B is a top view of this embodiment of assembled BTB 360. FIG. 36C is a side view of assembled BTB 360 showing the assembly details and the use of suitable biocompatible connectors. FIG. 34D is a view of the proximal end of assembled BTB 360 as positioned in FIG. 36D.

FIGS. 37A-37D show various views of the exterior profile of a preferred semi-capsule shaped embodiment of an intermediate bone block of the present invention having a sawtooth pattern of striations 371 on the tissue (e.g., tendon) engaging surface. Other embodiments of an intermediate bone block of the present invention have other striation patterns formed of angled ridges, teeth, or ridges and valleys. The textured patterns shown in FIGS. 6-10 are further examples of striations appropriate for use with the present invention. FIG. 37A is a top view of this embodiment of an intermediate bone block showing holes 372A-372C. The holes may be used for receiving a biocompatible pin or other connector that would hold the depicted intermediate bone block to any one of a variety of appropriately shaped opposing bone blocks and a segment of soft tissue sandwiched therebetween. Any or all of the holes may also be used as reference points in aligning an intermediate bone block during implantation. Three holes are shown, though it is within the scope of the present invention for from one to ten holes to be used. FIG. 37B is a perspective view showing that the exterior surface of this embodiment of an intermediate bone block has a curved notch or groove 373 for maximizing engagement with an interference screw. FIG. 37C is a side view of the intermediate bone block showing its semi-capsular shape. The pattern of ridges 371 appears from this perspective as angled teeth on the tissue engaging surface. Preferably, the angled teeth are cut such that one surface of the tooth is at a 90 degree angle to the horizontal plane of the tissue engaging surface and the other surface of the tooth is at a 30 degree angle to the horizontal plane of the tissue engaging surface. FIG. 37D is an end view of the intermediate bone block of FIG. 37A. FIG. 37E is a detail view of the saw-tooth pattern as shown on the textured surfaces in FIGS. 37A-37D.

In a preferred embodiment of an intermediate bone block, up to five holes exist in the finished block. For example, three of the five holes are filled with press fit bone dowel pins to secure the bone block assembly and the other two holes remain available for use in manipulation or fixation of the graft, either by passing suture through the holes or by interfacing directly with the holes using an instrument or fixture. In an alternative embodiment, an intermediate bone block of the present invention has no holes, and the bone block assembly is held together in another manner, including but not limited to suture or staples. The holes present invention for the holes to have other cross sectional shapes, including but not limited to slot, "D", square or other polygon. The holes illustrated in the Figures are further shown as being oriented perpendicular relative to the plane of the tissue engaging surface of the bone block. Holes appropriate for use in the present invention also have alternative alignment or orientation, including but not limited to running at an angle in one or more directions relative to the top plane of the bone block, or being offset or misaligned relative to holes in a second bone block when a bone block assembly is formed.

FIGS. 38A-38D show various views of the exterior profile of another preferred semi-capsule shaped embodiment of an intermediate bone block of the present invention having a plurality of channels with undercut omega-shaped cross sections running substantially in the intended direction of pull of a segment of soft tissue (e.g., tendon) and having a component that runs across the direction of intended pull of the segment of soft tissue. FIG. 38D is a top view of the intermediate bone block looking directly down at the stacked triple "U" shaped (or double stacked "A") layout of the channels. In this embodiment, the layout of the channels has a first component that runs lengthwise parallel wall 381 and in the intended direction of pull of a segment of soft tissue (e.g., tendon), and a second component that runs widthwise and/or across the intended direction of pull of the tendon. The layout of channels 382 that are cut into tissue engaging surface 383 leave behind a plurality of soft tissue (e.g., tendon) compression surfaces. While the embodiment of FIG. 38D shows the triple "U" pattern, other embodiments comprise channel layouts in a single "U" pattern (as in designs 2 and 3 of Table 2) or a double "U" pattern. The top view of FIG. 38D also shows holes in the intermediate bone block. One use of at least one of the holes is for receiving a biocompatible pin or other connector that would hold the depicted intermediate bone block to any one of a variety of appropriately shaped opposing bone blocks and a segment of soft tissue sandwiched therebetween. Another use for at least one of the holes is also to be used as reference points in aligning an intermediate bone block during implantation. As in FIGS. 37A-37D, three holes are shown here, though it is within the scope of the present invention for from one to ten holes to be used. FIG. 38C is a perspective view of this embodiment on an intermediate bone block showing a notch 384 cut out of the intermediate bone block. One purpose of the notch is to serve as a relief area when a segment of soft tissue is laid in channels 382 to prevent the soft tissue from becoming over compressed. FIG. 38B is a side view of this embodiment of an intermediate bone block showing it semi-capsular shape. FIG. 38A is an end view of the intermediate bone block of FIG. 38D, in which the omega ("Ω") shape of the channels 382 becomes more apparent.

In a more preferred embodiment of the present invention, the intermediate bone blocks of FIGS. 37A-37D and 38A-38D are used together as opposing bone blocks in a bone block assembly having soft tissue sandwiched therebetween. In a most preferred embodiment of the present invention, a bone block assembly using the intermediate bone blocks of FIGS. 37A-37D and 38A-38D is used as a bone component of an implant. As discussed earlier, when an implant of the present invention has a bone block assembly of the present invention at only one end of the soft tissue, the opposing end of soft tissue may be free (e.g., free tendon end) or the bone block at the second and opposing end of the soft tissue may be a naturally occurring bone block or portion of bone. When an assembled BTB of the present invention has a bone block assembly of the present invention on each of its ends, the bone block assemblies may be the same or different.

FIGS. 39A-39D provide views of another embodiment of a BTB of the present invention wherein a segment of soft tissue (e.g., tendon or ligament) 392 is gripped by a first bone component comprising a bone block assembly and is doubled back through a second bone component comprising a bone block assembly 393 to provide a double tendon BTB. The second end of the soft tissue 394, preferably the proximal end, is shown as being wrapped under bone block assembly 391. FIG. 39A is a side view of the embodiment of a BTB showing that bone block assembly 393 at the second end of the BTB is oriented at a 90 degree rotation from bone block assembly 391 at the first end of the BTB. Having bone block assemblies at both ends of the BTB provides for maximum bone to bone contact between the graft and the patient's bone when the graft is implanted in a surgically excised bone tunnel in a patient. The top of bone block assembly 393 is shown having holes 395A-395E. The holes may be used for receiving a biocompatible pin or other connector that would hold the depicted intermediate bone block to any one of a variety of appropriately shaped opposing bone blocks and a segment of soft tissue sandwiched therebetween. Any or all of the holes may also be used as reference points in aligning an intermediate bone block during implantation. Five holes are shown here, though it is within the scope of the present invention for from one to ten holes to be used. FIG. 39B is an end view of this embodiment of a BTB of the present invention as viewed looking from the tip of the bone block assembly 393 at the second end of the BTB. This view shows that bone block assembly 391 has a curved notch or groove 396 for maximizing engagement with an interference screw. Additionally, bone block assembly 393 has a curved notch or groove 397 for maximizing engagement with an interference screw. FIG. 39C is a side view of the embodiment of a BTB showing the top of bone block assembly 391 having holes 398A-398E for receiving a biocompatible pin or other connector that would hold the depicted intermediate bone block to any one of a variety of appropriately shaped opposing bone blocks and a segment of soft tissue sandwiched therebetween. Five holes are shown here, though it is within the scope of the present invention for from one to ten holes to be used. FIG. 39D is a perspective view of this embodiment showing the soft tissue extending from the first bone component to the second bone component, doubling back through the second bone component and extending back to the first bone component.

The first end of the soft tissue in FIGS. 39A-39D is shown as being finished so that its edges correspond in shape to the edges of bone block assembly 391 rather than overhanging bone block assembly 391. The second end of the soft tissue is shown in an unfinished state so that the edges do not correspond to the shape of bone block assembly 391, but instead overhang the edges of bone block assembly 391. Other embodiments of the present invention include having either end of the soft tissue conform to the shape of bone block assembly 391 while the other end does not, having both ends of the soft tissue finished to conform to the shape of bone block assembly 391, having both ends of the soft tissue unfinished so that both ends of the soft tissue overhang the of bone block assembly 391. When both end of the soft tissue overhang the end of bone block assembly 391, the overhanging ends may be attached by suture or by other types of connection, including but not limited to staples, clips, or wire.

Figure 40B:
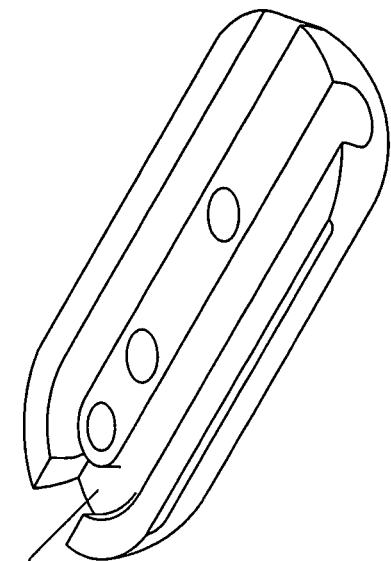
FIGS. 40A-40D provide views of an intermediate bone block of the present invention having a semi-capsular shape.
Figure 40D:
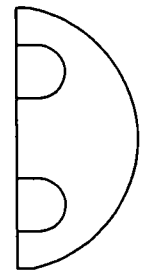
Figure 40A:
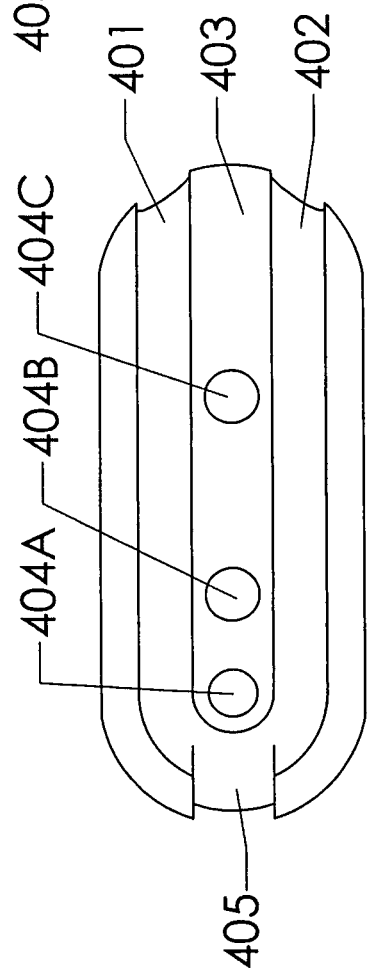
Figure 40C:
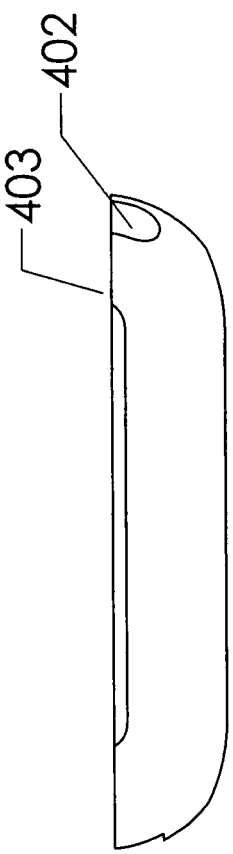

FIGS. 40A-40D provide views of an intermediate bone block of the present invention having a semi-capsular shape. FIG. 40A is a top view of the tissue engaging surface 403 of the intermediate bone block. A "U" shaped channel or groove is shown having a "U" shaped layout in the tissue engaging surface 403 of the intermediate bone block. The channel or groove is sown as having first end 401 and second end 402. Holes 404A-404C are shown for receiving a biocompatible pin or other connector that would hold the depicted intermediate bone block to any one of a variety of appropriately shaped opposing bone blocks and a segment of soft tissue sandwiched therebetween. Three holes are shown, though it is within the scope of the present invention for from one to ten holes to be used. FIG. 40B is a perspective view of this embodiment on an intermediate bone block showing a notch 405 cut out of the intermediate bone block. Soft tissue placed in the "U" shaped channel or groove may extend out of the intermediate bone block through notch 405. Soft tissue placed in the "U" shaped channel or groove may extend beyond the interior surface of notch 405 or the exterior surface of notch 405, or both. Alternatively, soft tissue may be primarily contained within the "U" shaped channel or groove, resulting in direct bone to bone contact between the two assembled bone blocks as they compress the soft tissue. FIG. 40C is a side view showing the semi-capsular shape of the intermediate bone block. FIG. 40D is an end view of the intermediate bone block in which the "U" shape of the channel or groove becomes more apparent.

While the tissue engaging surface 403 shown in FIG. 40A is smooth, similar embodiments of the present invention may optionally have a textured pattern on tissue engaging surface such as those described and shown in FIGS. 6-10. Additionally, although not shown in FIGS. 40A-40D, similar embodiments may optionally also have a curved notch or groove on the exterior surface for maximizing engagement with an interference screw, such as groove 373 shown in FIG. 37B.

In a preferred embodiment of the BTB shown in FIGS. 39A-39D, bone block assembly 391 is formed using the intermediate bone blocks of FIGS. 37A-37D and 38A-38D as opposing bone blocks with soft tissue sandwiched therebetween. A more preferred embodiment of the BTB shown in FIGS. 39A-39D additionally uses two intermediate bone blocks as sown in FIGS. 40A-40D to form bone block assembly 393. In such an embodiment, the first end of the soft tissue is gripped in bone block assembly 391, and the soft tissue is doubled back, or looped, through bone block assembly 393 such that the second end of the soft tissue makes contact underneath bone block assembly 391. When an implant of the present invention is a BTB used in [Ben, add name of procedure], the preferred tendons are Tibialis Posterior and Peroneus Longus. These types of tendons have a tendency to be more compact in distal region and fan out towards the proximal end. For this reason, in a preferred embodiment of the present invention the first end of the soft tissue is the distal end of a tendon, and the second end of the soft tissue is the proximal end of a tendon.

Additionally, tendons have a superior surface and an inferior surface, the inferior surface being the surface closest to the bone as the tendon is recovered from an autograft, allograft or xenograft source. Most preferred embodiments of implants such as those FIGS. 39A-39D and 41A-41D comprise a first bone component wherein the tissue engaging surface of an intermediate bone block of FIGS. 37A-37D engages the superior surface of a tendon and the tissue engaging surface of an intermediate bone block of FIGS. 38A-38D engages the inferior surface of the tendon. It has been found that bone block assemblies of this type have increased strength.

In another preferred embodiment, two intermediate bone blocks as shown in FIGS. 40A-40D are used to form a bone component comprising a bone block assembly and may be used alone or with the aid of sutures to fix soft tissue (e.g., tendon) in a bone tunnel without a second bone component being attached to the soft tissue, or to fix one portion of soft tissue in a bone tunnel where another portion of the soft tissue features a naturally attached bone block.

FIGS. 41A-41D provide views of another embodiment of a BTB of the present invention wherein the first end of a segment of soft tissue (e.g., tendon or ligament) 413 is gripped by a first bone component comprising a bone block assembly 411 and is doubled back through a second bone component comprising an intermediate bone block 412 to provide a double tendon BTB. Intermediate bone block 412 comprises a top, a bottom, at least two lateral sides connecting said top and said bottom, and at least one portal through said intermediate bone block from said top side to said bottom side. FIG. 41A shows a side view of this embodiment where the proximal end of the soft tissue 414 is wrapped under bone block assembly 411. The intermediate bone block at the second end of the BTB may be made from one or more pieces of bone. Preferably, the intermediate bone block at the second end of the BTB is made from one piece of bone. FIG. 41B shows an end view of this BTB embodiment. The exterior surface of intermediate bone block 412 has curved notches or grooves 415A and 415B for maximizing engagement with an interference screw. Other embodiments may have a curved notch or groove on only one side of the intermediate bone block at the second end of the BTB, or may not have any curved notches or grooves on the sides of the intermediate bone block at the second end of the BTB for engagement with an interference screw. The exterior surface of bone block assembly 411, as shown, has a curved notch or groove 416 for maximizing engagement with an interference screw. FIG. 41C is a top view of a BTB wherein portal 418 is shown through which the soft tissue passes. The second end 414 of the soft tissue is shown as being unfinished and overhanging the edges of bone block assembly 411. Other embodiments of the present invention include having either end of the soft tissue conform to the shape of bone block assembly 411 while the other end does not, having both ends of the soft tissue finished to conform to the shape of bone block assembly 411, having both ends of the soft tissue unfinished so that both ends of the soft tissue overhang the of bone block assembly 411. When both end of the soft tissue overhang the end of bone block assembly 411, the ends may be attached by suture or by other types of connection, including but not limited to staple, clip, or wire. The top of bone block assembly 411 is shown having holes 417A-417E. The holes may be used for receiving a biocompatible pin or other connector that would hold the depicted intermediate bone block to any one of a variety of appropriately shaped opposing bone blocks and a segment of soft tissue sandwiched therebetween. Any or all of the holes may also be used as reference points in aligning an intermediate bone block during implantation. Five holes are shown here, though it is within the scope of the present invention for from one to ten holes to be used. FIG. 41D is a perspective view showing soft tissue contacting the first bone component, extending from the first bone component to the second bone component, contacting the second bone component and passing through a portal in the second bone component such that it doubles back and the second end of the soft tissue contacts the underside of the first bone component.

FIGS. 42A-42D provide views of one embodiment of an intermediate bone block comprising a top, a bottom, at least two lateral sides connecting said top and said bottom, and at least one portal through said intermediate bone block from said top side to said bottom side. Additionally, the illustrated bone block comprises a leading end 422 and a trailing end opposite the leading end. This bone block may be used as the second bone component in implant embodiments such as those shown in FIGS. 41A-41D. This intermediate bone block may also be used alone or with the aid of a connector such as sutures to fix soft tissue in a bone tunnel, or to fix one portion of soft tissue in a bone tunnel where another portion of the soft tissue features a naturally attached bone block. FIG. 42A shows a bone block having a portal 421 located in leading end 422. In this embodiment, the interior wall of portal 421 forms a closed loop within the intermediate bone block, and leading end 422 is rounded to aid in insertion of the implant. In other embodiments, the interior wall of the portal is an open shape or a notch, which results in leasing end 422 having an open end rather than a closed rounded end as shown in FIGS. 42A-42D. In various embodiments the interior wall of the portal as viewed from the top side of said intermediate bone block forms a shape selected from the group comprising an oval, a circle, a curved "U", a block "U", a rectangle, a "V", and a semi-circle. FIG. 42B is an end view of the bone block having curved notches or grooves 423A and 423B on the sides of the exterior surface for maximum engagement of interference screws. One similar embodiment has only one curved notch or groove, and another embodiment has none at all. Other embodiments have other features on the exterior surface to facilitate attaching the bone block to the patient. FIG. 42C is a side view of a bone block embodiment. FIG. 42D is a perspective view of a bone block embodiment.

FIGS. 43A-43D provide views of another embodiment of an intermediate bone block of the type shown in FIGS. 42A-42D. In a preferred embodiment, at least one of the lateral sides comprises a retention feature for maintaining the graft at the site of implantation, selected from the group consisting of an interference screw groove, angled teeth, symmetrical teeth, and threads. FIG. 43A shows a bone block having a rounded end 432 with a portal 431 therein and textured exterior surfaces having striations 433 in a saw tooth pattern. FIG. 43B is an end view of a bone block of FIG. 43A. FIG. 42C is a side view of a bone block embodiment of FIG. 43A. FIG. 42D is a perspective view of a bone block embodiment of FIG. 43A. The textured exterior surfaces 433 of this embodiment facilitates fixation of the bone block at the surgical site.

FIGS. 44A-44D provide views of another embodiment of an intermediate bone block of the type shown in FIGS. 42A-42D. FIG. 44A shows a bone block having a rounded end 442 with a portal 441 therein and textured exterior surfaces 443. Exterior surfaces 443 form threads such as those of a screw. FIG. 44B is an end view of a bone block of FIG. 44A showing textured surface 443 and curved surfaces 445. When soft tissue is looped or threaded through the portal in this embodiment, the soft tissue rests against curved surface 445. FIG. 44C is a side view of a bone block embodiment of FIG. 44A. FIG. 44D is a perspective view of a bone block embodiment of FIG. 44A. The textured exterior surfaces 443 of this embodiment facilitates fixation of the bone block at the surgical site.

One example of a procedure in which intermediate bone blocks such as those shown in FIGS. 43 and 44 are useful is in medial patella femoral ligament repair or reconstruction. In such procedures, the tendon pulls outward radially from the intermediate bone block rather than pulling axially along the intermediate bone block. The intermediate bone block may thus be pushed into a patient's bone and the textured exterior is sufficient to secure the implant. Where two lateral sides of the bone block have a threaded surface, as shown in FIGS. 44A-44D, the bone bock may be pushed into a threaded bone tunnel and rotated 90 degrees to secure the implant. The act of pushing the bone block into the bone tunnel may cause the threaded surfaces of the bone block to crush portions of the threads in the threaded bone tunnel. Rotating the bone block 90 degrees once it has been pushed into the bone tunnel allows the threaded surface of the bone block to engage undamaged threads in the threaded bone tunnel, thus securing the implant.

Example 1

Intermediate Bone Blocks of the Invention Having an Omega-Shaped Cross-Section

A. Plank with Two Substantially Parallel Channels Having an Omega-Shaped Cross-Section:

Cortical bone from a long bone shaft was cut into planks using a band saw. Bone planks were then cut into rectangular bone blanks of rough dimensions 10 mm×5 mm×25 mm using a mill (Haas Automation, Oxnard, Calif.; model # TM-1, serial #34798). Each blank is then squared up and surface cut (planed) to final dimensions. One of the squared up bone blanks was laid out and templated for cutting two channels running the length of the bone blank and substantially parallel to the sidewalls of the bone blank. The rough outlines of the omega-shaped channels were cut with a 1.0 mm diameter end mill cutter. A 2.4 mm diameter ball end mill (Dremel, Racine Wis.; Dremel #107) was used to complete the omega-shaped channels as shown in FIG. 11, for the final dimensions of 1.8 mm deep.

B. Plank with a Single "U"-Shaped Layout of Channel Having an Omega-Shaped Cross-Section:

Cortical bone from a long bone shaft was cut into planks approximately xx mm thick using a band saw. Bone planks were then cut into rectangular bone blanks of rough dimensions 10 mm×5 mm×25 mm using a mill (Haas Automation, Oxnard, Calif.; model # TM-1, serial #34798). One of the bone blanks was laid out and templated for cutting a triple "U" shaped channel running the length of the bone blank and having its linear portions substantially parallel to the sidewalls of the bone blank. The rough outline of the omega-shaped channel was cut with a 1.0 mm diameter end mill cutter. A 2.4 mm diameter ball end mill (Dremel, Racine Wis.; Dremel #107) was used to complete the omega-shaped channel as shown in FIG. 17, for the final dimensions of 1.8 mm deep.

C. Plank with a Triple "U"-Shaped Layout of Channel Having an Omega-Shaped Cross-Section:

Cortical bone from a long bone shaft was cut into planks approximately xx mm thick using a band saw. Bone planks were then cut into rectangular bone blanks of rough dimensions 10 mm×5 mm×25 mm using a mill (Haas Automation, Oxnard, Calif.; model # TM-1, serial #34798). One of the bone blanks was laid out and templated for cutting a triple "U" shaped channel running the length of the bone blank and having its linear portions substantially parallel to the sidewalls of the bone blank. The rough outline of the omega-shaped channel was cut with a 1.0 mm diameter end mill cutter. A 2.4 mm diameter ball end mill (Dremel, Racine Wis.; Dremel #107) was used to complete the omega-shaped channel as shown in FIG. 17, for the final dimensions of 1.8 mm deep.

D. Semi-Capsule Shaped Intermediate Bone Block;

An intermediate bone block from Example 1 with its omega-shaped channels facing downward is clamped in place in a corner round cutter. The cutter blade is set to impart a 5 mm hemispherical radius on the end of the 10 mm wide 5 mm high bone block. Once the first end is cut, the bone block is reversed in the cutter, clamped in place, and the second end is cut to produce a bone block having a semi-hemispherical end. The bone block is then placed in a router having a 5 mm circular blade and each side wall is cut to impart a 5 mm radius. The result is a semi-capsular shaped intermediate bone block of FIG. 20.

In a more efficient method, two block ends can be cut simultaneously. Two intermediate bone blocks from Example 1 (or two blank bone planks) are manually joined together with their tissue engaging faces engaging (contacting) one another. The pair of blocks are then clamped in place in a lathe with a blade having a 5 mm radius. The blocks are slowly fed into the lathe until the radius has been cut resulting in a hemispherical end. The pair of blocks are released and then reversed in the lathe so that the opposing end can be cut. Once the opposing end is cut, the bone block is then placed in a router having a 5 mm circular blade and each side wall is cut to impart a 5 mm radius. The result is a semi-capsular shaped intermediate bone block of FIG. 20.

Example 2

Bone Block Assembly Comprising an Intermediate Bone Block and a Second Bone Block A. Bone Block of FIGS. 6A-6D with Saw Tooth Pattern of Ridges Cortical bone planks were cut from a long bone shaft using a band saw. Bone planks were then cut into rectangular bone blanks of rough dimensions 10 mm×5 mm×25 mm using a mill (Haas Automation, Oxnard, Calif.; model # TM-1, serial #34798). The mill was used to cut the serrated pattern of FIGS. 6A-6D on the upper block from a bone blank, at 0.76 mm deep, with a pitch of 0.8 teeth per mm, and at tooth angle of 30 degrees.

B. Intermediate Bone Block of FIGS. 11A-11D

The bone block of Example 2A was clamped to a surface with its ridge side up and the rough outline of two substantially parallel channels with an omega-shaped cross section were cut into the block with a 1.0 mm end mill cutter. A 2.4 mm diameter ball end mill (Dremel, Racine Wis.; Dremel #107) was used to complete the two omega-shaped channels to produce the intermediate bone block of FIG. 11.

Example 3

A Bone Tendon Assembly for Testing Grip of Bone Patterns

A. Bone Block with a Smooth Tendon Engaging Surface

Cortical bone from a long bone shaft were cut into planks using a band saw. Bone planks were then cut into rectangular bone blanks of rough dimensions 10 mm×5 mm×25 mm using a mill (Haas Automation, Oxnard, Calif.; model # TM-1, serial #34798). Each blank is then squared up and surface cut (planed) to final dimensions. A pair of these bone blocks were used to make the bone block-tendon assembly of FIG. 1.

B. Bone Block with a Saw Tooth Pattern on the Tendon Engaging Surface of 0.8 Teeth Per mm, 0.76 mm Deep, at a 30 Degree Angle to the Direction of Pull of the Tendon Cortical bone planks were cut from a long bone shaft using a band saw. Bone planks were then cut into rectangular bone blanks of rough dimensions 10 mm×5 mm×25 mm using a mill (Haas Automation, Oxnard, Calif.; model # TM-1, serial #34798). The mill was used to cut the serrated pattern of FIGS. 6A-6D on the block at 0.76 mm deep, with a pitch of 0.8 teeth per mm, and at tooth angle of 30 degrees. This bone block was used to make the bone block-tendon assembly in each of FIGS. 2A-B, 3A-B, 4A-D, 5A-D. It was also used as the opposing bone block to each of the bone blocks of designs 01-05 as reported in Table 2.

C. Intermediate Bone Block of the Invention with 2 Channels Having a Rectangular Cross-Section Cortical bone planks were cut from a long bone shaft using a band saw. Bone planks were then cut into rectangular bone blanks of rough dimensions 10 mm×5 mm×25 mm using a mill (Haas Automation, Oxnard, Calif.; model # TM-1, serial #34798). The mill was used to cut the serrated pattern of FIG. 6 on the upper block from a bone blank, at 0.76 mm deep, with a pitch of 0.8 teeth per mm, and at tooth angle of 30 degrees. The other bone block was machined with channels of a rectangular cross section. This intermediate bone block (dimensions of 25 mm×11 mm×4 mm) was machined using an end mill bit dimensioned 1.6 mm wide×2 mm deep at a placement of 2.5 mm off center. Tendon was placed between the two blocks, the blocks where then clamped to 250 Newtons, and the free end of the tendon was mechanically clamped and pulled until failure occurred.

D. Standardized Tendon for Use in Testing Load Strength of a Bone Block-Tendon Assembly Tendons selected for testing were generally about 150 mm in length, about 8 mm in width, and about 2-3 mm in thickness. Tibialis tendons were preferred.

Example 5

Method of Testing Bone Block-Tendon Assemblies for Load Strength

Bone block assemblies having different combinations of tendon engaging faces were used to sandwich a standardized length, width and thickness of tendon from Example 4D. The individual bone blocks of the bone block assemblies had a documented size of 25 mm×10 mm of tendon engaging face. The tendon engaging face differed from one another solely in the surface features that were being comparatively tested. Five combinations of bone block assemblies that were tested and reported in Table 1 comprised the following combinations of tendon engaging surfaces: smooth:smooth; smooth: ridges (saw tooth pattern); ridges (saw tooth pattern):ridges (saw tooth pattern); ridges (saw tooth pattern):2 square channels in direction of pull; and ridges (saw tooth pattern):2 omega channels in direction of pull.

The five combinations of bone block assemblies that were tested in Table 2 comprised the following combinations of tendon engaging surfaces: design 01 (double "I" layout of omega channels:ridges (saw tooth pattern)); design 02 (inverted "U" layout of omega shaped channel: ridges (saw tooth pattern)); design 03 (deep inverted "U" layout of omega shaped channel: ridges (saw tooth pattern)); design 04 (("A" shaped layout of omega shaped channel: ridges (saw tooth pattern)); and design 05 (double "A" layout of omega shaped channels: ridges (saw tooth pattern)).

Each of these five combinations were tested for their ability to hold a tendon until failure in response to an increasing tendon load measured in Newtons. Testing was accomplished by sandwiching an equal length of tendon from Example 4D between the tendon engaging faces of the opposing bone blocks. The sandwich was then placed in one end of an Instron Model 5800 (Canton Mass.) and compressed to 250 Newtons in a pneumatic grip. The opposing end of the tendon was securely clamped in the Instron between two pieces of textured metal to avoid slippage. The Instron load cell measured the load (force in Newtons) that resulted in failure of the bone block-tendon assembly, i.e., the load required to pull the tendon from the clamped bone blocks. This test was run in triplicate on each bone block-tendon combination and average of the three loads was documented and is reported in Tables 1 and 2 herein.

Example 6

BTB Having a Naturally Attached Bone at One End and a Bone Block Assembly of the Present Invention at its Opposing End The tendon and bone used to make this example were recovered using procedures common to those skilled in the art. The soft tissue grafts having a material specifications were prepared to those dimensions. For example, the Achilles specifications were, 10 mm bone block diameter, and the non-bone end trimmed to an overall length of 200 mm.

Cortical bone planks were cut from a long bone shaft using a band saw. Bone planks were then cut into rectangular bone blanks of rough dimensions 10 mm×5 mm×25 mm using a mill (Haas Automation, Oxnard, Calif.; model # TM-1, serial #34798). The mill was used to cut the serrated pattern of FIG. 6A on the upper block from a bone blank, at 0.76 mm deep, with a pitch of 0.8 teeth per mm, and at tooth angle of 30 degrees. The other bone block was machined with channels of an omega cross section. The rough outline of the omega channels were cut into the lower block with a 1.0 mm end mill cutter. A ball end mill (Dremel, Racine Wis.; Dremel #107) was used to complete the omega channel of FIG. 11 in the lower block. Cortical pins (Ø 2 mm×15 mm) were machined from the bone plank of rough dimensions 5 mm×5 mm×20 mm using a lathe (Omniturn, Farmingdale, N.Y., Model # OT-CNC, serial #3282G5AHB). Bone having density from about 1.82 g/cm3 to 1.96 g/cm3 was preferred for both the bone blocks and the cortical pins. An assembly fixture, as shown in FIGS. 33A-33F was used to hold the upper and lower bone blocks in place for the remainder of the assembly procedure. The free end of the Achilles tendon was placed between the two blocks, the blocks where then clamped in the assembly fixture. Holes for the cortical pins were then drilled through the bone block assembly using the guide holes (see FIG. 33) in the assembly fixture. The cortical pin holes were cleaned using a reamer. The cortical pins were press fit into place, then ground or cut even with the surface of the bone block after removal from the assembly fixture.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An implant comprising
a first bone component at a first end of said implant,
a second bone component at a second end of said implant; and
a segment of soft tissue having a first end, a midsection and a second end;
wherein said first bone component comprises a first bone block assembly for securing said soft tissue comprising a first intermediate bone block and a second intermediate bone block, said first intermediate bone block and said second intermediate bone block sandwiching said soft tissue therebetween; and
wherein the first end and the second end of said soft tissue contact said first bone component, and the midsection of said soft tissue contacts said second bone component, and
wherein said first intermediate bone block comprises a first tissue engaging surface that contacts one side of said soft tissue and said second intermediate bone block comprises a second tissue engaging surface that contacts an opposing side of said soft tissue; and
wherein the first tissue engaging surface of said first intermediate bone block comprises at least one compression surface and at least one cavity, said at least one compression surface for compressing said soft tissue against the second tissue engaging surface, and said at least one cavity for receiving overflow soft tissue from said at least one compression surface; and
wherein said at least one cavity comprises at least one channel having an undercut cross sectional profile,
wherein each of said first bone component, said second bone component, and
said soft tissue is an artificial tissue, allograft tissue, xenograft tissue, autograft tissue, or a combination thereof.

2. The implant of claim 1, wherein said bone components comprise cortical bone, cancellous bone or both.

3. The implant of claim 1, wherein said soft tissue is selected from the group consisting of one to ten tendons, one to ten ligaments, an isolated segment or segments of pericardium, dermis, fascia, dura, skin, submucosal tissue, cartilage, or a combination thereof.

4. The implant of claim 1, wherein the second tissue engaging surface of said second intermediate bone block comprises a textured surface.

5. The implant of claim 4, wherein said textured surface comprises striations.

6. The implant of claim 4, wherein said textured surface comprises teeth.

7. The implant of claim 1, wherein said at least one channel comprises an undercut cross-sectional profile selected from the group consisting of triangular, dovetail, omega and a combination thereof.

8. The implant of claim 7, wherein said at least one channel comprises an omega cross-sectional profile.

9. The implant of claim 1, wherein said second bone component comprises a second bone block assembly for securing said soft tissue comprising a third intermediate bone block and a fourth intermediate bone block, said third intermediate bone block and said fourth intermediate bone block sandwiching said soft tissue therebetween.

10. The implant of claim 9, wherein the third intermediate bone block of the second bone component comprises at least one channel for receiving said soft tissue.

11. The implant of claim 10, wherein said at least one channel of the third intermediate bone block comprises a cross-sectional profile selected from the group consisting of rectangular, square, semi-circular, semi-ovular, triangular, trapezoidal, sinusoidal, curvilinear, dovetail, omega and a combination thereof.

12. The implant of claim 10, wherein said at least one channel of the third intermediate bone block comprises a layout in a third tissue engaging surface of said third intermediate bone block for receiving said soft tissue and doubling back said soft tissue such that said soft tissue exits said third intermediate bone block on the same side through which said soft tissue enters said third intermediate bone block.

13. The implant of claim 12, wherein said layout is in a shape selected from the group consisting of a "V" shape, a "U" shape, an "A" shape, a semi-circle, and semi-oval.

14. The implant of claim 9, wherein said fourth intermediate bone block of said second bone component comprises at least one channel for receiving said soft tissue.

15. The implant of claim 14, wherein said at least one channel of the fourth intermediate bone block comprises a cross-sectional profile selected from the group consisting of rectangular, square, semi-circular, semi-ovular, triangular, trapezoidal, sinusoidal, curvilinear, dovetail, omega and a combination thereof.

16. The implant of claim 14, wherein said at least one channel of the fourth intermediate bone block comprises a layout in a fourth tissue engaging surface of said fourth intermediate bone block for receiving said soft tissue and doubling back said soft tissue such that said soft tissue exits said fourth intermediate bone block on the same side through which said soft tissue enters said fourth intermediate bone block.

17. The implant of claim 16, wherein said layout is in a shape selected from the group consisting of a "V" shape, a "U" shape, an "A" shape, a semi-circle, and semi-oval.

18. An implant of claim 9, wherein said third intermediate bone block of said second bone component comprises at least one channel for receiving said soft tissue and said fourth intermediate bone block of said second bone component comprises at least one channel for receiving said soft tissue.

19. The implant of claim 1, wherein said second bone component comprises a third intermediate bone block comprising a top, a bottom, at least two lateral sides connecting said top and said bottom, and at least one portal through said third intermediate bone block from said top side to said bottom side.

20. An implant of claim 19, wherein said portal comprises at least one interior wall for engaging the soft tissue.

21. An implant of claim 20, wherein the soft tissue engages the top side of said third intermediate bone block, passes through the portal of said third intermediate bone block, and doubles back such that it engages the bottom side of said third intermediate bone block.

22. An implant of claim 20, wherein said at least one interior wall as viewed from the top side of said third intermediate bone block forms a shape selected from the group comprising an oval, a circle, a curved "U", a block "U", a rectangle, a "V", and a semi-circle.

23. An implant of claim 20, wherein said at least one interior wall forms a closed loop within said third intermediate bone block.

24. An implant of claim 19, wherein said portal comprises a notch at one end of said third intermediate bone block.

25. An implant of claim 19, wherein at least one of said lateral sides comprises at least one groove on an outer surface to accommodate at least one interference screw.

26. An implant of claim 19, wherein at least one of said lateral sides comprises a textured surface.

27. An implant of claim 26, wherein said textured surface comprises threads or tapped threads.

28. An implant comprising:
a first bone component at a first end of said implant,
a second bone component at a second end of said implant; and
a segment of soft tissue of sufficient length to extend between said first and second bone components;
wherein said first bone component comprises a first bone block assembly for securing said soft tissue comprising a first intermediate bone block and a second intermediate bone block, said first intermediate bone block and said second intermediate bone block sandwiching said soft tissue therebetween, and wherein said first intermediate bone block has a first tissue engaging surface which comprises at least one compression surface and at least one cavity; and wherein said at least one cavity comprises at least one channel having an undercut cross sectional profile; and
wherein said second bone component comprises a second bone block assembly comprising a third intermediate bone block and a fourth intermediate bone block, said third intermediate bone block and said fourth intermediate bone block sandwiching said soft tissue therebetween, and
wherein said soft tissue extends from said first bone component to said second bone component, is doubled back through or around said second bone component, and extends back to said first bone component,
wherein each of said first bone component, said second bone component, and said soft tissue is an artificial tissue, allograft tissue, xenograft tissue, autograft tissue, or a combination thereof.

29. An implant comprising:
a first bone component at a first end of said implant,
a second bone component at a second end of said implant; and
a segment of soft tissue of sufficient length to extend between said first and second bone components;
wherein said first bone component comprises a bone block assembly for securing said soft tissue comprising a first intermediate bone block and a second intermediate bone block, said first intermediate bone block and said second intermediate bone block sandwiching said soft tissue therebetween, and wherein said first intermediate bone block has a first tissue engaging surface which comprises at least one compression surface and at least one cavity; and wherein said at least one cavity comprises at least one channel having an undercut cross sectional profile; and
wherein said second bone component comprises a third intermediate bone block comprising a top, a bottom, at least two lateral sides connecting said top and said bottom, and at least one portal through said third intermediate bone block from said top side to said bottom side, and wherein said soft tissue contacts the first bone component in at least two places along a length of said soft tissue, and said soft tissue contacts the second bone component in at least one place along the length of said soft tissue, wherein each of said first bone component, said second bone component, and said soft tissue is an artificial tissue, allograft tissue, xenograft tissue, autograft tissue, or a combination thereof.

30. An implant comprising:

a soft tissue component, a first bone component, and a second bone component, wherein the soft tissue component is of sufficient length to extend between said first and second bone components;

wherein said first bone component comprises a bone block assembly for securing said soft tissue comprising at least two intermediate bone blocks, said at least two intermediate bone blocks sandwiching said soft tissue component therebetween, one of said at least two intermediate bone blocks having a tissue engaging surface which comprises at least one compression surface and at least one channel having an undercut cross sectional profile; and wherein said second bone component comprises a top, a bottom, a leading end, a trailing end, at least two lateral sides connecting said top and said bottom, and at least one portal through said bone second bone component from said top side to said bottom side sized to accept said soft tissue component, wherein each of said first bone component, said second bone component, and said soft tissue component is an artificial tissue, allograft tissue, xenograft tissue, autograft tissue, or a combination thereof.

31. An implant of claim 30, wherein one of said lateral sides comprise a retention feature for maintaining the implant at a site of implantation, selected from the group consisting of an interference screw groove, angled teeth, symmetrical teeth, and threads.

32. An implant of claim 30, wherein said portal is located at said leading end, said leading end being rounded to aid in insertion of the implant.

* * * * *